US012767716B2

(12) United States Patent
Almagro et al.

(10) Patent No.: US 12,767,716 B2
(45) Date of Patent: Oct. 20, 2026

(54) ANTI-PD-1 ANTIBODIES AND METHODS OF USE

(71) Applicants: Juan Carlos Almagro, Cambridge, MA (US); Sonia Mayra Perez-Tapia, Mexico City (MX)

(72) Inventors: Juan Carlos Almagro, Cambridge, MA (US); Sonia Mayra Perez-Tapia, Mexico City (MX)

( * ) Notice: Subject to any disclaimer, the term of this patent is extended or adjusted under 35 U.S.C. 154(b) by 0 days.

(21) Appl. No.: 19/396,723

(22) Filed: Nov. 21, 2025

(65) Prior Publication Data

US 2026/0146090 A1 May 28, 2026

Related U.S. Application Data

(60) Provisional application No. 63/837,208, filed on Jul. 2, 2025, provisional application No. 63/762,358, filed on Feb. 24, 2025, provisional application No. 63/723,959, filed on Nov. 22, 2024.

(51) Int. Cl.

| | |
|---|---|
| ***C07K 16/00*** | (2006.01) |
| ***A61K 39/395*** | (2006.01) |
| ***A61P 35/00*** | (2006.01) |
| ***C07K 16/28*** | (2006.01) |
| *A61K 39/00* | (2006.01) |

(52) U.S. Cl.

CPC .......... *C07K 16/2818* (2013.01); *A61P 35/00* (2018.01); *A61K 2039/505* (2013.01); *C07K 2317/24* (2013.01); *C07K 2317/52* (2013.01); *C07K 2317/569* (2013.01); *C07K 2317/92* (2013.01)

(58) Field of Classification Search

CPC .......................... A61P 35/00; A61K 2039/505

See application file for complete search history.

(56) References Cited

U.S. PATENT DOCUMENTS

| | | | |
|---|---|---|---|
| 4,526,938 | A | 7/1985 | Churchill |
| 4,816,567 | A | 3/1989 | Cabilly et al. |
| 5,128,326 | A | 7/1992 | Balazs |
| 5,223,409 | A | 6/1993 | Ladner |
| 5,225,539 | A | 7/1993 | Winter |
| 5,403,484 | A | 4/1995 | Ladner |
| 5,427,908 | A | 6/1995 | Dower |
| 5,516,637 | A | 5/1996 | Huang |
| 5,530,101 | A | 6/1996 | Queen et al. |
| 5,565,332 | A | 10/1996 | Hoogenboom |
| 5,571,698 | A | 11/1996 | Ladner |
| 5,580,717 | A | 12/1996 | Dower |
| 5,585,089 | A | 12/1996 | Queen et al. |
| 5,658,727 | A | 8/1997 | Barbas |
| 5,679,377 | A | 10/1997 | Bernstein |
| 5,698,426 | A | 12/1997 | Huse |
| 5,733,743 | A | 3/1998 | Johnson |
| 5,750,753 | A | 5/1998 | Kimae |
| 5,766,886 | A | 6/1998 | Studnicka |
| 5,770,196 | A | 6/1998 | Studnicka |
| 5,780,225 | A | 7/1998 | Wigler |
| 5,821,047 | A | 10/1998 | Garrard |
| 5,821,123 | A | 10/1998 | Studnicka |
| 5,869,619 | A | 2/1999 | Studnicka |
| 5,912,015 | A | 6/1999 | Bernstein |
| 5,916,597 | A | 6/1999 | Lee |
| 5,969,108 | A | 10/1999 | McCafferty |
| 5,989,463 | A | 11/1999 | Tracy |
| 6,075,181 | A | 6/2000 | Kucherlapati |
| 6,150,584 | A | 11/2000 | Kucherlapati |
| 6,407,213 | B1 | 6/2002 | Carter |
| 6,962,810 | B2 | 11/2005 | Fraser |
| 7,078,387 | B1 | 7/2006 | Leiden |
| 2005/0042664 | A1 | 2/2005 | Wu |
| 2021/0087291 | A1 | 3/2021 | Klein |

FOREIGN PATENT DOCUMENTS

| | | | |
|---|---|---|---|
| EP | 239400 | A2 | 9/1987 |
| EP | 519596 | A1 | 12/1992 |
| EP | 592106 | A1 | 4/1994 |
| WO | 199002809 | A1 | 3/1990 |
| WO | 199105548 | A1 | 5/1991 |
| WO | 199109967 | A1 | 7/1991 |
| WO | 199110737 | A1 | 7/1991 |
| WO | 199201047 | A1 | 1/1992 |
| WO | 199209690 | A2 | 6/1992 |
| WO | 199218619 | A1 | 10/1992 |
| WO | 199303769 | A1 | 3/1993 |
| WO | 199309239 | A1 | 5/1993 |
| WO | 199311236 | A1 | 6/1993 |
| WO | 199311794 | A1 | 6/1993 |
| WO | 199317105 | A1 | 9/1993 |
| WO | 199319191 | A1 | 9/1993 |

(Continued)

OTHER PUBLICATIONS

Paul, Fundamental Immunology, 3rd Edition, 1993, pp. 292-295.*
Rudikoff et al, Proc. Natl. Acad. Sci. USA, 79(6):1979-1983, Mar. 1982.*
Colman P. M., Research in Immunology, 145:33-36, 1994.*
MacCallum et al, J. Mol. Biol., 262, 732-745, 1996.*
Casset et al, Biochemical and Biophysical Research Communications, 2003, vol. 307, pp. 198-205.*

(Continued)

*Primary Examiner* — Mark Halvorson

(74) *Attorney, Agent, or Firm* — Greenberg Traurig, LLP

(57) ABSTRACT

Provided herein are binding molecules that bind to programmed cell death protein 1 (PD-1). Such binding molecules block the interaction between PD-1 and programmed death-ligand 1 and 2 (PD-L1 and PD-L2). Also provided herein are methods of using such binding molecules for preventing and treating cancer.

19 Claims, 41 Drawing Sheets

Specification includes a Sequence Listing.

(56) References Cited

FOREIGN PATENT DOCUMENTS

| | | | |
|---|---|---|---|
| WO | 199412649 | A2 | 6/1994 |
| WO | 199428938 | A1 | 12/1994 |
| WO | 199500655 | A1 | 1/1995 |
| WO | 199511984 | A2 | 5/1995 |
| WO | 199515982 | A2 | 6/1995 |
| WO | 199520401 | A1 | 8/1995 |
| WO | 199620698 | A2 | 7/1996 |
| WO | 199713844 | A1 | 4/1997 |
| WO | 199915154 | A1 | 4/1999 |
| WO | 199920253 | A1 | 4/1999 |
| WO | 2002088346 | A2 | 11/2002 |
| WO | 2008027384 | A1 | 3/2008 |
| WO | 2013059343 | A1 | 4/2013 |
| WO | 2014023709 | A1 | 2/2014 |

OTHER PUBLICATIONS

Holm et al, Molecular Immunology, 2007, vol. 44, pp. 1075-1084.*

Sims et al, A Humanized CD18 Antibody Can Block Function without Cell Destruction, J. Immunol., 1993, vol. 151:2296-308.

Sirin et al., Regulating gene expression using self-inactivating lentiviral vectors containing the mifepristone-inducible system, Gene, 2003, vol. 323:67-77.

Skerra, et al, Bacterial expression of immunoglobulin fragments, Curr. Opinion in Immunol., 1993, vol. 5:256-62.

Song et al., Antibody Mediated Lung Targeting of Long-Circulating Emulsions, PDA J. of Pharma. Sci. &Tech., 1995, vol. 50: 372-97.

Studnicka, et al, Human-engineered monoclonal antibodies retain full specific binding activity by preserving non-CDR complementaritymodulating residues, Protein Engineering, 1994, vol. 7(6):805-814.

Suzuki, et al. Anti-PD-1 antibodies recognizing the membrane-proximal region are PD-1 agonists that can down-regulate inflammatory diseases. Sci Immunol. 2023; vol. 8, . p1-13. doi:10.1126/sciimmunol.add4947.

Suzuki, et al. Importance of neonatal FcR in regulating the serum half-life of therapeutic proteins containing the Fc domain of human IgG1: a comparative study of the affinity of monoclonal antibodies and Fc-fusion proteins to human neonatal FcR. J Immunol. 2010; vol. 184(4):1968-1976. doi:10.4049/JIMMUNOL.0903296.

Takahashi et al., Rescue from Photoreceptor Degeneration in the rd Mouse by Human Immunodeficiency Virus Vector-Mediated Gene Transfer, J Virol, 1999, vol. 73:7812-7816.

Tan et al., "Superhumanized" Antibodies: Reduction of Immunogenic Potential by Complementarity-Determining Region Grafting with Human Germline Sequences: Application to an Anti-CD281, J. Immunol., 2002, vol. 169:1119-25.

Taylor, et al, A transgenic mouse that expresses a diversity of human sequence heavy and light chain immunoglobulins, Nucl. Acids Res., 1992, vol. 20:6287-6295.

Top 10 Projected Best-Selling Drugs in 2024. https://www.biochempeg.com/article/382.html. Accessed on Feb. 26, 2025 downloaded Nov. 19, 2025.

Vajdos et al., Comprehensive Functional Maps of the Antigenbinding Site of an Anti-ErbB2 Antibody Obtained with Shotgun Scanning Mutagenesis, J Mol Biol, 2002, vol. 320:415-428.

Van Dijk et al, Human antibodies as next generation therapeutics, Curr. Opin. Pharmacol, 2001, vol. 5: 368-74.

VanSeggelen et al., T Cells Engineered With Chimeric Antigen Receptors Targeting NKG2D Ligands Display Lethal Toxicity in Mice, Mol Ther (2015) 23(10):1600-1610.

Voynov, et al. Dynamic Fluctuations of Protein-Carbohydrate Interactions Promote Protein Aggregation. PLoS One. 2009; vol. 4(12):e8425, p. 1-10. doi:10.1371/JOURNAL.PONE.0008425.

Wang et al., Targeting Fibroblast Activation Protein in Tumor Stroma with Chimeric Antigen Receptor T Cells Can Inhibit Tumor Growth and Augment Host Immunity Without Severe Toxicity, Cancer Immunol Res, 2014, vol. 2 (2):154-166.

Whitelegg and Rees, WAM: an improved algorithm for modelling antibodies on the WEB, Protein Eng., 2000, vol. 13:819-24.

Wilkie et al., Dual Targeting of ErbB2 and MUC1 in Breast Cancer Using Chimeric Antigen Receptors Engineered to Provide Complementary Signaling, J Clin Immunol, 2012, vol. 32:1059-1070.

Winter et al, Making Antibodies by Phage Display Technology, Ann. Rev. Immunol., 1994, vol. 12:433-55.

Yi et al., Combination strategies with PD-1/PD-L1 blockade: current advances and future directions. Mol Cancer. 2022; vol. 21(28), p. 1-27. doi:10.1186/S12943-021-01489-2.

Luo et al. Benchmark Glycan Profile of Therapeutic Monoclonal Antibodies Produced by Mammalian Cell Expression Systems. Pharm Res. 2024; vol. 41:29-37. doi:10.1007/s11095-023-03628-4.

Luo et al., Bifunctional aHER2/cd3 RNA-engineered CART-like human T cells specifically eliminate HER2+ gastric cancer, Cell Res, 2016, vol. 26:850-853.

Marks et al, By-Passing Immunization: Building High Affinity Human Antibodies by Chain Shuffling, Nature Biotechnology, 1992, vol. 10:779-83.

Marks, et al, By-passing Immunization Human Antibodies from V-gene Libraries Displayed on Phage, J. Mol. Biol., 1991, vol. 222:581-597.

Mendelson et al., Expression and Rescue of a Nonselected Marker from an Integrated AAV Vector, Virol. 1988, vol. 166:154-165.

Menzen et al., High-Throughput Melting-Temperature Analysis of a Monoclonal Antibody by Differential Scanning Fluorimetry in the Presence of Surfactants. J Pharm Sci. 2013; vol. 102(2):415-428. doi:10.1002/jps.23405.

Miskey et al., The Frog Prince: a reconstructed transposon from Rana pipiens with high transpositional activity in vertebrate cells, Nucleic Acids Res., 2003, vol. 31(23):6873-6881.

Miyoshi et al., Stable and efficient gene transfer into the retina using an HIV-based lentiviral vector, PNAS, 1997, vol. 94:10319-10323.

Moon et al, Expression of a Functional CCR2 Receptor Enhances Tumor Localization and Tumor Eradication by Retargeted Human T cells Expressing a Mesothelin-Specific Chimeric Antibody ReceptorClin Cancer Res, 2011, vol. 17(14):4719-30.

Moon et al., Blockade of Programmed Death 1 Augments the Ability of Human T cells Engineered to Target NY-ESO-1 to Control Tumor Growth after Adoptive Transfer, Cancer Res, 2016, vol. 22(2):436-447.

Morea et al, Antibody Modeling: Implications for Engineering and Design, Methods, 2000, vol. 20(3):267-79.

Morgan et al., Case Report of a Serious Adverse Event Following the Administration of T Cells Transduced With a Chimeric Antigen Receptor Recognizing ERBB2, Mol Ther, 2010, vol. 18(4):843-851.

Morgan et al., Recognition of Glioma Stem Cells by Genetically Modified T Cells Targeting EGFRvlll and Development of Adoptive Cell Therapy for Glioma, Hum Gene Ther, 2012, vol. 23:1043-1053.

Morgensztern et al., Nivolumab and Pembrolizumab for Non-Small Cell Lung Cancer. Clin Cancer Res. 2016; vol. 22 (15):3713-3717. doi:10.1158/1078-0432.CCR-15-2998.

Morrison, el al., Chimeric human antibody molecules: Mouse antigen-binding domains with human constant region domains, Proc. Natl. Acad. Sci. USA, 1984, vol. 81:6851-55.

Munson et al, Ligand: A Versatile Computerized Approach for Characterization of Ligand-Binding Systems, Anal. Biochem., 1980, vol. 107:220-39.

Myers and Miller, Optimal alignments in linear space, CABIOS, 1988, vol. 4(1):11-17.

Nakazawa et al., PiggyBac-mediated Cancer Immunotherapy Using EBV-specific Cytotoxic T-cells Expressing HER2-specific Chimeric Antigen Receptor, Mol Ther, 2011, vol. 19(12):2133-2143.

Needleman and Wunsch, A General Method Applicable to the Search for Similarities in the Amino Acid Sequence of Two Proteins, J. Mol. Biol., 1970, vol. 48:443.

Newman, et al. Modification of the Fc Region of a Primatized IgG Antibody to Human CD4 Retains Its Ability to Modulate CD4 Receptors but Does Not Deplete CD4+ T Cells in Chimpanzees. Clinical Immunology. 2001; vol. 98 (2):164-174. doi:10.1006/clim.2000.4975.

Ning et al., Intratumoral radioimmunotherapy of a human colon cancer xenograft using a sustained-release gel, Radiotherapy & Oncology, 1996, vol. 39: 179-89.

(56) References Cited

OTHER PUBLICATIONS

Opdivo (nivolumab) FDA Approval History—Drugs.com. Accessed Jan. 20, 2025, downloaded Nov. 19, 2025. https://www.drugs.com/history/opdivo.html.
Padlan, A Possible Procedure for Reducing the Immunogenicity of Antibody Variable Domains While Preserving Their Ligand-Binding Properties, Molecular Immunology, 1991, vol. 28(4/5):489-498.
Padlan, et al, Identification of specificity-determining residues in antibodies, FASEB J., 1995, vol. 9: 133-9.
Panyam et al., Biodegradable nanoparticles for drug and gene delivery to cells and tissue, Adv Drug Deliv Rev. Sep. 13, 2012. pii: S0169-409X(12)00283-9.
Park et al., Adoptive Transfer of Chimeric Antigen Receptor Re-directed Cytolytic T Lymphocyte Clones in Patients with Neuroblastoma, Mol Ther, 2007, vol. 15(4):825-833.
Park et al., Molecular basis of PD-1 blockade by dostarlimab, the FDA-approved antibody for cancer immunotherapy. Biochem Biophys Res Commun. 2022; vol. 599:31-37. doi:10.1016/j.bbrc.2022.02.026.
Parvez, et al. PD-1 and PD-L1: architects of immune symphony and immunotherapy breakthroughs in cancer treatment. Front Immunol. 2023; vol. 14:1296341, p. 1-16. doi:10.3389/FIMMU.2023.1296341.
Pearson and Lipman, Improved tools for biological sequence comparison, Proc. Nat'l. Acad. Sci. USA, 1988, vol. 85:2444-2448.
Pedersen, et al, Comparison of Surface Accessible Residues in Human and Murine Immunoglobulin Fv Domains, J. Mol. Biol., 1994, vol. 235:959-73.
Persaud, et al. Involvement of the VEGF receptor 3 in tubular morphogenesis demonstrated with a human anti-human VEGFR-3 monoclonal antibody that antagonizes receptor activation by VEGF-C. J Cell Sci. 2004; vol. 117(Pt 13):2745-2756. doi:10.1242/JCS.01138.
Persic, et al, An integrated vector system for the eukaryotic expression of antibodies or their fragments after selection from phage display libraries, Gene, 1997, vol. 187:9-18.
Petersen, et al. Regulatory Approved Monoclonal Antibodies Contain Framework Mutations Predicted From Human Antibody Repertoires. Front Immunol. 2021; vol. 12:728694, p. 1-17. doi:10.3389/FIMMU.2021.728694/FULL.
Pluckthun and Skerra, Expression of Functional Antibody Fv and Fab Fragments in *Escherichia coli*, Meth. Enzymol., 1989, vol. 178:497-515.
Pluckthun, Mono- and Bivalent Antibody Fragments Produced in *Escherichia coli*: Engineering, Folding and Antigen Binding Immunol. Revs., 1992, vol. 130:151-88.
Presta et al, Humanization of an Antibody Directed Against IgE, J Immunol., 1993, vol. 151:2623-32.
Proudfoot, Transcriptional interference and termination between duplicated α-globin gene constructs suggests a novel mechanism for gene regulation, Nature, 1986, 322:52.
Richaud et al., Exploiting the Innate Plasticity of the Programmed Cell Death-1 (PD1) Receptor to Design Pembrolizumab H3 Loop Mimics**, ChemBioChem, 2022; vol. 23(21), p. 1-21; doi:10.1002/cbic.202200449.
Roguska, et al, A comparison of two murine monoclonal antibodies humanized by CDR-grafting and variable domain resurfacing, Protein Eng., 1996, vol. 9(10):895-904.
Roguska, et al., Humanization of murine monoclonal antibodies through variable domain resurfacing, Proc. Natl. Acad. Sci. USA, 1994, vol. 91:969-73.
Rolling et al., Evaluation of Adeno-Associated Virus-Mediated Gene Transfer into the Rat Retina by Clinical Fluorescence Photography, Hum Gene Ther, 1999, vol. 10:641-648.
Sakamoto et al., A vitrectomy improves the transfection efficiency of adenoviral vector-mediated gene transfer to Muller cells, Gene Ther, 1998, vol. 5:1088-1097.
Sali and Blundell, Comparative Protein Modelling by Satisfaction of Spatial Restraints, J. Mol. Biol., 1993, vol. 234:779-815.
Samulski et al., Helper-Free Stocks of Recombinant Adeno-Associated Viruses: Normal Integration Does Not Require Viral Gene Expression, J. Vir., 1989, vol. 63:3822-3828.
Sandhu, U.S., A rapid procedure for the humanization of monoclonal antibodies*, Gene, 1994, vol. 150(2):409-10.
Saudek et al., A Preliminary Trial of the Programmable Implantable Medication System for Insulin Delivery, N. Engl. J. Med., 1989, vol. 321: 569-74.
Schlapschy et al, Functional humanization of an anti-CD30 Fab fragment for the immunotherapy of Hodgkin's lymphoma using an in vitro evolution approach, Protein Eng. Des. Sel, 2004, vol. 17:847-60.
Schlothauer, et al. Novel human IgG1 and IgG4 Fc-engineered antibodies with completely abolished immune effector functions. Protein Eng Des Sel. 2016; vol. 29(10):457-466. doi: 10.1093/PROTEIN/GZW040.
Sefton, Implantable Pumps, Crit. Rev. Biomed. Eng., 1987, vol. 14: 201-40.
Silva et al., The S228P Mutation Prevents <em>in Vivo</em> and <em>in Vitro</em> lgG4 Fab-arm Exchange as Demonstrated using a Combination of Novel Quantitative Immunoassays and Physiological Matrix Preparation. Journal of Biological Chemistry. 2015; vol. 290(9):5462-5469. doi:10.1074/jbc.M114.600973.
Foote and Winter, Antibody Framework Residues Affecting the Conformation of the Hypervariable Loops, J. Mol. Biol., 1992, vol. 224:487-499.
Gjetting, et al., Sym021, a promising anti-PD1 clinical candidate antibody derived from a new chicken antibody discovery platform. MAbs. 2019; 11(4):666-680. doi:10.1080/19420862.2019.1596514.
Glanville, et al. Precise determination of the diversity of a combinatorial antibody library gives insight into the human immunoglobulin repertoire. Proc Natl Acad Sci U S A. 2009; vol. 106(48):20216-20221. doi:10.1073/PNAS.0909775106.
Goodson, Dental Applications, Medical Applications of Controlled Release, 1984, vol. 2, 115-38.
Gordeev, et al. Preclinical comparison of prolgolimab, pembrolizumab and nivolumab. Scientific Reports 2024,14, 23136:1-13. doi:10.1038/s41598-024-72118-3.
Grada et al., TanCAR: A Novel Bispecific Chimeric Antigen Receptor for Cancer Immunotherapy, Mol Ther Nucleic Acids, 2013, vol. 2, e105, p. 1-11.
Griffiths et al, Human anti-self antibodies with high specificity from phage display libraries, EMBO J, 1993, vol. 12:725-734.
Guex and Peitsch, SWISS-MODEL and the Swiss-PdbViewer: An environment for comparative protein modeling, Electrophoresis, 1997, vol. 18:2714-2723.
Hale G. Living in LALA land? Forty years of attenuating Fc effector functions. Immunol Rev. 2024; vol. 328: 422-437. doi:10.1111/IMR.13379.
Han et al., PD-1/PD-L1 pathway: current researches in cancer. Am J Cancer Res. 2020;10(3):727-742. Accessed Feb. 3, 2025. https://pmc.ncbi.nlm.nih.gov/articles/PMC7136921/.
Honegger and Pluckthun, Yet Another Numbering Scheme for Immunoglobulin Variable Domains: An Automatic Modeling and Analysis Tool, J. Mol. Biol., 2001, 309: 657-670.
Hoogenboom and Winter, By-passing Immunisation Human Antibodies from Synthetic Repertoires of Germline VH Gene Segments Rearranged in Vitro, J. Mol. Biol., 1992, vol. 227:381-388.
Hoogenboom, Selecting and screening recombinant antibody libraries, Nat. Biotechnol., 2005, vol. 23:1105-1116.
Howard et al., Intercerebral drug delivery in rates with lesion-induced memory deficits, J. Neurosurg., 1989, vol. 71: 105-112.
Huston, et al, Antigen Recognition and Targeted Delivery by the Single-Chain Fv, Cell Biophysics, 1993, vol. 22:189-224.
Irion et al., Identification and targeting of the ROSA26 locus in human embryonic stem cells, Nature Biotechnology, 2007, vol. 25, 1477-1482.
Ishida et al., Induced expression of PD-1, a novel member of the immunoglobulin gene superfamily, upon programmed cell death. EMBO J. 1992;11(11):3887-3895. doi:10.1002/J.1460-2075.1992.TB05481.X.

(56) References Cited

OTHER PUBLICATIONS

Ito et al., Effects of subclass change on the structural stability of chimeric, humanized, and human antibodies under thermal stress. Protein Sci. 2013;22:1542-1551. doi:10.1002/pro.2340.
Izsvak et al., Sleeping Beauty, a Wide Host-range Transposon Vector for Generic Transformation in Vertebrates, J. Mol. Biol., 2000, vol. 302: 93-102.
Jakobovits, Production of fully human antibodies by transgenic mice, Curr. Opin. Biotechnol., 1995, vol. 6(5):561-566.
Jomary et al., Rescue of photoreceptor function by AAV-mediated gene transfer in a mouse model of inherited retinal degeneration, Gene Ther, 1997, vol. 4:683-690.
Jones, et al., Deimmunization of Monoclonal Antibodies, Methods Mol Biol., 2009, vol. 525:405-423.
Kashmiri, et al, SDR grafting—a new approach to antibody humanization, Methods, 2005, vol. 36:25-34.
Katz et al., Phase I Hepatic Immunotherapy for Metastases study of intra-arterial chimeric antigen receptor modified T cell therapy for CEA+ liver metastases, Clin Cancer Res, 2015, vol. 21 (14):3149-3159.
Kawakami et al., Identification of a functional transposase of the Tol2 element, an Ac-like element from the Japanese medaka fish, and its transposition in the zebrafish germ lineage, Proc Natl Acad Sci USA, 2000, vol. 97 (21):11403-11408. doi: 10.1073/pnas.97.21.11403.
Kershaw et al., A Phase I Study on Adoptive Immunotherapy Using Gene-Modified T Cells for Ovarian Cancer, Clin Cancer Res, 2006, vol. 12(20):6106-6015.
Kettleborough, et al., Isolation of tumor cell-specific single-chain Fv from immunized mice using phage-antibody libraries and the re-construction of whole antibodies from these antibody fragments, Eur. J. Immunol., 1994, vol. 24:952-958.
Keytruda (pembrolizumab) FDA Approval History—Drugs.com. Accessed Jan. 20, 2025, downloaded Nov. 19, 2025. https://www.drugs.com/history/keytruda.html.
Kobold et al., Selective Bispecific T Cell Recruiting Antibody and Antitumor Activity of Adoptive T Cell Transfer, J Natl Cancer Inst, 2014, vol. 107(1): p. 1-8.
Kohler, et al., Continuous cultures of fused cells secreting antibody of predefined specificity, Nature, 1975, vol. 256:495-497.
Kohler, Immunoglobulin chain loss in hybridoma lines, Proc. Natl. Acad. Sci. USA , 1980, vol. 77(4):2197-2199.
Kozbor, A Human Hybrid Myeloma for Production of Human Monoclonal Antibodies1, Immunol. 1984, vol. 133 (6):3001-3005.
Lafranc, et al, IMGT unique numbering for immunoglobulin and T cell receptor variable domains and Ig superfamily V-like domains, Dev. Comp. Immunol., 2003, vol. 27(I):55-77.
Lam et al., Microencapsulation of Recombinant Humanized Monoclonal Antibody for Local Delivery, Proc. Int'l. Symp. Control Rel. Bioact. Mater., 1997, vol. 24: 759-760.
Lamers et al., Treatment of metastatic renal cell carcinoma (mRCC) with CAIX CAR-engineered T-cells—a completed study overview, Biochem Soc Trans, 2016, vol. 44, pt3:951-959.
Langer and Peppas, Chemical and Physical Structure of Polymers as Carriers for Controlled Release of Bioactive Agents: A Review, J. Macromol. Sci. Rev. Macromol. Chem., 1983, vol. 23: 61-126.
Langer, New Methods of Drug Delivery, Science, 1990, vol. 249:1527-1533.
Latchman, et al. PD-L2 is a second ligand for PD-1 and inhibits T cell activation. Nat Immunol. 2001; vol. 2(3):261-268. doi:10.1038/85330.
Lazar et al., A molecular immunology approach to antibody humanization and functional optimization, Mol. Immunol., 2007, vol. 44:1986-98.
Lee et al., Crystal structure of PD-1 in complex with an antibody-drug tislelizumab used in tumor immune checkpoint therapy. Biochem Biophys Res Commun. 2020;527(1):226-231. doi:10.1016/j.bbrc.2020.04.121.
Levy et al., Inhibition of Calcification of Bioprosthetic Heart Valves by Local Controlled-Release Diphosphonate, Science, 1985, vol. 228: 190-92.
Li et al., In Vivo Transfer of a Reporter Gene to the Retina Mediated by an Adenoviral Vector, Invest Opthalmol Vis Sci, 1994, vol. 35(5):2543-2549.
Li et al., Phenotype correction in retinal pigment epithelium in murine mucopolysaccharidosis VII by adenovirus-mediated gene transfer, PNAS, 1995, vol. 92:7700-7704.
Li et al., Recent updates in cancer immunotherapy: a comprehensive review and perspective of the 2018 China Cancer Immunotherapy Workshop in Beijing, J Hematol and Oncol, 2018, vol. 11, p. 1-15.
Li, et al., Human antibodies for immunotherapy development generated via a human B cell hybridoma technology, PNAS, 2006, vol. 103:3557-62.
Lin, et al. Regulatory mechanisms of PD-1/PD-L1 in cancers. Mol Cancer. 2024; vol. 23(108), p. 1-50. doi:10.1186/S12943-024-02023-W.
Liu et al., Poly(cationic lipid)-mediated in vivo gene delivery to mouse liver, Gene Therapy, 2003, vol. 10:180-187.
Louis et al., Antitumor activity and long-term fate of chimeric antigen eceptor-positive T cells in patients with neuroblastoma, Blood, 2011, vol. 118(23):6050-6056.
Lu, et al. PD-1 N58-Glycosylation-Dependent Binding of Monoclonal Antibody Cemiplimab for Immune Checkpoint Therapy. Front Immunol. 2022; vol. 13(826045), p. 1-11. doi:10.3389/fimmu.2022.826045.
Lund, et al. Multiple binding sites on the CH2 domain of IgG for mouse Fc gamma R11. Mol Immunol.(1):53-59. doi:10.1016/0161-5890(92)90156-R.
Ahmed et al., Human Epidermal Growth Factor Receptor 2 (HER2)-Specific Chimeric Antigen Receptor-Modified T Cells for the Immunotherapy of HER2-Positive Sarcoma, J Clin Oncol (2015), vol. 33(15), p. 688-1696.
Ahmed et al., Immunotherapy for Osteosarcoma: Genetic Modification of T cells Overcomes Low Levels of Tumor Antigen Expression, Mol Ther (2009), vol. 17(10):1779-1787.
Ali et al., Adeno-Associated Virus Gene Transfer to Mouse Retina, Hum Gene Ther, 1998, vol. 9:81-86.
Ali et al., Gene transfer into the mouse retina mediated by an adeno-associated viral vector, Hum Mol Genet, 1996, vol. 5(5):p. 591-594.
Altschul et al., Basic local alignment search tool, J. Mol. Biol., 1990, vol. 215:403-410.
Altschul, S. et al., Gapped BLAST and PSI-BLAST: a new generation of protein database search programs, Nucleic Acids Res., 1997, vol. 25, p. 3389-3402.
Ames, et al, Conversion of murine Fabs isolated from a combinatorial phage display library to full length immunoglobulins, Immunol. Methods, 1995, 184:177-86.
Amit et al., Three-dimensional structure of an antigen-antibody complex at 6 A resolution. Nature, 1985; vol. 313 (5998):156-158. doi:10.1038/313156A0.
Angal, et al., A single amino acid substitution abolishes the heterogeneity of chimeric mouse/human (IgG4) antibody. Mol Immunol. 1993;30(1):105-108. doi:10.1016/0161-5890(93)90432-B.
Baca, et al, Antibody Humanization Using Monovalent Phage Display*, J. Biol. Chem., 1997, 272:10678-10684.
Balazs et al., Liposomes for use in gene delivery, Journal of Drug Delivery. 2011, Art326497: p. 1-12.
Balciunas et al., Harnessing a High Cargo-Capacity Transposon for Genetic Applications in Vertebrates, PLoS Genet, Nov. 10, 2006;2(11):e169, 1715-1724. doi:10.1371/journal.pgen.0020169. Epub Aug. 28, 2006.
Bass, et al, Hormone phage: an enrichment method for variant proteins with altered binding properties, Proteins, 1990, 8:309-14.
Bennett et al., Real-Time, Noninvasive In Vivo Assessment of Adeno-Associated Virus-Mediated Retinal Transduction, Invest Opthalmol Vis Sci, 1997, vol. 38:2857-2863.
Bitter et al., Expression and secretion vectors for yeast, Methods in Enzymology, 1987, vol. 153:516-544.

(56) References Cited

OTHER PUBLICATIONS

Boerner, et al., Production of Antigen-Specific Human Monoclonal Antibodies from In Vitro-Primed Human Splenocytes, J. Immunol., 1991, 147(I):86-95.
Borras et al., Adenoviral reporter gene transfer to the human trabecular meshwork does not alter aqueous humor outflow. Relevance for potential gene therapy of glaucoma, Gene Ther, 1999, vol. 6:515-524.
Brinkman, et al, Phage display of disulfide-stabilized Fv fragments, J. Immunol. Methods, 1995, 182:41-50.
Brodeur, et al., Monoclonal Antibody Production Techniques and Applications, 1987, p. 51-63.
Brown et al. Assessing the binding properties of the anti-PD-1 antibody landscape using label-free biosensors, PLoS One. 2020;15(3), p. 1-21.
Brown et al., Bioactivity and Safety of IL13Rα2-Redirected Chimeric Antigen Receptor CD8+ T cells in Patients with Recurrent Glioblastoma, Clin Cancer Res (2015) 21(18):4062-4072.
Bruggemann and Taussing, Production of human antibody repertoires in transgenic mice, Curr. Opin. Biotechnol., 1997, 8(4):455-58.
Buchwald et al., Long-term, continuous intravenous heparin administration by an implantable infusion pump in ambulatory patients with recurrent venous thrombosis, Surgery, 1980, vol. 88, Issue 4: 507-816.
Burton et al., Human Antibodies from Combinatorial Libraries, Advances in Immunology, 1994, 57:191-280.
Caldas, et al, Design and synthesis of germline-based hemi-humanized single-chain Fv against the CD18 surface antigen, Protein Eng., 2000, 13(5):353-360.
Carreno BM, Collins M. The B7 family of ligands and its receptors: new pathways for costimulation and inhibition of immune responses. Annu Rev Immunol. 2002;20:29-53. doi:10.1146/ANNUREV.IMMUNOL.20.091101.091806.
Carter et al, Humanization of an anti-p185HER2 antibody for human cancer therapy, Proc. Natl. Acad. Sci. USA, 1992, 89:4285-4289.
Caruana et al., Heparanase promotes tumor infiltration and antitumor activity of CAR-redirected T-lymphocytes, Nat Med (2015) 21(5):524-529.
Castellano et al., Discovery and characterization of two anti-PD-1 antibodies with a unique binding mechanism to human PD-1, MABS, 2025, vol. 17(1), p. 1-18.
Chao, et al, Isolating and engineering human antibodies using yeast surface display, Nature Protocols, 2006, vol. 1(2): 755-768.
Chen, et al. The role of PD-1 signaling in health and immune-related diseases. Front Immunol. 2023; vol. 14:1163633, p. 1-13. doi:10.3389/FIMMU.2023.1163633.
Cheng, et al. Structure and Interactions of the Human Programmed Cell Death 1 Receptor. Journal of Biological Chemistry. 2013; vol. 288(17):p. 11771-11785. doi:10.1074/jbc.M112.448126.
Chothia et al., Canonical Structures for the Hypervariable Regions of Immunoglobulins, J. Mol. Biol., 1987, 196:901-17.
Ciesielska-Figlon et al., The Role of the CD28 Family Receptors in T-Cell Immunomodulation. Int J Mol Sci. 2024;25 (2), p. 1-14. doi:10.3390/IJMS25021274.
Cleek et al., Biodegradable Polymeric Carriers for a bFGF Antibody for Cardiosvascular Application, Pro. Int'l. Symp. Control. Rel. Bioact. Mater., 1997, vol. 24: 853-54.
Cole, et al., The EBV-Hybridoma Technique and its Application to Human Lung Cancer, Monoclonal Antibodies and Cancer Therapy, 1985, p. 77-96.
Couto, et al, Anti-BA46 Monoclonal Antibody Mc3: Humanization Using a Novel Positional Consensus and in Vivo and in Vitro Characterization, Cancer Res., 1995, 55: 1717-22.
Couto, et al, Designing Human Consensus Antibodies with Minimal Positional Templates, Cancer Res., 1995, 55 (23 Supp):5973s-5977s.
Cross-Linking Mass Spectrometry (XL-MS). Accessed Feb. 3, 2025, downloaded Nov. 18, 2025; https://covalx.com/services/epitope-mapping-xl-ms/.
Dall'Acqua et al, Antibody humanization by framework shuffling, Methods, 2005, vol. 36:43-60.
Damschroder, et al., Framework shuffling of antibodies to reduce immunogenicity and manipulate functional and biophysical properties, Mol. Immunol., 2007, 44:3049-60.
De Groot, et al., Evolutionary deimmunization: An ancillary mechanism for self-tolerance?, Cell. Immunol., 2006, 244:148-153.
DeSousa, et al. Therapeutic PD-L1 antibodies are more effective than PD-1 antibodies in blocking PD-1/PD-L1 signaling. Sci Rep. 2019; vol. 9:11472, p. 1-9. doi:10.1038/s41598-019-47910-1.
Dondelinger et al., Understanding the Significance and Implications of Antibody Numbering and Antigen-Binding Surface/Residue Definition. Front Immunol. Oct. 16, 2018;vol. 9:2278,p. 1-15.
Dong et al., B7-H1, a third member of the B7 family, co-stimulates T-cell proliferation and interleukin-10 secretion. Nat Med. 1999;5(12):1365-1369. doi:10.1038/70932.
Dufner, et al, Harnessing phage and ribosome display for antibody optimisation, Trends Biotechnol., 2006, vol. 24 (11):523-529.
During et al., Controlled Releaese of Dopamine from a Polymeric Brain Implant: In Vivo Characterization, Ann. Neurol., 1989, vol. 25:351-356.
Feldhaus, et al., Flow-cytometric isolation of human antibodies from a nonimmune *Saccharomyces cerevisiae* surface display library, Nat. Biotechnol, 2003, vol. 21:163-170.
Flannery et al., Efficient photoreceptor-targeted gene expression in vivo by recombinant adeno-associated virus, PNAS, 1997, vol. 94:6916-6921.
Flotte et al., Stable in Vivo expression of the cystic fibrosis transmembrane conductance regulator with an adeno-associated virus vector, PNAS, 1993, vol. 90:10613-10617.
Search Report and Written Opinion for PCTUS2556530 mailed Mar. 17, 2026.

* cited by examiner

FIG. 3

```
                        1       10        20        30        40        50        60        70        80        90        100
                        ....|....|....|....|....|....|....|....|....|....|....|....|....|....|....|....|....|....|....|....|....|..
              Kabat                            -----------               -------                                ---------
              IMGT                                ------                 ---                                    ---------
              Chotia                           -----------               -------                                ---------
SEQ ID NO: 20 UDIZ-008L DIQMTQSPSSLSASVGDRVTITCRASQSISSYLNWYQQKPGKAPKLLIYAASSLQSGVPSRFSGSGSGTDFTLTISSLQPEDFATYYCQQSYDLPYTFGQGTKVEIK

                        1       10        20        30        40        50        60        70        80        90        100       110
                        ....|....|....|....|....|....|....|....|....|....|....|....|....|....|....|....|....|....|....|....|....|....|....|...
              Kabat                                   -----              -----------------                                ---------
              IMGT                             --------                 --------                                      -----------
              Chotia                           -------                    ------                                         ---------
SEQ ID NO: 19 UDIZ-008H EVQLLESGGGLVQPGGSLRLSCAASGFTFNNYAMSWVRQAPGKGLEWVSSITGSGSTTYYADSVKGRFTISRDNSKNTLYLQMNSLRAEDTAVYYCASPYSVGYFDYWGQGTLVTVSS
```

| UDIZ-007 | | |
|---|---|---|
| Spike | Molecular weight (kDa) | Purity (%monomer) |
| 1 | 498.41 | 0.14 |
| 2 | 375.14 | 0.24 |
| 3 | **171.91** | **99.62** |

| UDIZ-008 | | |
|---|---|---|
| Spike | Molecular weight (kDa) | Purity (%monomer) |
| 1 | 396.6 | 1.45 |
| 2 | **167.59** | **98.55** |

UDIZ-007

| Antibody /target | ka (1/Ms) | kd (1/s) | KD (nM) |
|---|---|---|---|
| UDIZ-007 / hPD-1 | $6.0 \times 10^5$ | $2.1 \times 10^{-3}$ | 3.5 |

| Antibody / target | ka (1/Ms) | kd (1/s) | KD (nM) |
|---|---|---|---|
| UDIZ-008/ hPD-1 | $8.6 \times 10^5$ | $2.4 \times 10^{-3}$ | 2.8 |

| Antibody / target | ka (1/Ms) | kd (1/s) | KD (nM) |
|---|---|---|---|
| UDIZ-007/ cPD-1 | $1.7 \times 10^5$ | $3.6 \times 10^{-3}$ | 21.5 |

| Antibody / target | ka (1/Ms) | kd (1/s) | KD (nM) |
|---|---|---|---|
| UDIZ-008/ CPD-1 | $1.3 \times 10^5$ | $5.0 \times 10^{-3}$ | 38.5 |

| Antibody | hPD-1 EC$_{50}$ (µg/mL) |
|---|---|
| UDIZ-007 | 0.0069 |
| Keytruda® | 0.0099 |

| Antibody | hPD-1 EC$_{50}$ (μg/mL) |
|---|---|
| UDIZ-008 | 0.0275 |
| Keytruda® | 0.0057 |

FIG. 10A
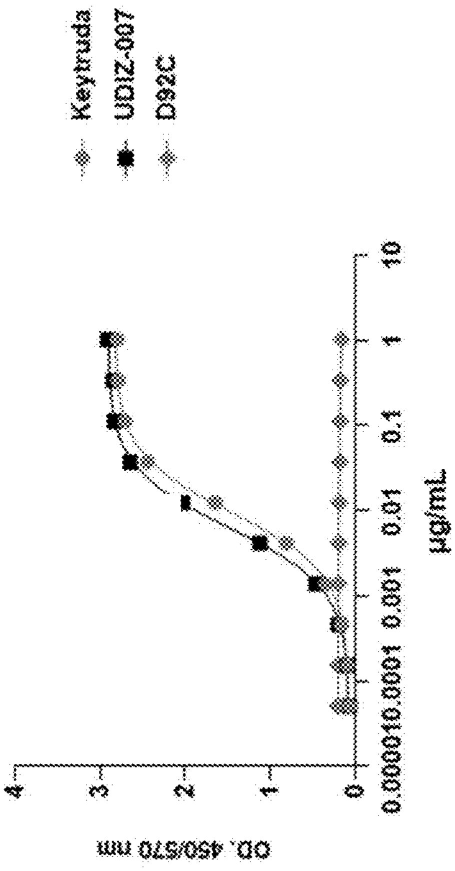
FIG. 10B
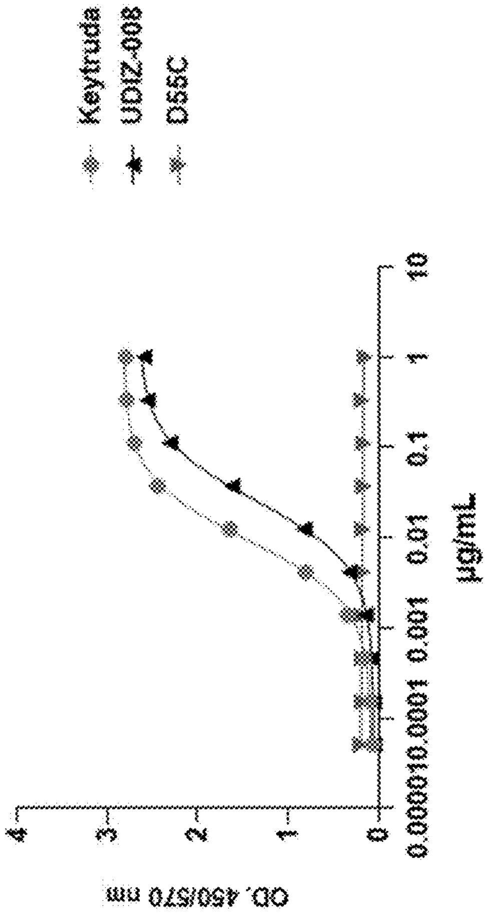
FIG. 10C
| Antibody | cPD-1 $EC_{50}$ (µg/mL) |
|---|---|
| UDIZ-007 | 0.0063 |
| UDIZ-008 | 0.0254 |
| Keytruda® | 0.0094 |

FIG. 11A
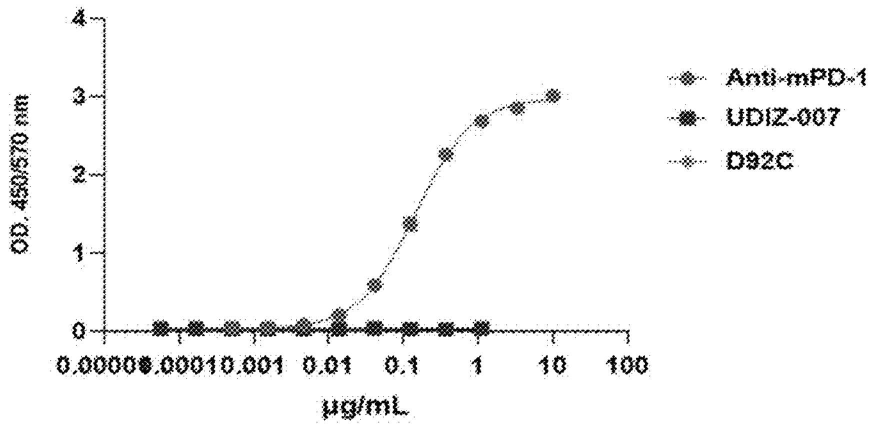
FIG. 11B
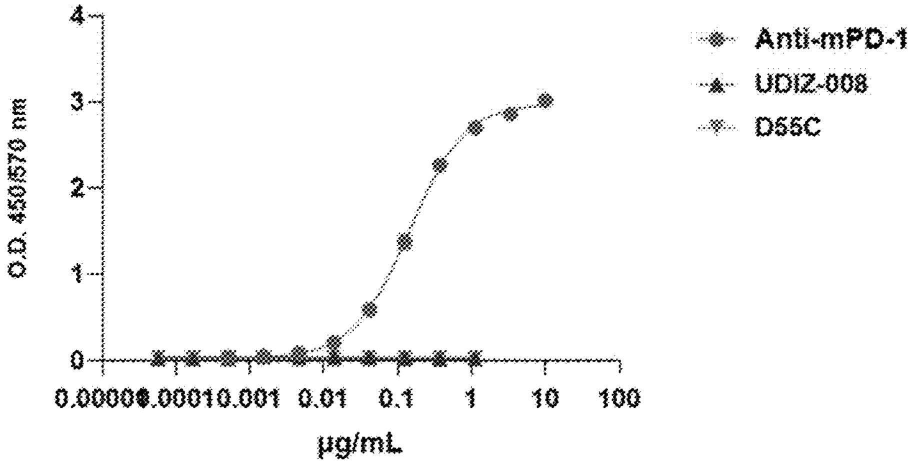
FIG. 11C
| Antibody | mPD-1 $EC_{50}$ (µg/mL) |
|---|---|
| UDIZ-007 | --- |
| UDIZ-008 | --- |
| Anti-mPD-1 | 0.1439 |

FIG. 12A
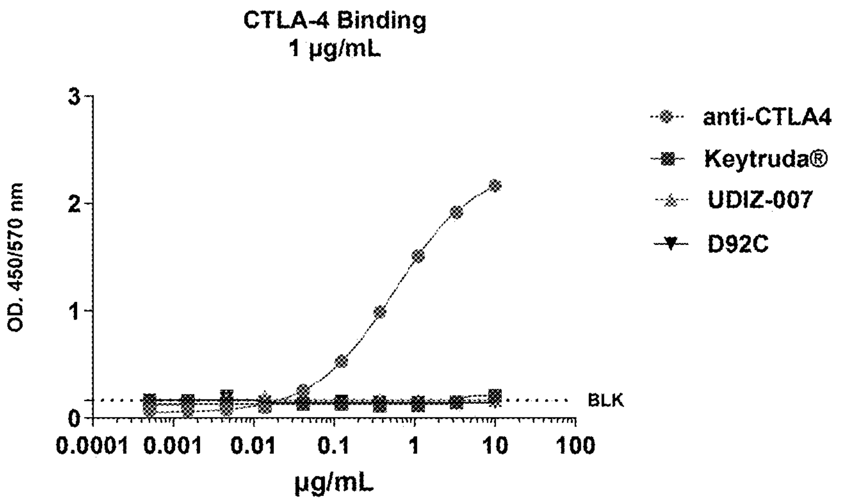
FIG. 12B
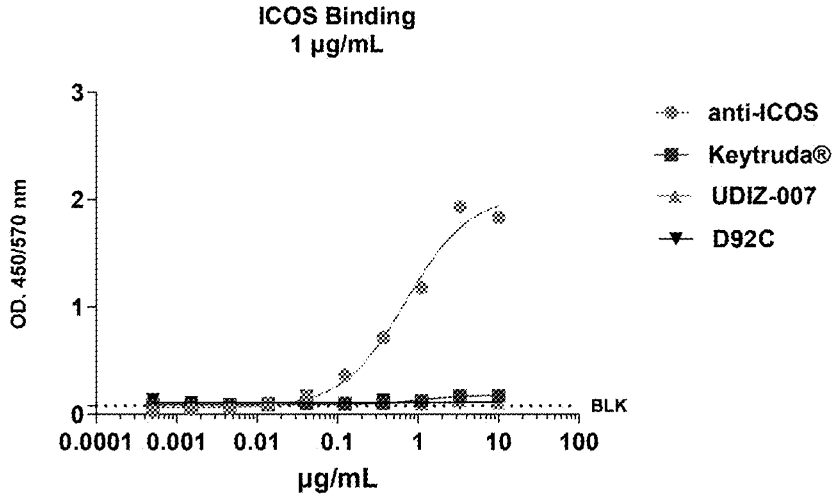
FIG. 12C
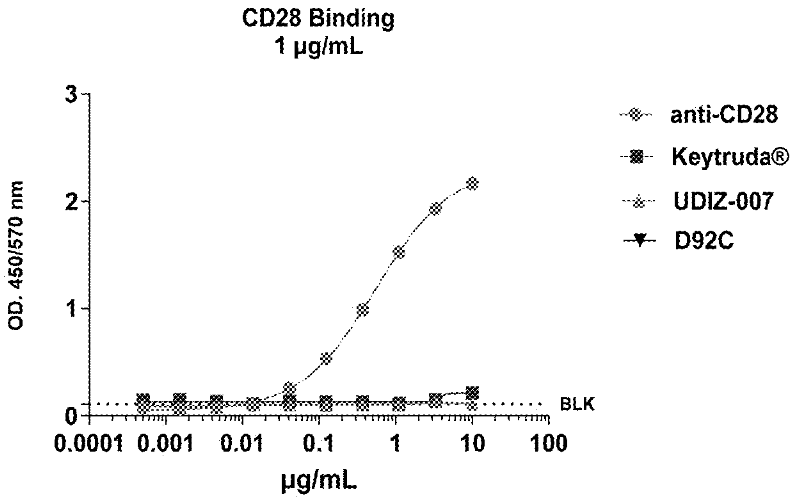
FIG. 12D
| Antibody | $EC_{50}$ (µg/mL) |
|---|---|
| UDIZ-007 | --- |
| Anti-CTLA-4 | 0.5664 |
| Anti-ICOS | 0.7069 |
| Anti-CD28 | 0.5493 |
| Keytruda® | --- |

FIG. 13A
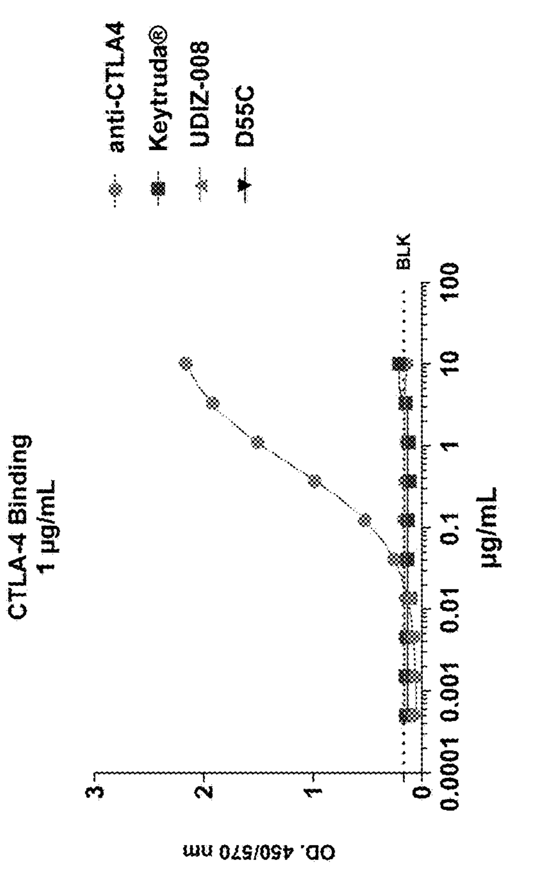
FIG. 13B
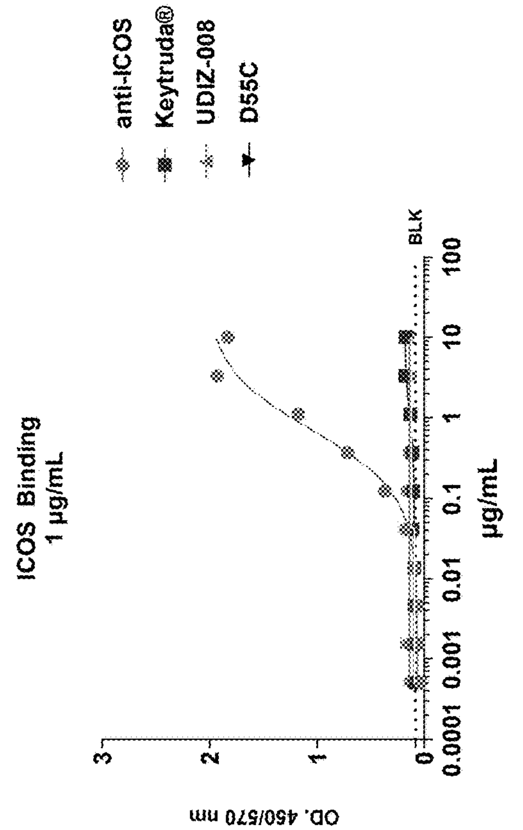
FIG. 13C
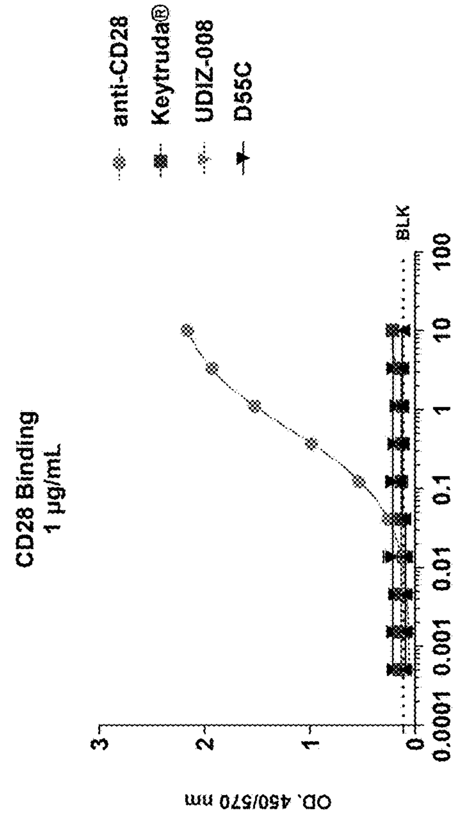
FIG. 13D
| Antibody | $EC_{50}$ (µg/mL) |
|---|---|
| UDIZ-008 | --- |
| Anti-CTLA-4 | 0.5664 |
| Anti-ICOS | 0.7069 |
| Anti-CD28 | 0.5493 |
| Keytruda® | --- |

FIG. 14A
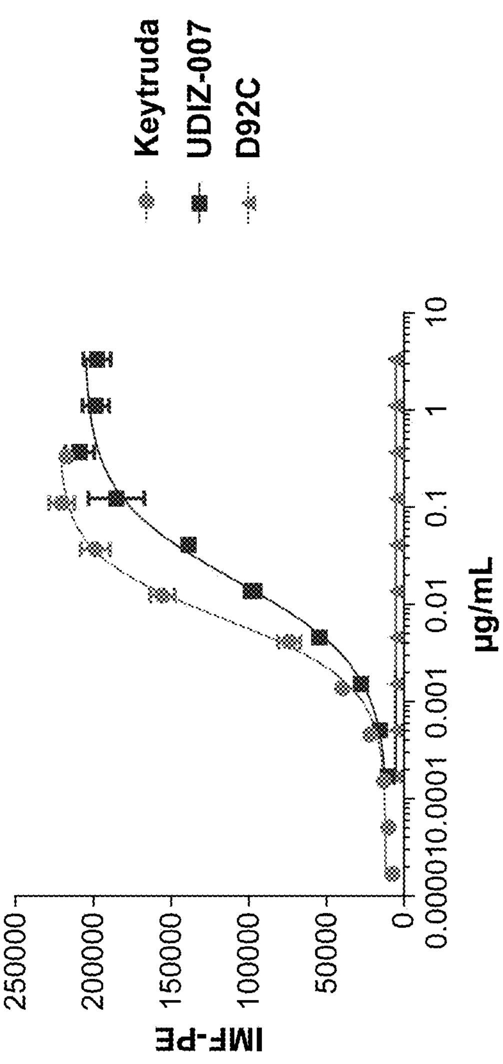
FIG. 14B
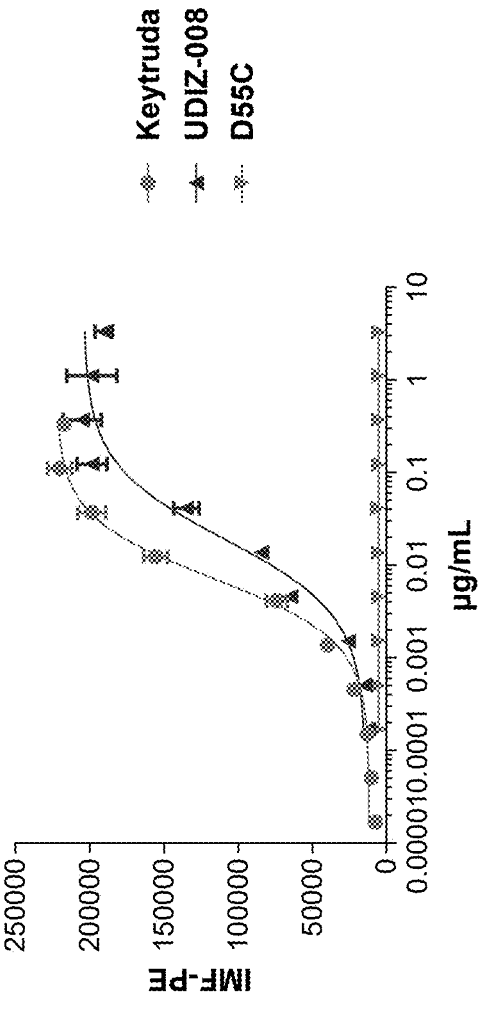
FIG. 14C
| Antibody | $EC_{50}$ (μg/mL) |
|---|---|
| UDIZ-007 | 0.0174 |
| UDIZ-008 | 0.0191 |
| Keytruda ® | 0.0072 |

FIG. 15A
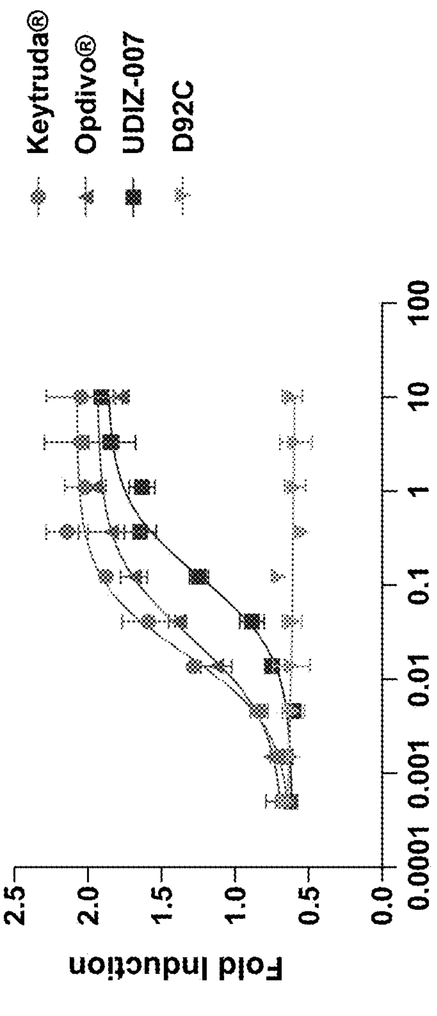
FIG. 15B
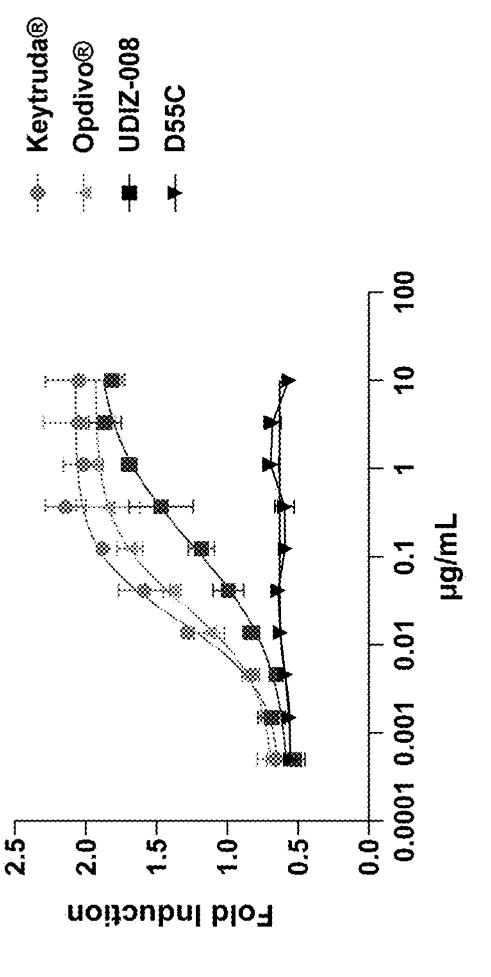
FIG. 15C
| Antibody | $EC_{50}$ (μg/mL) |
|---|---|
| UDIZ-007 | 0.1229 |
| UDIZ-008 | 0.1372 |
| Keytruda® | 0.0189 |
| Opdivo® | 0.0277 |

| Antibody /target | ka (1/Ms) | kd (1/s) | KD (nM) |
|---|---|---|---|
| UDIZ-007 / FcRn | $1.2 \times 10^5$ | $7.8 \times 10^{-2}$ | 665 |

| Antibody /target | ka (1/Ms) | kd (1/s) | KD (nM) |
|---|---|---|---|
| UDIZ-008 / FcRn | $1.3 \times 10^{10}$ | $1.8 \times 10^{3}$ | 138.5 |

FIG. 19A
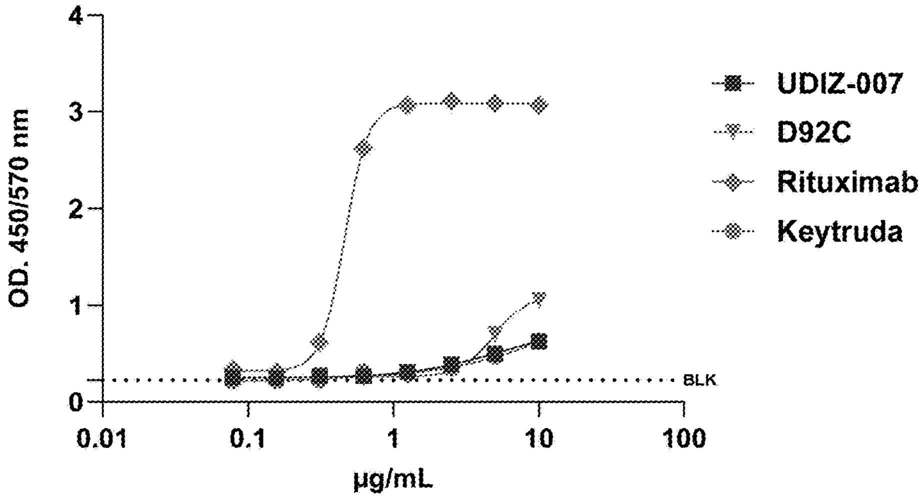
FIG. 19B
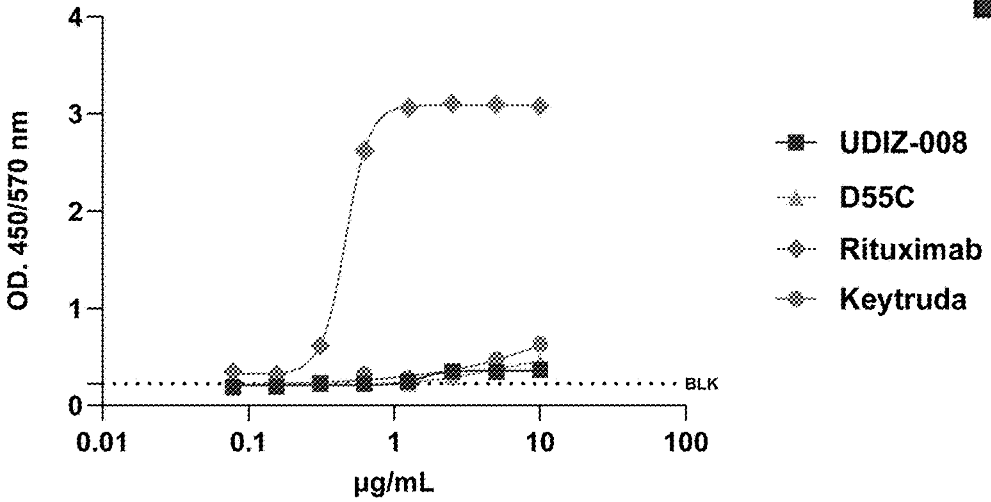
FIG. 19C
| Antibody | $EC_{50}$ (µg/mL) |
|---|---|
| UDIZ-007 | --- |
| UDIZ-008 | --- |
| Keytruda® | --- |
| Rituximab (MabThera®) | 5.362 |

FIG. 20

| hDP-1 fragment | UDIZ-007 | Enzyme |
|---|---|---|
| AAFPEDRSQPGQDCRFR | HCDR3 | Thermolysin |
| AAFPEDRSQPGQDCR | HCDR2 | Thermolysin |
| AAFPEDRSQPGQDCRFR | HCDR2 | Thermolysin |
| YRMSPSNQTDKLAAFPEDRSQPG QDCRF | HCDR1 | Chymotrypsin |
| QPGQDCRFRV | HCDR1 | Elastase |
| QPGQDCRFRV | HCDR2 | Elastase |
| VTQLPNGRDFHMSVVR | HCDR2 | Trypsin |
| RVTQLPNGRDF | HCDR2 | Chymotrypsin |
| HMSVVRARRNDSGTY | HCDR2 | Chymotrypsin |
| FHMSV | LCDR1 | Thermolysin |
| DFHMSVVRARR | LCDR2 | Trypsin |
| DFHMSVVRARR | LCDR2 | Trypsin |
| DFHMSVVRARR | LCDR2 | Trypsin |

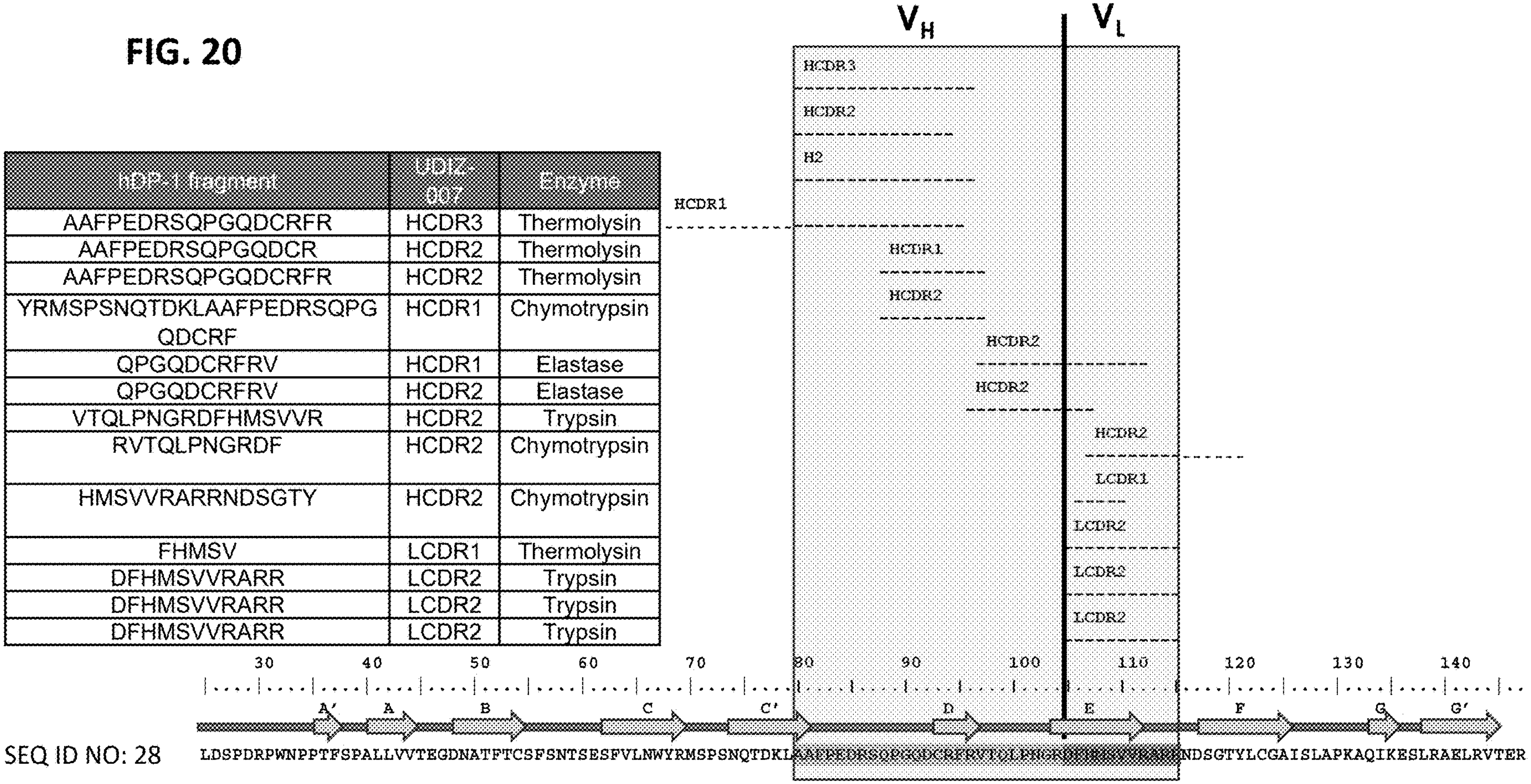

SEQ ID NO: 28

| UDIZ-007 Formulated | | |
|---|---|---|
| Spike | Molecular weight (kDa) | Purity (% monomer) |
| 1 | 504.78 | 0.16 |
| 2 | 173.41 | 99.84 |

| Antibody | $EC_{50}$ (μg/mL) |
|---|---|
| Keytruda® | 0.0102 |
| UDIZ-007 PBS pH 7.4 | 0.0070 |
| UDIZ-007 Formulated pH 6.0 | 0.0071 |
| Negative control | --- |

| Antibody | $EC_{50}$ (µg/mL) |
|---|---|
| Keytruda® | 0.0113 |
| UDIZ-007 T0 | 0.0064 |
| UDIZ-007_5 freeze/thaw (1) | 0.0052 |
| UDIZ-007_5 freeze/thaw (2) | 0.0036 |
| Formulation blank | --- |

| Antibody | $EC_{50}$ (μg/mL) |
|---|---|
| Keytruda® | 0.0102 |
| UDIZ-007 T0 | 0.0070 |
| UDIZ-007 Photostability 16h (1) | 0.0060 |
| UDIZ-007 Photostability 16h (2) | 0.0045 |
| Negative control | --- |

SEQUENCE LISTING

```
Sequence total quantity: 29
SEQ ID NO: 1             moltype = AA  length = 5
FEATURE                  Location/Qualifiers
source                   1..5
                         mol_type = protein
                         organism = synthetic construct
SEQUENCE: 1
NYAMS                                                                  5

SEQ ID NO: 2             moltype = AA  length = 17
FEATURE                  Location/Qualifiers
source                   1..17
                         mol_type = protein
                         organism = synthetic construct
SEQUENCE: 2
SITGSGSTTY YADSVKG                                                     17

SEQ ID NO: 3             moltype = AA  length = 9
FEATURE                  Location/Qualifiers
source                   1..9
                         mol_type = protein
                         organism = synthetic construct
SEQUENCE: 3
PYSVGYFDY                                                              9

SEQ ID NO: 4             moltype = AA  length = 11
FEATURE                  Location/Qualifiers
source                   1..11
                         mol_type = protein
                         organism = synthetic construct
SEQUENCE: 4
RASQSISSYL N                                                           11
```

```
SEQ ID NO: 5            moltype = AA  length = 7
FEATURE                 Location/Qualifiers
source                  1..7
                        mol_type = protein
                        organism = synthetic construct
SEQUENCE: 5
AASSLQS                                                            7

SEQ ID NO: 6            moltype = AA  length = 9
FEATURE                 Location/Qualifiers
source                  1..9
                        mol_type = protein
                        organism = synthetic construct
SEQUENCE: 6
QQSYDLPYT                                                          9

SEQ ID NO: 7            moltype = AA  length = 8
FEATURE                 Location/Qualifiers
source                  1..8
                        mol_type = protein
                        organism = synthetic construct
SEQUENCE: 7
GFTFNNYA                                                           8

SEQ ID NO: 8            moltype = AA  length = 8
FEATURE                 Location/Qualifiers
source                  1..8
                        mol_type = protein
                        organism = synthetic construct
SEQUENCE: 8
ITGSGSTT                                                           8

SEQ ID NO: 9            moltype = AA  length = 11
FEATURE                 Location/Qualifiers
source                  1..11
                        mol_type = protein
                        organism = synthetic construct
SEQUENCE: 9
ASPYSVGYFD Y                                                       11

SEQ ID NO: 10           moltype = AA  length = 6
FEATURE                 Location/Qualifiers
source                  1..6
                        mol_type = protein
                        organism = synthetic construct
SEQUENCE: 10
QSISSY                                                             6

SEQ ID NO: 11           moltype =   length =
SEQUENCE: 11
000

SEQ ID NO: 12           moltype = AA  length = 9
FEATURE                 Location/Qualifiers
source                  1..9
                        mol_type = protein
                        organism = synthetic construct
SEQUENCE: 12
QQSYDLPYT                                                          9

SEQ ID NO: 13           moltype = AA  length = 7
FEATURE                 Location/Qualifiers
source                  1..7
                        mol_type = protein
                        organism = synthetic construct
SEQUENCE: 13
GFTFNNY                                                            7

SEQ ID NO: 14           moltype = AA  length = 6
FEATURE                 Location/Qualifiers
source                  1..6
                        mol_type = protein
                        organism = synthetic construct
SEQUENCE: 14
TGSGST                                                             6

SEQ ID NO: 15           moltype = AA  length = 9
FEATURE                 Location/Qualifiers
```

```
source                  1..9
                        mol_type = protein
                        organism = synthetic construct
SEQUENCE: 15
PYSVGYFDY                                                   9

SEQ ID NO: 16           moltype = AA  length = 11
FEATURE                 Location/Qualifiers
source                  1..11
                        mol_type = protein
                        organism = synthetic construct
SEQUENCE: 16
RASQSISSYL N                                                11

SEQ ID NO: 17           moltype = AA  length = 7
FEATURE                 Location/Qualifiers
source                  1..7
                        mol_type = protein
                        organism = synthetic construct
SEQUENCE: 17
AASSLQS                                                     7

SEQ ID NO: 18           moltype = AA  length = 9
FEATURE                 Location/Qualifiers
source                  1..9
                        mol_type = protein
                        organism = synthetic construct
SEQUENCE: 18
QQSYDLPYT                                                   9

SEQ ID NO: 19           moltype = AA  length = 118
FEATURE                 Location/Qualifiers
source                  1..118
                        mol_type = protein
                        organism = synthetic construct
SEQUENCE: 19
EVQLLESGGG LVQPGGSLRL SCAASGFTFN NYAMSWVRQA PGKGLEWVSS ITGSGSTTYY  60
ADSVKGRFTI SRDNSKNTLY LQMNSLRAED TAVYYCASPY SVGYFDYWGQ GTLVTVSS    118

SEQ ID NO: 20           moltype = AA  length = 107
FEATURE                 Location/Qualifiers
source                  1..107
                        mol_type = protein
                        organism = synthetic construct
SEQUENCE: 20
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYDLPYTFGQ GTKVEIK                107

SEQ ID NO: 21           moltype = AA  length = 444
FEATURE                 Location/Qualifiers
source                  1..444
                        mol_type = protein
                        organism = synthetic construct
SEQUENCE: 21
EVQLLESGGG LVQPGGSLRL SCAASGFTFN NYAMSWVRQA PGKGLEWVSS ITGSGSTTYY  60
ADSVKGRFTI SRDNSKNTLY LQMNSLRAED TAVYYCASPY SVGYFDYWGQ GTLVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFEGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLG                                         444

SEQ ID NO: 22           moltype = AA  length = 214
FEATURE                 Location/Qualifiers
source                  1..214
                        mol_type = protein
                        organism = synthetic construct
SEQUENCE: 22
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYDLPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 23           moltype = AA  length = 447
FEATURE                 Location/Qualifiers
source                  1..447
                        mol_type = protein
                        organism = synthetic construct
```

-continued

```
SEQUENCE: 23
EVQLLESGGG LVQPGGSLRL SCAASGFTFN NYAMSWVRQA PGKGLEWVSS ITGSGSTTYY  60
ADSVKGRFTI SRDNSKNTLY LQMNSLRAED TAVYYCASPY SVGYFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                      447

SEQ ID NO: 24          moltype = AA  length = 214
FEATURE                Location/Qualifiers
source                 1..214
                       mol_type = protein
                       organism = synthetic construct
SEQUENCE: 24
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYDLPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 25          moltype = AA  length = 288
FEATURE                Location/Qualifiers
source                 1..288
                       mol_type = protein
                       organism = Homo sapiens
SEQUENCE: 25
MQIPQAPWPV VWAVLQLGWR PGWFLDSPDR PWNPPTFSPA LLVVTEGDNA TFTCSFSNTS  60
ESFVLNWYRM SPSNQTDKLA AFPEDRSQPG QDCRFRVTQL PNGRDFHMSV VRARRNDSGT  120
YLCGAISLAP KAQIKESLRA ELRVTERRAE VPTAHPSPSP RPAGQFQTLV VGVVGGLLGS  180
LVLLVWVLAV ICSRAARGTI GARRTGQPLK EDPSAVPVFS VDYGELDFQW REKTPEPPVP  240
CVPEQTEYAT IVFPSGMGTS SPARRGSADG PRSAQPLRPE DGHCSWPL                288

SEQ ID NO: 26          moltype = AA  length = 25
FEATURE                Location/Qualifiers
source                 1..25
                       mol_type = protein
                       organism = Homo sapiens
SEQUENCE: 26
AAFPEDRSQP GQDCRFRVTQ LPNGR                                        25

SEQ ID NO: 27          moltype = AA  length = 11
FEATURE                Location/Qualifiers
source                 1..11
                       mol_type = protein
                       organism = Homo sapiens
SEQUENCE: 27
DFHMSVVRAR R                                                       11

SEQ ID NO: 28          moltype = AA  length = 123
FEATURE                Location/Qualifiers
source                 1..123
                       mol_type = protein
                       organism = Homo sapiens
SEQUENCE: 28
LDSPDRPWNP PTFSPALLVV TEGDNATFTC SFSNTSESFV LNWYRMSPSN QTDKLAAFPE  60
DRSQPGQDCR FRVTQLPNGR DFHMSVVRAR RNDSGTYLCG AISLAPKAQI KESLRAELRV  120
TER                                                                123

SEQ ID NO: 29          moltype = AA  length = 36
FEATURE                Location/Qualifiers
source                 1..36
                       mol_type = protein
                       organism = Homo sapiens
SEQUENCE: 29
AAFPEDRSQP GQDCRFRVTQ LPNGRDFHMS VVRARR                            36
```

ANTI-PD-1 ANTIBODIES AND METHODS OF USE

CROSS-REFERENCE TO RELATED APPLICATIONS

This application claims the benefit of and priority to U.S. Application No. 63/723,959, filed Nov. 22, 2024, U.S. Provisional Application No. 63/762,358, filed Feb. 24, 2025, and U.S. Provisional Application No. 63/837,208, filed Jul. 2, 2025, the entire contents of each of which are incorporated herein by reference.

SEQUENCE LISTING

The instant application contains a Sequence Listing which has been submitted electronically in XML format and is hereby incorporated by reference in its entirety. Said XML copy, created on Nov. 19, 2025, is named 232406-010404_ST26.xml and is 27,334 bytes in size.

FIELD

The present disclosure generally relates to antibodies against the programmed cell death protein 1 (PD-1) and derivatives thereof. The present disclosure also generally relates to use of such antibodies for treating cancer.

BACKGROUND

PD-1 a is a receptor expressed on immune cells that serves to maintain peripheral tolerance by inhibiting T cell activation, upon binding to either PD-L1 or PD-L2 ligands. Tumor cells express PD-L1, and to a lesser extent PD-L2, using PD-L1/L2 as a molecular shield to attenuate T-cell mediated cytotoxicity and thereby evade immune surveillance. Therefore, there is a need in the art to develop effective antibody-based approaches for blocking the PD-1:PD-L1 interaction and/or the PD-1:PD-L2 interaction to enhance current cancer treatments.

SUMMARY

In one aspect, the disclosure provides a binding molecule that binds to programmed cell death protein 1 (PD-1). In some embodiments, the binding molecule comprises (a) a variable heavy chain CDR1 (HCDR1) comprising an amino acid sequence of SEQ ID NO: 1 or a HCDR1 having one to two amino acid substitutions as compared to the sequence of SEQ ID NO: 1; (b) a variable heavy chain CDR2 (HCDR2) comprising an amino acid sequence of SEQ ID NO: 2 or a HCDR2 having one to two amino acid substitutions as compared to the sequence of SEQ ID NO: 2; and (c) a variable heavy chain CDR3 (HCDR3) comprising an amino acid sequence of SEQ ID NO: 3 or a HCDR3 having one to two amino acid substitutions as compared to the sequence of SEQ ID NO: 3, wherein the binding molecule is numbered with reference to the Kabat numbering system. In some embodiments, the binding molecule comprises a variable light chain CDR1 (LCDR1) comprising an amino acid sequence of SEQ ID NO: 4 or a LCDR1 having one to two amino acid substitutions as compared to the sequence of SEQ ID NO: 4; a variable light chain CDR2 (LCDR2) comprising an amino acid sequence of SEQ ID NO: 5 or a LCDR2 having one to two amino acid substitutions as compared to the sequence of SEQ ID NO: 5; and a variable light chain CDR3 (LCDR3) comprising an amino acid sequence of SEQ ID NO: 6 or a LCDR3 having one to two amino acid substitutions as compared to the sequence of SEQ ID NO: 6, wherein the binding molecule is numbered with reference to the Kabat numbering system. In some embodiments, the binding molecule comprises: (a) a variable heavy chain CDR1 (HCDR1) comprising an amino acid sequence of SEQ ID NO: 1; (b) a variable heavy chain CDR2 (HCDR2) comprising an amino acid sequence of SEQ ID NO: 2; (c) a variable heavy chain CDR3 (HCDR3) comprising an amino acid sequence of SEQ ID NO: 3; (d) a variable light chain CDR1 (LCDR1) comprising an amino acid sequence of SEQ ID NO: 4; (e) a variable light chain CDR2 (LCDR2) comprising an amino acid sequence of SEQ ID NO: 5; and (f) a variable light chain CDR3 (LCDR3) comprising an amino acid sequence of SEQ ID No: 6; and wherein the binding molecule is numbered with reference to the Kabat numbering system. In some embodiments, the binding molecule binds to residues 80-115 (SEQ ID NO: 29) of human PD-1 when numbered in accordance with SEQ ID NO: 25. In some embodiments, the binding molecule binds to residues 80-104 (SEQ ID NO: 26) and 105-115 (SEQ ID NO: 27) of human PD-1 when numbered in accordance with SEQ ID NO: 25. In some embodiments, the binding molecule comprises a heavy chain variable domain (VH) comprising an amino acid sequence that is at least 85% identical to SEQ ID NO: 19, and a light chain variable domain (VL) comprising an amino acid sequence that is at least 85% identical to SEQ ID NO: 20. In some embodiments, the binding molecule comprises a VH comprising an amino acid sequence of SEQ ID NO: 19, and a VL comprising an amino acid sequence of SEQ ID No: 20.

In some embodiments, the binding molecule is a monoclonal antibody or antigen-binding fragment thereof. In some embodiments, the binding molecule is a fully human monoclonal antibody or antigen-binding fragment. In some embodiments, the monoclonal antibody or antigen-binding fragment thereof comprises an IgG isotype selected from the group consisting of IgG1, IgG2, IgG3, IgG4, and a variant thereof. In some embodiments, the binding molecule is a fully human monoclonal antibody comprising an IgG4-PE. In some embodiments, the binding molecule comprises a heavy chain comprising an amino acid sequence that is at least about 85% identical to SEQ ID NO: 21, and a light chain comprising an amino acid sequence that is at least about 85% identical to SEQ ID NO: 22. In some embodiments, the binding molecule comprises a heavy chain comprising an amino acid sequence of SEQ ID NO: 21, and a light chain comprising an amino acid sequence of SEQ ID NO: 22. In some embodiments, the binding molecule is a fully human monoclonal antibody comprising an IgG1-LALA. In some embodiments, the binding molecule comprises a heavy chain comprising an amino acid sequence that is at least about 85% identical to SEQ ID NO: 23, and a light chain comprising an amino acid sequence that is at least about 85% identical to SEQ ID NO: 24. In some embodiments, the binding molecule comprises a heavy chain comprising an amino acid sequence of SEQ ID NO: 23, and a light chain comprising an amino acid sequence of SEQ ID NO: 24.

In some embodiments, the binding molecule blocks the interaction between PD-1 and programmed cell death ligand 1 (PD-L1) and between PD-1 and programmed cell death ligand 2 (PD-L2). In some embodiments, the binding molecule activates the immune system.

In some aspects, the disclosure provides a binding molecule that binds to residues 80-115 (SEQ ID NO: 29) of human PD-1 when numbered in accordance with SEQ ID NO: 25. In some embodiments, the binding molecule binds to residues 80-104 (SEQ ID NO: 26) and 105-115 (SEQ ID NO: 27) of human PD-1 when numbered in accordance with SEQ ID NO: 25.

In another aspect, the disclosure provides a polynucleotide encoding the binding molecule described herein.

In another aspect, the disclosure provides a vector, comprising the polynucleotide described herein.

In another aspect, the disclosure provides a pharmaceutical composition comprising the binding molecule described herein, the polynucleotide described herein, or the vector described herein. In some embodiments, the pharmaceutical composition further comprises a pharmaceutically acceptable carrier. In some embodiments, the pH of the pharmaceutical composition is about 4.0 to about 8.0. In some embodiments, the pH of the pharmaceutical composition is about 6.0. In some embodiments, the binding molecule is present at a concentration of about 1 mg/mL to about 100 mg/mL. In some embodiments, the binding molecule is present at a concentration of about 31 mg/mL. In some embodiments, L-histidine is present at a concentration of about 0.5 mg/mL to about 1 mg/mL. In some embodiments, L-histidine is present at a concentration of about 0.76 mg/mL. In some embodiments, L-histidine monohydrate is present at a concentration of about 1 mg/mL to about 2 mg/mL. In some embodiments, L-histidine monohydrate is present at a concentration of about 1.08 mg/mL. In some embodiments, mannitol is present at a concentration of about 20 mg/mL to about 40 mg/mL. In some embodiments, mannitol is present at a concentration of about 32 mg/mL. In other embodiments, the formulation comprises sucrose. In some embodiments, sucrose is present at a concentration of about 75 mg/mL to about 85 mg/mL. In some embodiments, sucrose is present at a concentration of about 80 mg/mL. In some embodiments, polysorbate-80 is present at a concentration of about 0.5 mg/mL to about 1.5 mg/mL. In some embodiments, polysorbate-80 is present at a concentration of about 1.0 mg/mL. In some embodiments, polysorbate-80 is present at a concentration of about 0.5 mg/mL. In some embodiments, the pharmaceutical composition comprises about 31 mg/mL of the binding molecule, about 0.76 mg/mL of L-histidine, about 1.08 mg/mL of L-histidine monohydrate, about 32 mg/mL of mannitol, about 1.0 mg/mL of polysorbate-80, and wherein the pH of the pharmaceutical composition is about 6.0. In some embodiments, the pharmaceutical composition comprises about 25 mg/mL of the binding molecule, about 0.76 mg/mL of L-histidine, about 1.08 mg/mL of L-histidine monohydrate, about 80 mg/ml sucrose, about 0.5 mg/mL of polysorbate-80, and wherein the pH of the pharmaceutical composition is about 6.0.

In another aspect, the disclosure provides administering to the subject a therapeutically effective amount of the pharmaceutical composition described herein.

In another aspect, the disclosure provides a method of preventing a cancer in a subject, comprising administering to the subject a therapeutically effective amount of the pharmaceutical composition described herein. In some embodiments, the therapeutically effective amount of the pharmaceutical composition is administered with a therapeutically effective amount of one or more additional therapeutic agent. In some embodiments, the one or more additional agent comprises an anti-PD1 antibody. In some embodiments, the cancer is a solid tumor. In some embodiments, cancer is a blood cancer.

BRIEF DESCRIPTION OF THE FIGURES

The accompanying figures, which are incorporated herein and form a part of the specification, illustrate some, but not the only or exclusive, example embodiments and/or features. It is intended that the embodiments and figures disclosed herein are to be considered illustrative rather than limiting.

FIG. 2A shows binding to hPD-1 and FIG. 2B shows expression as assessed by Protein A (FIG. 2B) both in serial dilutions of transfection supernatants.

FIG. 3 shows the amino acid sequences of the heavy chain variable region (VH) of UDIZ-008 (SEQ ID NO: 19) and light chain variable region (VL) of UDIZ-008 (SEQ ID NO: 20), which are identical to UDIZ-007.

FIGS. 10A-10C show binding of UDIZ-007 (FIG. 10A) and UDIZ-008 (FIG. 10B) to cPD-1. Keytruda® was used as a reference. FIG. 10C shows the $EC_{50}$ for UDIZ-007 and UDIZ-008 in comparison to Keytruda®. D92C and D55C were used as negative controls.

FIGS. 11A-11C show binding of UDIZ-007 (FIG. 11A) and UDIZ-008 (FIG. 11B) to mouse PD-1 (mPD-1). A commercial antibody targeting mouse PD-1 protein (Biolegend, Cat. 114109) was used as a reference. FIG. 11C shows the $EC_{50}$ for UDIZ-007 and UDIZ-008 in comparison to the reference antibody. D92C and D55C were used as negative controls.

FIGS. 12A-12D show binding of UDIZ-007 to CTLA-4 (FIG. 12A), ICOS (FIG. 12B), and CD28 (FIG. 12C). FIG. 12D shows a comparison of the $EC_{50}$ values between antibodies. The anti-CTLA-4 antibody (Rabbit Polyclonal; Cat: 11159-RP02, SinoBiological), anti-ICOS ligand antibody (Rabbit Polyclonal; Cat: 11559-RP01, SinoBiological), and anti-CD28 antibody (Rabbit Monoclonal; Cat: 11524-R007, SinoBiological) were used as positive controls. The D92C was used as negative control.

FIGS. 13A-13D show binding of UDIZ-008 to CTLA-4 (FIG. 13A), ICOS (FIG. 13B), and CD28 (FIG. 13C). FIG. 13D shows a comparison of the $EC_{50}$ values between antibodies. The same positive and negative controls used for UDIZ-007 (FIGS. 12A-12D) were utilized in this assay.

FIGS. 14A-14C show binding of UDIZ-007 (FIG. 14A) and UDIZ-008 (FIG. 14B) to hPD-1 expressed on Jurkat cells. FIG. 14C shows a comparison of the $EC_{50}$ values between antibodies. Keytruda® was used as a reference. D92C and D55C were used as negative controls.

FIGS. 15A-15C show in vitro hPD-1:hPD-L1 blockade of UDIZ-007 and UDIZ-008 in a co-culture of cells expressing hPD-1 and hPD-L1 (FIG. 15A) and UDIZ-008 (FIG. 15B). FIG. 15C shows a comparison of the $EC_{50}$ values between antibodies. Keytruda® and Opdivo® were used as references. D92C and D55C were used as negative controls.

FIG. 16A shows blocking of hPD-1 binding to PD-L1. FIG. 16B shows blocking of hPD-1 binding to hPD-L2. Keytruda® was used as a reference. The antibody 3C5, an anti-VEGFR3 antibody, was used as negative control.

FIGS. 19A-19C show binding-ELISA of UDIZ-007 (FIG. 19A) and UDIZ-008 (FIG. 18B) antibodies to the C1q fraction of the complement system. The curve was fitted to a 4-parameter model to determine the $EC_{50}$ value. FIG. 19C shows a comparison of the $EC_{50}$ values between antibodies. Rituximab (hIgG1) was used as a positive control for C1q binding and Keytruda® as a reference for hIgG4.

FIG. 20 shows the epitope mapping results as determined by crosslinking mass spectrometry (XL-MS). The Table embedded in the figure indicates the hPD-1 fragment (first column) in contact with the CDRs of UDIZ-007 (second column) and the enzyme used to generate the fragments (third column). The position of the regions of hPD-1 identified as in contact with VH and VL are identified on sequence of hPD-1 underneath the Table. On top of the sequence, the arrows indicate β-strands and squares the loops connecting them in the hPD-1 secondary structure. VH recognizes the residues 80-104 (AAFPEDRSQPGQDCRFRVTQLPNGR; SEQ ID NO: 26) and the HCDR2 and LCDR1 and LCDR2 the residues 105-115 (DFHMSVVRARR; SEQ ID NO: 27) of hPD-1 (partial hPD-1; SEQ ID NO: 28).

FIG. 25A shows a comparison of UDIZ-007 and D92C. FIG. 25B shows a comparison between UDIZ-008 and D55C. FIG. 25C shows the tumor size shrinkage during the first 25 days of treatment with UDIZ-007, UDIZ-008 and Keytruda®.

DETAILED DESCRIPTION

Figure 1:
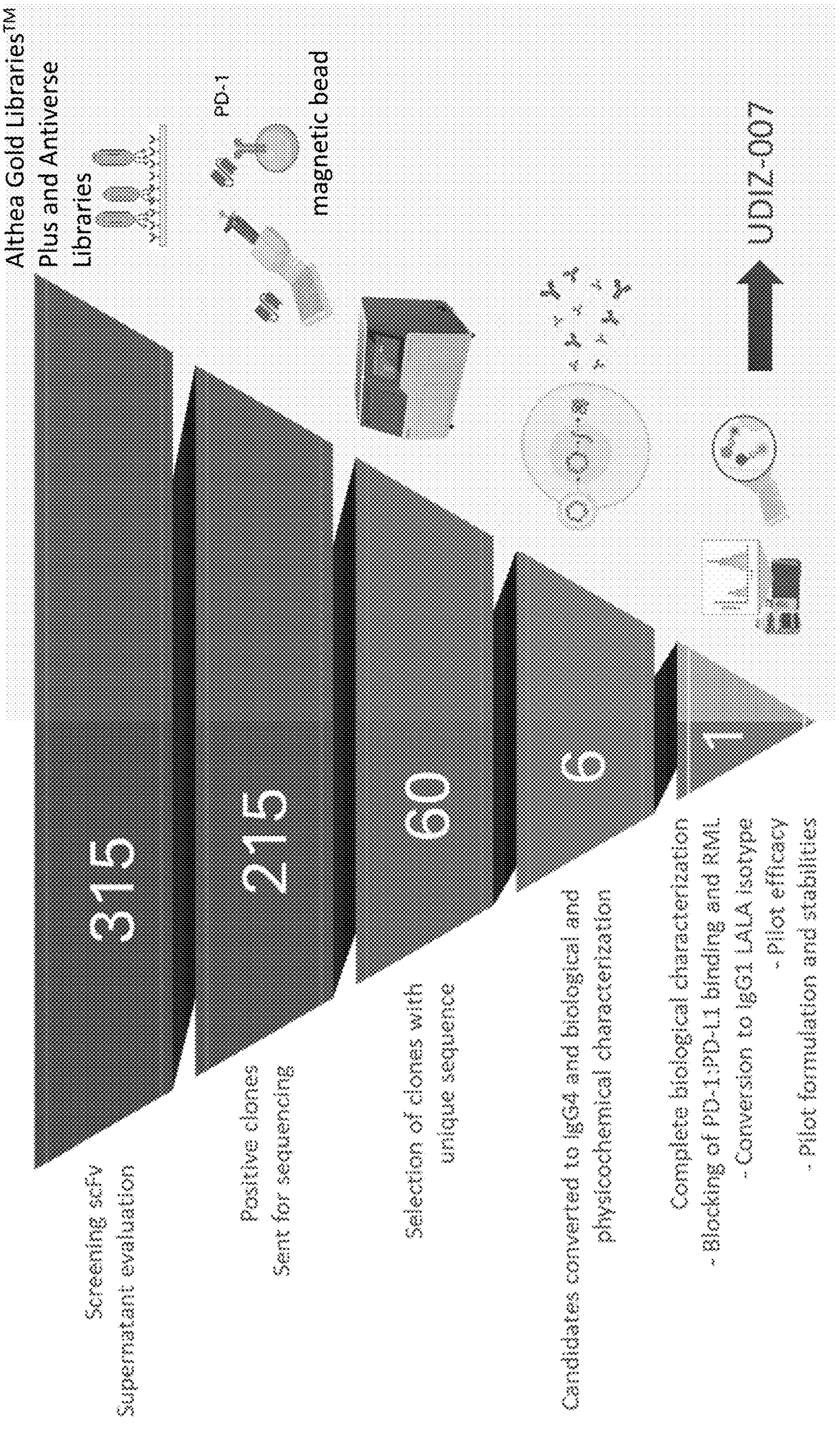
FIG. 1 shows the strategy for selection of anti-PD-1 antibody UDIZ-007 and by extension for selection of anti-PD-1 antibody UDIZ-008.

The present disclosure provides binding molecules that bind to PD-1, compositions thereof, and methods of use in the treatment and/or prevention of cancer.

Definitions

Unless otherwise defined herein, technical and scientific terms used in the present description have the meanings that are commonly understood by those of ordinary skill in the art. For purposes of interpreting this specification, the following description of terms will apply and whenever appropriate, terms used in the singular will also include the plural and vice versa unless the content clearly dictates otherwise. In the event that any description of a term set forth conflicts with any document incorporated herein by reference, the description of the term set forth below shall control.

The terms "a", "an", and "the", as used herein, include plural references unless the context clearly dictates otherwise.

The term "about", as used herein, in reference to a number or range of numbers, is understood to mean the stated number and numbers+/−10% thereof, or 10% below the lower listed limit and 10% above the higher listed limit for the values listed for a range.

The term "between", as used in a phrase as such "between A and B" or "between A-B" refers to a range including both A and B.

The terms "or" and "and/or", as used herein, include any, and all, combinations of one or more of the associated listed items.

The terms "including", "includes", "included", and other forms, as used herein, are not limiting.

The terms "comprise" and its grammatical equivalents, as used herein, specify the presence of stated features, integers, steps, operations, elements, and/or components, but do not preclude the presence or addition of one or more other features, integers, steps, operations, elements, components, and/or groups thereof.

The term "administer", "administration", or "administering", as used herein refers to the act of injecting or otherwise physically delivering a substance (e.g., a pharmaceutical composition provided herein) to a subject, such as by oral, mucosal, topical, intradermal, parenteral, intravenous, intravitreal, intraarticular, subretinal, intramuscular, intrathecal delivery and/or any other method of physical delivery described herein or known in the art. The delivery can be systemic or to a specific tissue.

The term "antibody," "immunoglobulin," or "Ig" is used interchangeably herein, and is used in the broadest sense and specifically covers, for example, monoclonal antibodies (including agonist, antagonist, neutralizing antibodies, full length or intact monoclonal antibodies), antibody compositions with polyepitopic or monoepitopic specificity, polyclonal or monovalent antibodies, multivalent antibodies, and multispecific antibodies (e.g., bispecific antibodies so long as they exhibit the desired biological activity). A conventional antibody is composed of two identical pairs of polypeptide chains, wherein each pair has one heavy chain (about 50-70 kDa) and one light chain (about 25 kDa), each amino-terminal portion of each chain includes a variable region of about 100 to about 130 or more amino acids, and each carboxy-terminal portion of each chain includes a constant region. See, e.g., Antibody Engineering (Borrebaeck, ed., 2d ed. 1995); and Kuby, Immunology (3d ed. 1997). An antibody can be human, humanized, chimeric and/or affinity matured, as well as an antibody from other species, for example, mouse and rabbit, etc. Antibodies also include, but are not limited to, synthetic antibodies, recombinantly produced antibodies, camelized antibodies or their humanized variants, and intrabodies. An antibody can be selected from any class of immunoglobulins, including IgM, IgG, IgD, IgA and IgE, and any isotype, including IgG1, IgG2, IgG3 and IgG4 (e.g., variants of IgG4 and IgG4 nullbody). An antibody can comprise kappa or lambda light chain constant sequences.

The term "antigen" refers to a molecule or a portion of a molecule capable of being bound by an antibody or an antigen-binding fragment thereof and additionally capable of being used in an animal to produce antibodies capable of binding to an epitope of that antigen. An antigen may be a polypeptide, carbohydrate, nucleic acid, lipid, hapten, or other naturally occurring or synthetic compound.

The term "antigen-binding domain", as used herein, refers to a portion of a binding molecule that specifically binds a target antigen or target epitope. Antigen-binding domains may comprise antibodies or antigen-binding fragments thereof.

The term "antigen-binding fragment," as used herein, refers to a polypeptide comprising at least one complementarity determining region (CDR) that binds to at least one epitope of an antigen of interest. In this regard, an antigen-binding fragment may comprise 1, 2, 3, 4, 5, or all 6 CDRs of a variable heavy chain (VH) and/or variable light chain (VL) sequence. Antigen-binding fragments include proteins that comprise a portion of a full length antibody, generally the antigen binding or variable region thereof, such as Fab, F(ab')2, Fab', Fv fragments, minibodies, diabodies, single domain antibodies (dAb, also known as VHH, camelid antibodies, or nanobodies), single-chain variable fragments (scFv), rIgG, antibody mimetics, and any other modified configuration of the immunoglobulin molecule that comprises an antigen-binding fragment of the required specificity.

The term "binds" or "binding", as used herein, refers to a covalent or non-covalent interaction between molecules (e.g., forming a complex by interactions). Exemplary non-covalent interactions include hydrogen bonds, ionic bonds, hydrophobic interactions, and/or van der Waals interactions. As used herein, the term "specifically binds" refers to binding of an antibody or an antigen binding fragment thereof to an antigen with a dissociation constant $(K_D) \leq 10^{-7}$ M. The term "$K_D$" is intended to refer to the dissociation equilibrium constant of a particular antibody-antigen interaction. The ratio of dissociation rate ($k_{off}$) to association rate ($k_{on}$) of an antibody to a monovalent antigen ($k_{off}/k_{on}$) is the dissociation constant $K_D$, which is inversely related to affinity. The lower the $K_D$ value, the higher the affinity of the antibody. The value of $K_D$ varies for different complexes of antibody and antigen and depends on both $k_{on}$ and $k_{off}$. The dissociation constant $K_D$ for an antibody provided herein can be determined using any method provided herein or any other method well known to those skilled in the art. Specific binding can be measured, for example, by determining binding of a molecule compared to binding of a control molecule, which generally is a molecule of similar structure that does not have binding activity.

The term "binding affinity", as used herein, refers to the strength of the sum total of noncovalent interactions between a single binding site of a molecule (e.g., a binding protein such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a binding molecule X for its binding partner Y can generally be represented by the dissociation constant (KD). Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure.

The term "binding molecule", as used herein, refers to a polypeptide or complex of polypeptides comprising at least one antigen-binding domain that specifically binds to a target antigen.

The term "coding sequence" or a polynucleotide which "encodes" a polypeptide, as used herein, is a nucleic acid molecule which is transcribed (in the case of DNA) and translated (in the case of mRNA) into a polypeptide when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

The term "constant region" or "constant domain", as used herein, refers to a carboxy terminal portion of the light and heavy chain which is not directly involved in binding of the antibody to antigen but exhibits various effector function, such as interaction with the Fc receptor. This portion has a conserved amino acid sequence relative to the variable region. The constant region may contain the CH1, CH2, and CH3 regions of the heavy chain and the CL region of the light chain.

The term "effective amount" or "therapeutically effective amount", as used herein, refers to an amount of a therapeutic (e.g., a pharmaceutical composition provided herein) which is sufficient to treat, diagnose, prevent, delay the onset of, reduce and/or ameliorate the severity and/or duration of a given condition, disorder or disease and/or a symptom related thereto. The term also encompasses an amount necessary for the reduction, slowing, or amelioration of the advancement or progression of a given disease, reduction, slowing, or amelioration of the recurrence, development or onset of a given disease, and/or to improve or enhance the prophylactic or therapeutic effect (s) of another therapy or to serve as a bridge to another therapy.

The term "epitope", as used herein, refers to a localized region of an antigen to which an antibody can bind. In the case of a polypeptide antigen, for example, an epitope can be contiguous amino acids of the polypeptide (a "linear" epitope) or an epitope can comprise amino acids from two or more non-contiguous regions of the polypeptide (a "conformational," "non-linear" or "discontinuous" epitope). It will be appreciated by one of skill in the art that, in general, a linear epitope may or may not be dependent on secondary, tertiary, or quaternary structure. In some embodiments, an antibody binds to a group of amino acids regardless of whether they are folded in a natural three-dimensional protein structure. In some embodiments, an antibody requires amino acid residues making up the epitope to exhibit a particular conformation (e.g., bend, twist, turn or fold) in order to recognize and bind the epitope.

The term "Fab" or "Fab region", as used herein, refers to an antibody region that binds to antigens. A conventional IgG usually comprises two Fab regions, each residing on one of the two arms of the Y-shaped IgG structure. Each Fab region is typically composed of one variable region and one constant region of each of the heavy and the light chain. More specifically, the variable region and the constant region of the heavy chain in a Fab region are VH and CH1 regions, and the variable region and the constant region of the light chain in a Fab region are VL and CL regions. The VH, CH1, VL, and CL in a Fab region can be arranged in various ways to confer an antigen binding capability. For example, VH and CH1 regions can be on one polypeptide, and VL and CL regions can be on a separate polypeptide, similarly to a Fab region of a conventional IgG. Alternatively, VH, CH1, VL and CL regions can all be on the same polypeptide and oriented in different orders.

The term "Fc region", as used herein, refers to a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. A "functional Fc region" possesses an "effector function" of a native sequence Fc region. Exemplary "effector functions" include C1q binding; CDC; Fc receptor binding; ADCC; phagocytosis; downregulation of cell surface receptors (e.g., B cell receptor), etc. Such effector functions generally require the Fc region to be combined with a binding region or binding domain (e.g., an antibody variable region or domain) and can be assessed using various assays known to those skilled in the art.

The term "fragment", as used herein, refers to a portion of a polypeptide or polynucleotide molecule containing less than the entire polypeptide or polynucleotide sequence. In some embodiments, a fragment of a polypeptide or polynucleotide comprises at least about 10%, about 20%, about 30%, about 40%, about 50%, about 60%, about 70%, about 80%, about 90%, about 95%, about 96%, about 97%, about 98%, or about 99% of the entire length of the reference polypeptide or polynucleotide. In some embodiments, a fragment of a polypeptide or polynucleotide comprises about 10%-99%, about 20%-99%, about 30%-99%, about 40%-99%, about 50%-99%, about 60%-99%, about 70%-99%, about 80%-99%, about 90%-99%, about 95%-99%, about 96%-99%, about 97%-99%, or about 98%-99%, of the entire length of the reference polypeptide or polynucleotide. In some embodiments, a polypeptide or polynucleotide fragment may contain about 5, about 10, about 15, about 20, about 25, about 30, about 35, about 40, about 45, about 50, about 60, about 70, about 80, about 90, about 100, about 200, about 300, about 400, about 500, about 600, about 700, about 800, about 900, about 1000, or more nucleotides or amino acids.

The term "heavy chain", when used in reference to an antibody, refers to a polypeptide chain of about 50-70 kDa, wherein the amino-terminal portion includes a variable region of about 120 to 130 or more amino acids, and a carboxy-terminal portion includes a constant region. The constant region can be one of five distinct types, (e.g, isotypes) referred to as alpha, delta, epsilon, gamma, and mu, based on the amino acid sequence of the heavy chain constant region. The distinct heavy chains differ in size: alpha, delta, and gamma contain approximately 450 amino acids, while epsilon and mu contain approximately 550 amino acids. When combined with a light chain, these distinct types of heavy chains give rise to five well known classes (e.g., isotypes) of antibodies, IgA, IgD, IgE, IgG, and IgM, respectively, including four subclasses of IgG, namely IgG1, IgG2, IgG3, and IgG4.

The term "host", as used herein, refers to an animal, such as a mammal (e.g., a human).

The term "host cell", as used herein, refers to a particular subject cell into which an exogenous nucleic acid molecule may be introduced and the progeny or potential progeny of such a cell. Progeny of such a cell may not be identical to the parent cell comprising the nucleic acid molecule due to mutations or environmental influences that may occur in succeeding generations or integration of the nucleic acid molecule into the host cell genome.

The term "isolated nucleic acid", as used herein, refers to a nucleic acid, for example, an RNA, DNA, or a mixed nucleic acids, substantially separated from other genomic DNA sequences as well as proteins or complexes such as ribosomes and polymerases that naturally accompany a native sequence, or culture medium when produced by recombinant techniques, or chemical precursors or other chemicals when chemically synthesized.

The term “light chain”, when used in reference to an antibody, refers to a polypeptide chain of about 25 kDa, wherein the amino-terminal portion includes a variable region of about 100 to about 110 or more amino acids, and a carboxy-terminal portion includes a constant region. The approximate length of a light chain is 211 to 217 amino acids. There are two distinct types, referred to as kappa or lambda based on the amino acid sequence of the constant domains.

The term “monoclonal antibody,” as used herein, refers to an antibody obtained from a population of substantially homogeneous antibodies, e.g., the individual antibodies comprising the population are identical except for possible naturally occurring mutations that may be present in minor amounts, and each monoclonal antibody will typically recognize a single epitope on the antigen.

The term “operatively linked” and similar phrases (e.g., operably linked, genetically fused), as used herein, refer to the operational linkage of nucleic acid sequences or amino acid sequences placed in functional relationships with each other. For example, a promoter operatively linked to a polynucleotide encoding a polypeptide result in the transcription of the polynucleotide and ultimately the expression of the polypeptide. As another example, an operatively linked peptide is one in which the functional domains are placed with appropriate distance from each other to impart the intended function of each domain.

The term “pharmaceutically acceptable excipient, carrier or diluent”, as used herein, refers to any substance formulated alongside the active ingredient of a pharmaceutical composition that allows the active ingredient to retain biological activity and is non-reactive with the subject’s immune system. Such a substance can be included for the purpose of long-term stabilization, bulking up solid formulations that contain potent active ingredients in small amounts, or to confer a therapeutic enhancement on the active ingredient in the final dosage form, such as facilitating absorption, reducing viscosity, or enhancing solubility. The selection of appropriate substance can depend upon the route of administration and the dosage form, as well as the active ingredient and other factors. Compositions having such substances can be formulated by well-known conventional methods (see, e.g., Remington, The Science and Practice of Pharmacy, 23rd edition, A. Adejare, ed., Academic Press, 2020).

The term “pharmaceutical composition” or “therapeutic composition”, as used here, refers to a composition capable of being administered to a subject for the treatment of a particular disease or disorder.

The term “polynucleotide” or “nucleic acid”, as used herein, refers to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, genomic DNA (gDNA), PCR amplified DNA, complementary DNA (cDNA), synthetic DNA, or recombinant DNA. Polynucleotides can comprises modified nucleotides or bases, and/or their analogs, or any substrate that can be incorporated into a polymer by DNA or RNA polymerase or by a synthetic reaction. Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction.

The terms “polypeptide” and “peptide” and “protein”, as used herein, refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art.

The term “prevent”, as used herein, refers to a pharmaceutical or other intervention regimen for reducing the likelihood of the onset (or recurrence) of a disease, disorder, condition, or associated symptom(s). Preventing includes delaying, preventing, or eliminating the appearance of a disease or condition, delaying, or eliminating the onset of symptoms of a disease or condition, slowing, halting, or reversing the progression of a disease or condition, or any combination thereof.

The term “sequence identity”, as used herein, refers to the percentage of bases or amino acids between two polynucleotide or polypeptide sequences that are the same, and in the same relative position. As such one polynucleotide or polypeptide sequence has a certain percentage of sequence identity compared to another polynucleotide or polypeptide sequence. For sequence comparison, typically one sequence acts as a reference sequence, to which test sequences are compared. The term “reference sequence” refers to a molecule to which a test sequence is compared. Methods of sequence alignment for comparison and determination of percent sequence identity and percent complementarity are well known in the art. Optimal alignment of sequences for comparison can be conducted, e.g., by the homology alignment algorithm of Needleman and Wunsch, (1970) J. Mol. Biol. 48:443, by the search for similarity method of Pearson and Lipman, (1988) Proc. Nat’l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, WI), by manual alignment and visual inspection (see, e.g., Brent et al., (2003) Current Protocols in Molecular Biology), by use of algorithms know in the art including the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information. BLAST nucleotide searches can be performed with the NBLAST nucleotide program parameters set, e.g., for score 1 00, word length-! 2 to obtain nucleotide sequences homologous to a nucleic acid molecule described herein. BLAST protein searches can be performed with the XBLAST program parameters set, e.g., to score 50, word length-3 to obtain amino acid sequences homologous to a protein molecule described herein. To obtain gapped alignments for comparison purposes, Gapped BLAST can be utilized as described in Altschul et al., Nucleic Acids Res., 1997, 25:3389-402. Alternatively, PSI BLAST can be used to perform an iterated search which detects distant relationships between molecules (Id.). When utilizing BLAST, Gapped BLAST, and PSI BLAST programs, the default parameters of the respective programs (e.g., of XBLAST and NBLAST) can be used (see, e.g., National Center for Biotechnology Information (NCBI) on the worldwide web, ncbi.nlm.nih.gov). Another non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The term "subject", as used herein, refers to an "animal" and in particular a "mammal" such as a non-primate (e.g., mice, rats, bovines, horses, household cats, tigers and other large cats, dogs, pigs, rabbits, goats, deer, sheep, ferrets, gerbils, guinea pigs, hamsters, bats, and birds (e.g., chickens, turkeys, and ducks)) or a primate (e.g., monkeys, baboons, chimpanzees, and human). The term may be used interchangeably with the term "patient" or "individual". In some embodiments, the subject is a mammal, e.g., a human, diagnosed with a disease or disorder provided herein. In some embodiments, the subject is a mammal, e.g., a human, at risk of developing a disease or disorder provided herein.

The terms "treatment" and "treating", as used herein, refer to a pharmaceutical or other intervention regimen for obtaining beneficial or desired results in the recipient. Treating may refer to eradication or amelioration of symptoms or of an underlying disorder being treated. Treating may also be achieved with the eradication or amelioration of one or more of the physiological symptoms associated with the underlying disorder such that an improvement is observed in the subject, notwithstanding that the subject may still be afflicted with the underlying disorder.

The term "refractory" or "insensitive" or "resistant" refers to a disease that does not respond to a treatment. A refractory disease can be resistant to a treatment before or at the beginning of the treatment, or a refractory disease can become resistant during a treatment.

The term "variable region", "variable domain", "V region", or "V domain", as used herein, refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" or "complementarity determining regions" that are each about 9-12 amino acids long. The variable regions of heavy and light chains each comprise four FRs, largely adopting a β sheet configuration, connected by three hypervariable regions, which form loops connecting, and in some cases form part of, the β sheet structure. The hypervariable regions in each chain are held together in close proximity by the FRs and, with the hypervariable regions from the other chain, contribute to the formation of the antigen-binding site of antibodies (see, e.g., Kabat et al, Sequences of Proteins of Immunological Interest (5th ed. 1991)).

The complementarity determining regions (CDRs) have been defined by well-known numbering systems. An overview of these systems is provided in Dondelinger et al., Understanding the Significance and Implications of Antibody Numbering and Antigen-Binding Surface/Residue Definition. Front Immunol. 2018 Oct. 16; 9:2278. For example, the Kabat Complementarity Determining Regions (CDRs) are based on sequence variability and are the most commonly used (see, e.g., Kabat, et al., supra). Chothia refers instead to the location of the structural loops (see, e.g., Chothia and Lesk, J. Mol. Biol., 1987, 196:901-17). The end of the Chothia CDR-H1 loop when numbered using the Kabat numbering convention varies between H32 and H34 depending on the length of the loop (this is because the Kabat numbering scheme places insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., Antibody Engineering Vol. 2 (Rontermann and Diibel, eds., 2d ed. 2010)). The "contact" CDRs are based on an analysis of the available complex crystal structures. Another universal numbering system that has been developed and widely adopted is ImMunoGeneTics (IMGT) Information System® (Lafranc, et al, Dev. Comp. Immunol., 2003, 27(1):55-77). IMGT is an integrated information system specializing in immunoglobulins (IG), T-cell receptors (TCR), and major histocompatibility complex (MHC) of human and other vertebrates. An additional numbering system (AHon) has been developed by Honegger and Pluckthun, J. Mol. Biol., 2001, 309: 657-70. Correspondence between the numbering systems, including, for example, the Kabat numbering and the IMGT unique numbering system, is well known to one skilled in the art (see, e.g., Kabat, supra, Chothia and Lesk, supra; Martin, supra, Lefranc, et al., supra). The boundaries of a given CDR may vary depending on the scheme used for identification. Thus, unless otherwise specified, the CDRs of a given antibody or region thereof, such as a variable region, should be understood to encompass the complementary determining region as defined by any of the known schemes described herein. In some instances, the scheme for identification of a particular CDR or CDRs is specified, such as the CDR as defined by the Kabat, Chothia, or Contact method. In other cases, the particular amino acid sequence of a CDR is given. In some embodiments, a combination of CDR numbering systems may be used. In such embodiments, CDR sequences of a given binding molecule as determined by multiple numbering systems (e.g., a CDR1 sequence as determined by the Kabat, IMGT, and Chothia numbering systems) are compiled into a single sequence that encompasses the entirety of each of the CDR amino acid ranges in the variable region.

As the "location" of the CDRs within the structure of the immunoglobulin variable domain is conserved between species and present in structures called loops, by using numbering systems that align variable domain sequences according to structural features, CDR and framework residues are readily identified. This information can be used in grafting and replacement of CDR residues from immunoglobulins of one species into an acceptor framework from, typically, a human antibody.

The term "variant", when used in relation to polypeptide, refers to a polypeptide comprising one or more (such as, for example, about 1 to about 25, about 1 to about 20, about 1 to about 15, about 1 to about 10, or about 1 to about 5) amino acid sequence substitutions, deletions, and/or additions as compared to a native or unmodified sequence. Variants may be naturally occurring, such as allelic or splice variants, or may be artificially constructed. Polypeptide variants may be prepared from the corresponding nucleic acid molecules encoding the variants.

The term "vector", as used herein, refers to a substance that is used to carry or introduce a nucleic acid sequence (e.g., a nucleic acid sequence encoding an antibody as described herein) into a host cell. Vectors applicable for use include, for example, plasmids, phage vectors, viral vectors, episomes, and artificial chromosomes. A vector may include sequences that direct autonomous replication in a cell, or may include sequences sufficient to allow integration into host cell DNA. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like, which are well known in the art. When two or more nucleic acid molecules are to be co-expressed (e.g., both an antibody heavy and light chain or an antibody VH and VL), both nucleic acid molecules can be inserted, for example, into a single expression vector or in separate expression vectors. For single vector expression, the encoding nucleic acids can be operationally linked to one common expression control sequence or linked to different expression control sequences. The introduction of nucleic acid molecules into a host cell can be confirmed using methods well known in the art. Such methods include, for example, nucleic acid analysis such as Northern blots or polymerase chain reaction (PCR) amplification of mRNA, immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product and it is further understood that expression levels can be optimized to obtain sufficient expression using methods well known in the art.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Binding Molecules

Programmed death protein 1 (PD-1), also known as CD279, is a coinhibitory receptor member of the CD28 receptor family. It has a 15% identity with the amino acid sequence of CD28, whereas exhibits 20% and 13% with cytotoxic T-lymphocyte antigen 4 (CTLA-4) and induced T-cell co-stimulator (ICOS), respectively. PD-1 is expressed on the surface of T cells, NK cells, and B cells, playing an essential role in the immune system downregulation and promoting self-tolerance upon binding with its ligands, PD-L1 (B7-H1) and PD-L2 (B7-DC). In several malignancies such as melanoma, non-small-cell lung cancer, breast cancer, squamous cell carcinoma, colon adenocarcinoma, and breast adenocarcinoma, among others, PD-L1 and/or PD-L2 are upregulated, inhibiting T cell proliferation, activation, cytokine secretion, and cytotoxic T lymphocyte (CTL) killing functions, resulting in tumor immune evasion. Thus, current therapies focused on blocking the interaction with monoclonal antibodies between PD-1 and PD-L1/L2 have held the promise of being efficacious treatments for a range of cancers.

Provided herein is a binding molecule that binds to programmed cell death protein 1 (PD-1). In some embodiments, the PD-1 is human PD-1. The UniProt ID for human PD-1 is Q15116. The amino acid sequence of human PD-1 is shown below.

```
                                            (SEQ ID NO: 25)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKAQIKESLRAELRVTERRAE

VPTAHPSPSPRPAGQFQTLVVGVVGGLLGSLVLLVWVLAVICSRAARGTI

GARRTGQPLKEDPSAVPVFSVDYGELDFQWREKTPEPPVPCVPEQTEYAT

IVFPSGMGTSSPARRGSADGPRSAQPLRPEDGHCSWPL.
```

In some embodiments, the binding molecule is a monoclonal antibody or antigen-binding fragment thereof that binds to PD-1. In some embodiments, the binding molecule is a fully human monoclonal antibody or antigen-binding fragment thereof that binds to PD-1.

In some embodiments, the monoclonal antibody or antigen-binding fragment thereof comprises an IgG isotype selected from the group consisting of IgG1, IgG2, IgG3, IgG4, and a variant thereof. In some embodiments, the variant IgG isotype has improved stability compared to a wildtype IgG isotype. In some embodiments, the variant IgG isotype has reduced binding to FcγRI, FcγRII, and FcγRIII receptors, as well as to complement C1q, compared to a wildtype IgG isotype. In some embodiments, the variant IgG isotype has decreased effector function compared to a wildtype IgG isotype. In some embodiments, the monoclonal antibody or antigen-binding fragment thereof comprises an IgG4 isotype. In some embodiments, the binding molecule is a fully human monoclonal antibody comprising an IgG4-PE. In some embodiments, the term "IgG4-PE" refers to an IgG4 isotype comprising the "PE" mutations (P228S/E235L, Kabat numbering). In some embodiments, the monoclonal antibody or antigen-binding fragment thereof comprises an IgG1 isotype. In some embodiments, the binding molecule is a fully human monoclonal antibody comprising IgG1-LALA. In some embodiments, the term "IgG1-LALA" refers to an IgG1 isotype comprising the "LALA" mutations (L234A/L235A, Kabat numbering).

In some embodiments, the binding molecule is numbered with reference to the Kabat numbering. In some embodiments, the binding molecule comprises a variable heavy chain CDR1 (HCDR1) comprising an amino acid sequence of SEQ ID No: 1. In some embodiments, the binding molecule thereof comprises a variable heavy chain CDR2 (HCDR2) comprising an amino acid sequence of SEQ ID No: 2. In some embodiments, the binding molecule thereof comprises a variable heavy chain CDR3 (HCDR3) comprising an amino acid sequence of SEQ ID No: 3. In some embodiments, the binding molecule comprises a variable light chain CDR1 (LCDR1) comprising an amino acid sequence of SEQ ID No: 4. In some embodiments, the binding molecule comprises a variable light chain CDR2 (LCDR2) comprising an amino acid sequence of SEQ ID No: 5. In some embodiments, the binding molecule comprises a variable light chain CDR3 (LCDR3) comprising an amino acid sequence of SEQ ID No: 6. In some embodiments, the binding molecule is numbered with reference to the ImMunoGeneTics (IMGT) numbering. In some embodiments, the binding molecule comprises a variable heavy chain CDR1 (HCDR1) comprising an amino acid sequence of SEQ ID No: 7. In some embodiments, the binding molecule thereof comprises a variable heavy chain CDR2 (HCDR2) comprising an amino acid sequence of SEQ ID No: 8. In some embodiments, the binding molecule thereof comprises a variable heavy chain CDR3 (HCDR3) comprising an amino acid sequence of SEQ ID No: 9. In some embodiments, the binding molecule comprises a variable light chain CDR1 (LCDR1) comprising an amino acid sequence of SEQ ID No:10. In some embodiments, the binding molecule comprises a variable light chain CDR2 (LCDR2) comprising an amino acid sequence of SEQ ID No: 11. In some embodiments, the binding molecule comprises a variable light chain CDR3 (LCDR3) comprising an amino acid sequence of SEQ ID No: 12. In some embodiments, the binding molecule is numbered with reference to the Chothia numbering. In some embodiments, the binding molecule comprises a variable heavy chain CDR1 (HCDR1) comprising an amino acid sequence of SEQ ID No: 13. In some embodiments, the binding molecule thereof comprises a variable heavy chain CDR2 (HCDR2) comprising an amino acid sequence of SEQ ID No: 14. In some embodiments, the binding molecule thereof comprises a variable heavy chain CDR3 (HCDR3) comprising an amino acid sequence of SEQ ID No: 15. In some embodiments, the binding molecule comprises a variable light chain CDR1 (LCDR1) comprising an amino acid sequence of SEQ ID No: 16. In some embodiments, the binding molecule comprises a variable light chain CDR2 (LCDR2) comprising an amino acid sequence of SEQ ID No: 17. In some embodiments, the binding molecule comprises a variable light chain CDR3 (LCDR3) comprising an amino acid sequence of SEQ ID No: 18.

In some embodiments, the binding molecule comprises: 1) a HCDR1 comprising an amino acid sequence of SEQ ID No: 1; 2) a HCDR2 comprising an amino acid sequence of SEQ ID No: 2; 3) a HCDR3 comprising an amino acid sequence of SEQ ID No: 3; 4) a LCDR1 comprising an amino acid sequence of SEQ ID No: 4; 5) a LCDR2 comprising an amino acid sequence of SEQ ID No: 5; and 6) a LCDR3 comprising an amino acid sequence of SEQ ID No: 6; and wherein the binding molecule is numbered with reference to the Kabat numbering. In some embodiments, the binding molecule comprises: 1) a HCDR1 comprising an amino acid sequence of SEQ ID No: 7; 2) a HCDR2 comprising an amino acid sequence of SEQ ID No: 8; 3) a HCDR3 comprising an amino acid sequence of SEQ ID No: 9; 4) a LCDR1 comprising an amino acid sequence of SEQ ID No: 10; 5) a LCDR2 comprising an amino acid sequence of SEQ ID No: 11; and 6) a LCDR3 comprising an amino acid sequence of SEQ ID No: 12; and wherein the binding molecule is numbered with reference to the IMGT numbering. In some embodiments, the binding molecule comprises: 1) a HCDR1 comprising an amino acid sequence of SEQ ID No: 13; 2) a HCDR2 comprising an amino acid sequence of SEQ ID No: 14; 3) a HCDR3 comprising an amino acid sequence of SEQ ID No: 15; 4) a LCDR1 comprising an amino acid sequence of SEQ ID No: 16; 5) a LCDR2 comprising an amino acid sequence of SEQ ID No: 17; and 6) a LCDR3 comprising an amino acid sequence of SEQ ID No: 18; and wherein the binding molecule is numbered with reference to the Chothia numbering.

In some embodiments, the binding molecule comprises a HCDR1 consisting of an amino acid sequence of SEQ ID No: 1, a HCDR2 consisting of an amino acid sequence of SEQ ID No: 2, a HCDR3 consisting of an amino acid sequence of SEQ ID No: 3, a LCDR1 consisting of an amino acid sequence of SEQ ID No: 4, a LCDR2 consisting of an amino acid sequence of SEQ ID No: 5, and a LCDR3 consisting of an amino acid sequence of SEQ ID No: 6. In some embodiments, the binding molecule comprises a HCDR1 consisting of an amino acid sequence of SEQ ID No: 7, a HCDR2 consisting of an amino acid sequence of SEQ ID No: 8, a HCDR3 consisting of an amino acid sequence of SEQ ID No: 9, a LCDR1 consisting of an amino acid sequence of SEQ ID No: 10, a LCDR2 consisting of an amino acid sequence of SEQ ID No: 11, and a LCDR3 consisting of an amino acid sequence of SEQ ID No: 12. In some embodiments, the binding molecule comprises a HCDR1 consisting of an amino acid sequence of SEQ ID No: 13, a HCDR2 consisting of an amino acid sequence of SEQ ID No: 14, a HCDR3 consisting of an amino acid sequence of SEQ ID No: 15, a LCDR1 consisting of an amino acid sequence of SEQ ID No: 16, a LCDR2 consisting of an amino acid sequence of SEQ ID No: 17, and a LCDR3 consisting of an amino acid sequence of SEQ ID No: 18.

In some embodiments, the binding molecule comprises a heavy chain variable domain (VH) comprising an amino acid sequence that is at least about 70%, about 75%, about 80%, about 85%, about 90%, about 91%, about 92%, about 93%, about 94%, about 95%, about 96%, about 97%, about 98%, or about 99% identical to SEQ ID No: 19. In some embodiments, the binding molecule comprises a heavy chain variable domain (VH) comprising an amino acid sequence that is at least about 85% identical to SEQ ID No: 19. In some embodiments, the binding molecule comprises a VH comprising an amino acid sequence of SEQ ID No: 19. In some embodiments, the binding molecule comprises a VH consisting of an amino acid sequence of SEQ ID No: 19.

In some embodiments, the binding molecule comprises alight chain variable domain (VL) comprising an amino acid sequence that is at least about 70%, about 75%, about 80%, about 85%, about 90%, about 91%, about 92%, about 93%, about 94%, about 95%, about 96%, about 97%, about 98%, or about 99% identical to SEQ ID No: 20. In some embodiments, the binding molecule comprises a light chain variable domain (VL) comprising an amino acid sequence that is at least about 85% identical to SEQ ID No: 20. In some embodiments, the binding molecule comprises a VL comprising an amino acid sequence of SEQ ID No: 20. In some embodiments, the binding molecule comprises a VL consisting of an amino acid sequence of SEQ ID No: 20.

In some embodiments, the binding molecule comprises a VH comprising an amino acid sequence that is at least about 70%, about 75%, about 80%, about 85%, about 90%, about 91%, about 92%, about 93%, about 94%, about 95%, about 96%, about 97%, about 98%, or about 99% identical to SEQ ID No: 19, and a VL comprising an amino acid sequence that is at least about 70%, about 75%, about 80%, about 85%, about 90%, about 91%, about 92%, about 93%, about 94%, about 95%, about 96%, about 97%, about 98%, or about 99% identical to SEQ ID No: 20. In some embodiments, the binding molecule comprises a heavy chain variable domain (VH) comprising an amino acid sequence that is at least about 85% identical to SEQ ID No: 19, and a light chain variable domain (VL) comprising an amino acid sequence that is at least about 85% identical to SEQ ID No: 20.

In some embodiments, the binding molecule comprises a VH comprising an amino acid sequence of SEQ ID No: 19, and a VL comprising an amino acid sequence of SEQ ID No: 20. In some embodiments, the binding molecule comprises a VH consisting of an amino acid sequence of SEQ ID No: 19, and a VL consisting of an amino acid sequence of SEQ ID No: 20.

In some embodiments, the binding molecule is a fully human monoclonal antibody comprising an IgG4-PE. In some embodiments, the binding molecule comprises a heavy chain comprising an amino acid sequence that is at least about 70%, about 75%, about 80%, about 85%, about 90%, about 91%, about 92%, about 93%, about 94%, about 95%, about 96%, about 97%, about 98%, or about 99% identical to SEQ ID No: 21. In some embodiments, the binding molecule comprises a heavy chain comprising an amino acid sequence that is at least about 85% identical to SEQ ID NO: 21. In some embodiments, the binding molecule comprises a heavy chain comprising an amino acid sequence of SEQ ID NO: 21. In some embodiments, the binding molecule comprises a heavy chain consisting of an amino acid sequence of SEQ ID NO: 21.

In some embodiments, the binding molecule comprises a light chain comprising an amino acid sequence that is at least about 70%, about 75%, about 80%, about 85%, about 90%, about 91%, about 92%, about 93%, about 94%, about 95%, about 96%, about 97%, about 98%, or about 99% identical to SEQ ID No: 22. In some embodiments, the binding molecule comprises a light chain comprising an amino acid sequence that is at least about 85% identical to SEQ ID NO: 22. In some embodiments, the binding molecule comprises a light chain comprising an amino acid sequence of SEQ ID NO: 22. In some embodiments, the binding molecule comprises a light chain consisting of an amino acid sequence of SEQ ID NO: 22.

In some embodiments, the binding molecule comprises a heavy comprising an amino acid sequence that is at least about 70%, about 75%, about 80%, about 85%, about 90%, about 91%, about 92%, about 93%, about 94%, about 95%, about 96%, about 97%, about 98%, or about 99% identical to SEQ ID No: 21, and a light chain comprising an amino acid sequence that is at least about 70%, about 75%, about 80%, about 85%, about 90%, about 91%, about 92%, about 93%, about 94%, about 95%, about 96%, about 97%, about 98%, or about 99% identical to SEQ ID No: 22. In some embodiments, the binding molecule comprises a heavy chain comprising an amino acid sequence that is at least about 85% identical to SEQ ID No: 21, and a light chain comprising an amino acid sequence that is at least about 85% identical to SEQ ID No: 22.

In some embodiments, the binding molecule comprises a heavy chain comprising an amino acid sequence of SEQ ID No: 21, and a light chain comprising an amino acid sequence of SEQ ID No: 22. In some embodiments, the binding molecule comprises a heavy chain consisting of an amino acid sequence of SEQ ID No: 21, and a light consisting of an amino acid sequence of SEQ ID No: 22.

In some embodiments, the binding molecule is a fully human monoclonal antibody comprising an IgG1-LALA. In some embodiments, the binding molecule comprises a heavy chain comprising an amino acid sequence that is at least about 70%, about 75%, about 80%, about 85%, about 90%, about 91%, about 92%, about 93%, about 94%, about 95%, about 96%, about 97%, about 98%, or about 99% identical to SEQ ID No: 23. In some embodiments, the binding molecule comprises a heavy chain comprising an amino acid sequence that is at least about 85% identical to SEQ ID NO: 23. In some embodiments, the binding molecule comprises a heavy chain comprising an amino acid sequence of SEQ ID NO: 23. In some embodiments, the binding molecule comprises a heavy chain consisting of an amino acid sequence of SEQ ID NO: 23.

In some embodiments, the binding molecule comprises a light chain comprising an amino acid sequence that is at least about 70%, about 75%, about 80%, about 85%, about 90%, about 91%, about 92%, about 93%, about 94%, about 95%, about 96%, about 97%, about 98%, or about 99% identical to SEQ ID No: 24. In some embodiments, the binding molecule comprises a light chain comprising an amino acid sequence that is at least about 85% identical to SEQ ID NO: 24. In some embodiments, the binding molecule comprises a light chain comprising an amino acid sequence of SEQ ID NO: 24. In some embodiments, the binding molecule comprises a light chain consisting of an amino acid sequence of SEQ ID NO: 24.

In some embodiments, the binding molecule comprises a heavy comprising an amino acid sequence that is at least about 70%, about 75%, about 80%, about 85%, about 90%, about 91%, about 92%, about 93%, about 94%, about 95%, about 96%, about 97%, about 98%, or about 99% identical to SEQ ID No: 23, and a light chain comprising an amino acid sequence that is at least about 70%, about 75%, about 80%, about 85%, about 90%, about 91%, about 92%, about 93%, about 94%, about 95%, about 96%, about 97%, about 98%, or about 99% identical to SEQ ID No: 24. In some embodiments, the binding molecule comprises a heavy chain comprising an amino acid sequence that is at least about 85% identical to SEQ ID No: 23, and a light chain comprising an amino acid sequence that is at least about 85% identical to SEQ ID No: 24.

In some embodiments, the binding molecule comprises a heavy chain comprising an amino acid sequence of SEQ ID No: 23, and a light chain comprising an amino acid sequence of SEQ ID No: 24. In some embodiments, the binding molecule comprises a heavy chain consisting of an amino acid sequence of SEQ ID No: 23, and a light consisting of an amino acid sequence of SEQ ID No: 24.

The amino acid sequences of Complementarity Determining Regions (CDRs), heavy chain variable domain (VH), light chain variable domain (VL), heavy chain (HC), and light chain (LC) of two exemplary binding molecules (UDIZ-008 and UDIZ-007) are shown in Tables 1.

TABLE 1

Amino Acid Sequences of Exemplary Binding

| Domain | Sequence | SEQ ID |
|---|---|---|
| HCDR1-Kabat | NYAMS | 1 |
| HCDR2-Kabat | SITGSGSTTYYADSVKG | 2 |
| HCDR3-Kabat | PYSVGYFDY | 3 |

TABLE 1-continued

| Amino Acid Sequences of Exemplary Binding | | |
|---|---|---|
| Domain | Sequence | SEQ ID |
| LCDR1-Kabat | RASQSISSYLN | 4 |
| LCDR2-Kabat | AASSLOS | 5 |
| LCDR3-Kabat | QQSYDLPYT | 6 |
| HCDR1-IMGT | GFTFNNYA | 7 |
| HCDR2-IMGT | ITGSGSTT | 8 |
| HCDR3-IMGT | ASPYSVGYFDY | 9 |
| LCDR1-IMGT | QSISSY | 10 |
| LCDR2-IMGT | AAS | 11 |
| LCDR3-IMGT | QQSYDLPYT | 12 |
| HCDR1-Chothia | GFTFNNY | 13 |
| HCDR2-Chothia | TGSGST | 14 |
| HCDR3-Chothia | PYSVGYFDY | 15 |
| LCDR1-Chothia | RASQSISSYLN | 16 |
| LCDR2-Chothia | AASSLQS | 17 |
| LCDR3-Chothia | QQSYDLPYT | 18 |
| VH | EVQLLESGGGLVQPGGSLRLSCAASGFTENNYAMS<br>WVRQAPGKGLEWVSSITGSGSTTYYADSVKGRFTI<br>SRDNSKNTLYLQMNSLRAEDTAVYYCASPYSVGY<br>FDYWGQGTLVTVSS | 19 |
| VL | DIQMTQSPSSLSASVGDRVTITCRASQSISSYLNWY<br>QQKPGKAPKLLIYAASSLQSGVPSRFSGSGSGTDFT<br>LTISSLQPEDFATYYCQQSYDLPYTFGQGTKVEIK | 20 |
| Heavy chain UDIZ-008 | EVQLLESGGGLVQPGGSLRLSCAASGFTFNNYAMS<br>WVRQAPGKGLEWVSSITGSGSTTYYADSVKGRFTI<br>SRDNSKNTLYLQMNSLRAEDTAVYYCASPYSVGY<br>FDYWGQGTLVTVSSASTKGPSVFPLAPCSRSTSEST<br>AALGCLVKDYFPEPVTVSWNSGALTSGVHTFPAV<br>LQSSGLYSLSSVVTVPSSSLGTKTYTCNVDHKPSNT<br>KVDKRVESKYGPPCPPCPAPEFEGGPSVFLFPPKPK<br>DTLMISRTPEVTCVVVDVSQEDPEVQFNWYVDGV<br>EVHNAKTKPREEQFNSTYRVVSVLTVLHQDWLNG<br>KEYKCKVSNKGLPSSIEKTISKAKGQPREPQVYTLP<br>PSQEEMTKNQVSLTCLVKGFYPSDIAVEWESNGQP<br>ENNYKTTPPVLDSDGSFFLYSRLTVDKSRWQEGN<br>VFSCSVMHEALHNHYTQKSLSLSLG | 21 |
| Light chain UDIZ-008 | DIQMTQSPSSLSASVGDRVTITCRASQSISSYLNWY<br>QQKPGKAPKLLIYAASSLQSGVPSRFSGSGSGTDFT<br>LTISSLQPEDFATYYCQQSYDLPYTFGQGTKVEIKR<br>TVAAPSVFIFPPSDEQLKSGTASVVCLLNNFYPREA<br>KVQWKVDNALQSGNSQESVTEQDSKDSTYSLSST<br>LTLSKADYEKHKVYACEVTHQGLSSPVTKSFNRG<br>EC | 22 |
| Heavy chain UDIZ-007 | EVQLLESGGGLVQPGGSLRLSCAASGFTFNNYAMS<br>WVRQAPGKGLEWVSSITGSGSTTYYADSVKGRFTI<br>SRDNSKNTLYLQMNSLRAEDTAVYYCASPYSVGY<br>FDYWGQGTLVTVSSASTKGPSVFPLAPSSKSTSGG<br>TAALGCLVKDYFPEPVTVSWNSGALTSGVHTFPA<br>VLQSSGLYSLSSVVTVPSSSLGTQTYICNVNHKPSN<br>TKVDKKVEPKSCDKTHTCPPCPAPEAAGGPSVFLF<br>PPKPKDTLMISRTPEVTCVVVDVSHEDPEVKFNWY<br>VDGVEVHNAKTKPREEQYNSTYRVVSVLTVLHQD<br>WLNGKEYKCKVSNKALPAPIEKTISKAKGQPREPQ<br>VYTLPPSRDELTKNQVSLTCLVKGFYPSDIAVEWE<br>SNGQPENNYKTTPPVLDSDGSFFLYSKLTVDKSRW<br>QQGNVFSCSVMHEALHNHYTQKSLSLSPG | 23 |

TABLE 1-continued

| Amino Acid Sequences of Exemplary Binding | | |
|---|---|---|
| Domain | Sequence | SEQ ID |
| Light chain UDIZ-007 | DIQMTQSPSSLSASVGDRVTITCRASQSISSYLNWY QQKPGKAPKLLIYAASSLQSGVPSRFSGSGSGTDFT LTISSLQPEDFATYYCQQSYDLPYTFGQGTKVEIKR TVAAPSVFIFPPSDEQLKSGTASVVCLLNNFYPREA KVQWKVDNALQSGNSQESVTEQDSKDSTYSLSST LTLSKADYEKHKVYACEVTHQGLSSPVTKSFNRG EC | 24 |

In some embodiments, the binding molecules described herein bind to an epitope in the PD-1 protein that does not overlap with, or only partially overlaps with, an epitope bound by hPD-L 1 or Keytruda®. In some embodiments, the binding molecules described herein bind to an epitope in the PD-1 protein located between amino acids 80-115 of SEQ ID NO: 25. In some embodiments, the binding molecules described herein binds to an epitope residues in the PD-1 protein located between amino acids 105-115 of SEQ ID NO: 25 that does not overlap with, an epitope bound by hPD-L1 or Keytruda®.

In some embodiments, the binding molecules described herein inhibit the interaction between PD-1 and programmed cell death ligand 1 (PD-L1). In some embodiments, the binding molecules described herein directly inhibit the interaction between PD-1 and PD-L1 (e.g., by binding to an epitope on the PD-1 protein that mediates binding to PD-L1). In some embodiments, the binding molecules described herein indirectly inhibit the interaction between PD-1 and PD-L1 (e.g., by steric hindrance). Since epitope specificity plays an important role in defining the anti-PD-1 antibody functions, UDIZ-007/UDIZ-008 unique epitope could lead to differences in oncology indications with respect to approved antibodies or be efficacious where the known antibodies have shown limited application. Moreover, UDIZ-007 and UDIZ-008 alone, in combination with other approved anti-PD1 antibodies, or as part of multi-specific therapeutics formats that link UDIZ-007 and UDIZ-008 with antibodies binding non-overlapping epitopes to enhance the specificity of current anti-PD1 therapeutic antibodies could be valuable new therapeutic options to treat cancer.

In some embodiments, the binding molecule activates the immune system. In some embodiments, the binding molecule blocks the interaction of PD-1 and PD-L1 by way of steric hinderance and thereby activates the immune system. In some embodiments, the binding molecule activates T cells, B cells or a combination thereof. In some embodiments, CD4+ T cells are activated. In some embodiments, the activation of the immune system results in tumor cell lysis (e.g., by activated T cells).

Modifications and Variations

Amino acid sequence modification(s) of the binding molecules provided herein are contemplated. These modifications can provide for some additional property, such as to remove/add amino acids capable of disulfide bonding, to increase its bio-longevity, to alter its secretory characteristics, etc. In addition, it may be desirable to improve the binding affinity between the binding molecules; it may also be desirable to improve other biological properties of the binding molecules, including but not limited to specificity, thermostability, expression level, or solubility. Thus, in addition to the binding molecules described herein, it is contemplated that variants can be prepared.

In some embodiments, a binding molecule variant comprising an amino acid sequence that is at least about 75%, about 80%, about 85%, about 90%, about 91%, about 92%, about 93%, about 94%, about 95%, about 96%, about 97%, about 98%, or about 99% identical to the amino acid sequence of a binding molecule disclosed herein.

In some embodiments, the binding molecules provided herein are chemically modified, for example, by the covalent attachment of any type of molecule to the binding molecules. Exemplary non-limiting modifications include glycosylation, acetylation, pegylation, phosphorylation, amidation, derivatization by known protecting/blocking groups, proteolytic cleavage, linkage to a cellular ligand or other protein, etc. Additionally, the binding molecules may contain one or more non-classical amino acids.

In some embodiments, variations may be a substitution, deletion, or insertion of one or more codons encoding the binding molecules that results in a change in the amino acid sequence as compared with the original sequence. The variation allowed may be determined by systematically making insertions, deletions, or substitutions of amino acids in the sequence and testing the resulting variants for activity exhibited by the full-length or mature native sequence.

Amino acid substitutions can be the result of replacing one amino acid with another amino acid having similar structural and/or chemical properties, such as the replacement of a leucine with a serine, e.g., conservative amino acid replacements. Standard techniques known to those of skill in the art can be used to introduce mutations in the nucleotide sequence encoding a molecule provided herein, including, for example, site-directed mutagenesis and PCR-mediated mutagenesis which results in amino acid substitutions.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g, tyrosine, phenylalanine, tryptophan, histidine). Table 3 below lists exemplary conservative amino acid substitutions. Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

TABLE 2

| Amino Acid Abbreviations | | |
|---|---|---|
| Amino Acid | Abbreviations | |
| Alanine | Ala | A |
| allosoleucine | AIle | |
| Arginine | Arg | R |
| asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 3

| Amino Acid Substitutions - Exemplary Conservative Substitutions | |
|---|---|
| Original AA | Conservative Substitution |
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial modifications in the biological properties of the binding molecule are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

Substitution, deletion or insertion of one or more (for example 2, 3 etc) CDR residues or omission of one or more (for example 2, 3 etc) CDRs is also contemplated. Antibodies have been described in the scientific literature in which one or two CDRs can be dispensed without loss of binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically.

Substitutions may be in the range of about 1 to 100 amino acids. In some embodiments, the substitution includes fewer than about 100 amino acid substitutions, fewer than about 95 amino acid substitutions, fewer than about 90 amino acid substitutions, fewer than about 85 amino acid substitutions, fewer than about 80 amino acid substitutions, fewer than about 75 amino acid substitutions, fewer than about 70 amino acid substitutions, fewer than about 65 amino acid substitutions, fewer than about 50 amino acid substitutions, fewer than about 45 amino acid substitutions, fewer than about 40 amino acid substitutions, fewer than about 35 amino acid substitutions, fewer than about 30 amino acid substitutions, fewer than about 25 amino acid substitutions, fewer than about 20 amino acid substitutions, fewer than about 15 amino acid substitutions, fewer than about 10 amino acid substitutions, fewer than about 5 amino acid substitutions, fewer than about 4 amino acid substitutions, fewer than about 3 amino acid substitutions, or fewer than about 2 amino acid substitutions relative to the original binding molecule.

Amino acid sequence insertions include amino- and/or carboxyl-terminal fusions ranging in length from 1 residue to polypeptides containing 100 or more residues, as well as intrasequence insertions of single or multiple amino acid residues. Examples of terminal insertions include a binding molecule with an N-terminal methionyl residue. Other insertional variants of the binding molecule include the fusion to the N or C terminus of the binding molecule to an enzyme (e.g., for antibody-directed enzyme prodrug therapy) or a polypeptide which increases the serum half-life of the binding molecule.

In some embodiments, the insertion is about 1 amino acid to about 20 amino acids long. In some embodiments, the insertion is at least about 1 amino acid. In some embodiments, the insertion is at most about 20 amino acid. In some embodiments, the insertion is about 1 amino acid to about 5 amino acids, about 1 amino acid to about 10 amino acids, about 1 amino acid to about 20 amino acids, about 5 amino acids to about 10 amino acids, about 5 amino acids to about 20 amino acids, about 10 amino acids to about 20 amino acids. In some embodiments, the insertion is about 1 amino acid, about 5 amino acids, about 10 amino acids, or about 20 amino acids.

Amino acid sequence deletions include amino- and/or carboxyl-terminal deletions ranging in length from one residue to polypeptides containing a hundred or more residues, as well as intrasequence deletions of single or multiple amino acid residues.

In some embodiments, the deletion is about 1 amino acid to about 20 amino acids long. In some embodiments, the deletion is at least about 1 amino acid. In some embodiments, the deletion is at most about 20 amino acids. In some embodiments, the deletion is about 1 amino acid to about 5 amino acids, about 1 amino acid to about 10 amino acids, about 1 amino acid to about 20 amino acids, about 5 amino acids to about 10 amino acids, about 5 amino acids to about 20 amino acids, about 10 amino acids to about 20 amino acids. In some embodiments, the deletion is about 1 amino acid, about 5 amino acids, about 10 amino acids, or about 20 amino acids.

Molecules derived from antibodies disclosed herein are contemplated. A "molecule derived from an antibody" refers to a functional antigen-binding fragment of an antibody. It is a portion of an antibody heavy and/or light chain polypeptide that retains some or all of the binding activity of the antibody from which the fragment was derived. Non-limiting examples of functional fragments include single-chain Fvs (scFv), Fab fragments, F(ab') fragments, F(ab)2 fragments, F(ab')2 fragments, disulfide-linked Fvs (dsFv), Fd fragments, Fv fragments, diabody, triabody, tetrabody, and minibody. Such functional antigen-binding fragment can be found in, for example, Harlow and Lane, Antibodies: A Laboratory Manual (1989); Mol. Biology and Biotechnology: A Comprehensive Desk Reference (Myers, ed., 1995); Huston, et al, 1993, Cell Biophysics 22:189-224; Pliickthun and Skerra, 1989, Meth. Enzymol. 178:497-515; and Day, Advanced Immunochemistry (2d ed. 1990).

Humanized, Human, and Recombinant Antibodies

The antibodies disclosed herein can comprise "chimeric" sequences in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, so long as they exhibit the desired biological activity (see U.S. Pat. No. 4,816,567; and Morrison, et al., Proc. Natl. Acad. Sci. USA, 1984, 81:6851-55).

The antibodies disclosed herein can be humanized antibodies. A humanized antibody can comprise human framework region and human constant region sequences. In some embodiments, one or more FR region residues of the human immunoglobulin are replaced by corresponding nonhuman residues. In some embodiments, humanized antibodies comprise residues that are not found in the recipient antibody or in the donor antibody. These modifications are made to further refine antibody performance.

Humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, Molecular Immunology, 1991, 28(4/5):489-498; Studnicka, et al, Protein Engineering, 1994, 7(6):805-814; and Roguska, et al., Proc. Natl. Acad. Sci. USA, 1994, 91:969-73), chain shuffling (U.S. Pat. No. 5,565,332), and techniques disclosed in, e.g., U.S. Pat. Nos. 6,407,213, 5,766,886, WO 93/17105; Tan, et al., J. Immunol., 2002, 169:1119-25; Caldas, et al, Protein Eng., 2000, 13(5):353-60; Morea et al, Methods, 2000, 20(3):267-79, Baca, et al., J. Biol. Chem., 1997, 272(16): 10678-84; Roguska, et al, Protein Eng., 1996, 9(10):895 904; Couto, et al, Cancer Res., 1995, 55 (23 Supp):5973s-5977s; Couto, et al, Cancer Res., 1995, 55(8): 1717-22; Sandhu, J. S., Gene, 1994, 150(2): 409-10 and Pedersen, et al, J. Mol. Biol., 1994, 235(3):959-73. See also U.S. Patent Pub. No. US 2005/0042664 A1 (Feb. 24, 2005), each of which is incorporated by reference herein in its entirety. In some embodiments, the humanized antibodies are constructed by CDR grafting, in which the amino acid sequences of the six CDRs of the parent non-human antibody (e.g., rodent) are grafted onto a human antibody framework. For example, Padlan, et al. determined that only about one third of the residues in the CDRs contact the antigen, and termed these the "specificity determining residues," or SDRs (Padlan, et al, FASEB J., 1995, 9: 133-9). In the technique of SDR grafting, only the SDR residues are grafted onto the human antibody framework (see, e.g., Kashmiri, et al, Methods, 2005, 36:25-34).

The choice of human variable domains, both light and heavy, to be used in making humanized antibodies can be important to reduce antigenicity. For example, according to the so-called "best-fit" method, the sequence of the variable domain of a non-human (e.g., rodent) antibody is screened against the entire library of known human variable-domain sequences. The human sequence that is closest to that of the rodent may be selected as the human framework for the humanized antibody (Sims et al, J. Immunol., 1993, 151: 2296-308; and Chothia et al., J. Mol. Biol., 1987, 196:901-17).

Another method uses a particular framework derived from the consensus sequence of all human antibodies of a particular subgroup of light or heavy chains. The same framework may be used for several different humanized antibodies (Carter et al, Proc. Natl. Acad. Sci. USA, 1992, 89:4285-89; and Presta et al, J Immunol., 1993, 151:2623-32). In some embodiments, the framework is derived from the consensus sequences of the most abundant human subclasses, VL6 subgroup I (VL6I) and VH subgroup III (VHIII).

In an alternative method based on comparison of CDRs, called superhumanization, FR homology is irrelevant. The method consists of comparison of the non-human sequence with the functional human germline gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs (see, e.g., Tan et al., J. Immunol., 2002, 169:1119-25).

Another method for antibody humanization is based on a metric of antibody humanness termed Human String Content (HSC). This method compares the mouse sequence with the repertoire of human germline genes, and the differences are scored as HSC. The target sequence is then humanized by maximizing its HSC rather than using a global identity measure to generate multiple diverse humanized variants (Lazar et al., Mol. Immunol., 2007, 44:1986-98).

In addition to the methods described above, empirical methods may be used to generate and select humanized antibodies. These methods include those that are based upon the generation of large libraries of humanized variants and selection of the best clones using enrichment technologies or high throughput screening techniques. Antibody variants may be isolated from phage, ribosome, and yeast display libraries as well as by bacterial colony screening (see, e.g., Hoogenboom, Nat. Biotechnol., 2005, 23:1105-16; Dufner, et ah, Trends Biotechnol., 2006, 24:523-9; Feldhaus, et al., Nat. Biotechnol, 2003, 21:163-70; and Schlapschy et al, Protein Eng. Des. Sel, 2004, 17:847-60).

In the FR library approach, a collection of residue variants are introduced at specific positions in the FR followed by screening of the library to select the FR that best supports the grafted CDR. The residues to be substituted may include some or all of the "Vernier" residues identified as potentially contributing to CDR structure (see, e.g., Foote and Winter, J. Mol. Biol., 1992, 224:487-99), or from the more limited set of target residues identified by Baca, et al, J. Biol. Chem., 1997, 272:10678-84.

In FR shuffling, whole FRs are combined with the non-human CDRs instead of creating combinatorial libraries of selected residue variants (see, e.g., DalTAcqua et al, Methods, 2005, 36:43-60). The libraries may be screened for binding in a two-step process, first humanizing VL, followed by VH. Alternatively, a one-step FR shuffling process may be used. Such a process has been shown to be more efficient than the two-step screening, as the resulting antibodies exhibited improved biochemical and physicochemical properties including enhanced expression, increased affinity, and thermal stability (see, e.g., Damschroder, et al., Mol. Immunol., 2007, 44:3049-60).

The "humaneering" method is based on experimental identification of essential minimum specificity determinants (MSDs) and is based on sequential replacement of non-human fragments into libraries of human FRs and assessment of binding. It begins with regions of the CDR3 of non-human VH and VL chains and progressively replaces other regions of the non-human antibody into the human FRs, including the CDR1 and CDR2 of both VH and VL. This methodology typically results in epitope retention and identification of antibodies from multiple subclasses with distinct human V-segment CDRs. Humaneering allows for isolation of antibodies that are 91-96% homologous to human germline gene antibodies (see, e.g., Alfenito, Cambridge Healthtech Institute's Third Annual PEGS, The Protein Engineering Summit, 2007).

The "human engineering" method involves altering a non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human (e.g., mouse) antibody as "low risk," "moderate risk," or "high risk" residues. The classification is performed using a global risk/reward calculation that evaluates the predicted benefits of making particular substitution (e.g., for immunogenicity in humans) against the risk that the substitution will affect the resulting antibody's folding. The particular human amino acid residue to be substituted at a given position (e.g., low or moderate risk) of a non-human (e.g., mouse) antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al, Protein Engineering, 1994, 7:805-14; U.S. Pat. Nos. 5,766,886; 5,770,196; 5,821,123; and 5,869,619; and PCT Publication WO 93/11794.

The antibodies disclosed herein can be composite human antibodies. A composite human antibody can be generated using, for example, Composite Human Antibody™ technology (Antitope Ltd., Cambridge, United Kingdom). To generate composite human antibodies, variable region sequences are designed from fragments of multiple human antibody variable region sequences in a manner that avoids T cell epitopes, thereby minimizing the immunogenicity of the resulting antibody. Such antibodies can comprise human constant region sequences, e.g., human light chain and/or heavy chain constant regions.

The antibodies disclosed herein can be deimmunized. A deimmunized antibody is an antibody in which T-cell epitopes have been removed. Methods for making deimmunized antibodies have been described (see, e.g., Jones, et al., Methods Mol Biol., 2009, 525:405-23; and De Groot, et al., Cell. Immunol., 2006, 244:148-153). Deimmunized antibodies comprise T-cell epitope-depleted variable regions and human constant regions. Briefly, VH and VL of an antibody are cloned and T-cell epitopes are subsequently identified by testing overlapping peptides derived from the VH and VL of the antibody in a T cell proliferation assay. T cell epitopes are identified via in silico methods to identify peptide binding to human MHC class II. Mutations are introduced in the VH and VL to abrogate binding to human MHC class II. Mutated VH and VL are then utilized to generate the deimmunized antibody.

It is further generally desirable that antibodies be humanized with retention of their affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. These include, for example, WAM (Whitelegg and Rees, Protein Eng., 2000, 13:819-24), Modeller (Sali and Blundell, J. Mol. Biol., 1993, 234:779-815), and Swiss PDB Viewer (Guex and Peitsch, Electrophoresis, 1997, 18:2714-23). Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

The antibodies disclosed herein can be fully human antibodies, which possess an amino acid sequence corresponding to that of an antibody produced by a human. This definition of a human antibody specifically excludes a humanized antibody comprising non-human antigen-binding residues. Human antibodies can be produced using various techniques known in the art, including phage-display libraries (Hoogenboom and Winter, J. Mol. Biol, 1991, 227:381; Marks, et al, 1991, J. Mol. Biol., 1991, 222:581) and yeast display libraries (Chao, et al, Nature Protocols, 2006, 1: 755-68). Also available for the preparation of human monoclonal antibodies are methods described in Cole, et al., Monoclonal Antibodies and Cancer Therapy 77 (1985): Boerner, et al., J. Immunol., 1991, 147(1):86-95; and van Dijk and van de Winkel, Curr. Opin. Pharmacol, 2001, 5: 368-74. Human antibodies can also be prepared by administering the antigen to a transgenic animal that has been modified to produce such antibodies in response to antigenic challenge, but whose endogenous loci have been disabled, e.g., mice (see, e.g., Jakobovits, Curr. Opin. Biotechnol., 1995, 6(5):561-66; Bruggemann and Taussing, Curr. Opin. Biotechnol., 1997, 8(4):455-58; and U.S. Pat. Nos. 6,075,181 and 6,150,584 regarding XENOMOUSE™ technology). See also, for example, Li, et al., Proc. Natl. Acad. Sci. USA, 2006, 103:3557-62, regarding human antibodies generated via a human B-cell hybridoma technology.

The antibodies disclosed herein can be recombinant human antibodies, which are human antibodies prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see e.g., Taylor, L. D., et al, Nucl. Acids Res., 199220:6287-6295) or antibodies prepared, expressed, created or isolated by any other means that involves splicing of human immunoglobulin gene sequences to other DNA sequences. In some embodiments, such recombinant human antibodies can have variable and constant regions derived from human germline immunoglobulin sequences (See Kabat, E. A., et al. (1991) Sequences of Proteins of Immunological Interest Fifth Edition, U.S. Department of Health and Human Services, NIH Publication No. 91-3242). In some embodiments, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Monoclonal Antibody Manufacturing

Monoclonal antibodies or functional fragments thereof (e.g., antigen-binding fragment thereof) may be made using, for example, the hybridoma method or the phage display method.

In the hybridoma method (see, e.g., described in Kohler, et al., Nature, 1975, 256:495-7), a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice 59-103 (1986)).

The hybridoma cells thus prepared are seeded and grown in a suitable culture medium, which, in some embodiments, contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which prevent the growth of HGPRT-deficient cells.

Exemplary parental myeloma cells are those that fuse efficiently, support stable high-level production of antibody by the selected antibody-producing cells, and are sensitive to a selective medium that selects against the unfused parental cells. Exemplary myeloma cell lines are murine myeloma lines, such as SP-2 and derivatives, for example, X63-Ag8-653 cells available from the American Type Culture Collection (Manassas, VA), and those derived from MOPC-21 and MPC-11 mouse tumors available from the Salk Institute Cell Distribution Center (San Diego, CA). Human myeloma and mouse-human heteromyeloma cell lines also have been described for the production of human monoclonal antibodies (Kozbor, Immunol. 1984, 133:3001-05; and Brodeur, et al., Monoclonal Antibody Production Techniques and Applications, 1987, 51-63).

Culture medium in which hybridoma cells are growing is assayed for production of monoclonal antibodies directed against the antigen. The binding specificity of monoclonal antibodies produced by hybridoma cells is determined by immunoprecipitation or by an in vitro binding assay, such as RIA or ELISA. The binding affinity of the monoclonal antibody can, for example, be determined by the Scatchard analysis described in Munson et al, Anal. Biochem., 1980, 107:220-39.

Once hybridoma cells that produce antibodies of the desired specificity, affinity, and/or activity are identified, the clones may be subcloned by limiting dilution procedures and grown by standard methods (Goding, supra). Suitable culture media for this purpose include, for example, DMEM or RPMI-1640 medium. In addition, the hybridoma cells may be grown in vivo as ascites tumors in an animal, for example, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

In the phage display method, synthetic antibody clones are selected by screening phage libraries containing phages that display various fragments of antibody variable region (Fv) fused to phage coat protein. Such phage libraries are screened against the desired antigen. Clones expressing Fv fragments capable of binding to the desired antigen are adsorbed to the antigen and thus separated from the non-binding clones in the library. The binding clones are then eluted from the antigen and can be further enriched by additional cycles of antigen absorption/elution.

Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described, for example, in Winter et al, 1994, Ann. Rev. Immunol. 12:433-55.

Repertoires of VH and VL genes can be separately cloned by PCR and recombined randomly in phage libraries, which can then be searched for antigen-binding clones as described in Winter et al, supra. Libraries from immunized sources provide high-affinity antibodies to the antigen without the requirement of constructing hybridomas. Alternatively, naive libraries can be cloned to provide a single source of human antibodies to a wide range of non-self and self antigens without any immunization as described by Griffiths et al, EMBO J, 1993, 12:725-34. Finally, naive libraries can also be made synthetically by cloning the unrearranged V-gene segments from stem cells, and using PCR primers containing random sequence to encode the highly variable CDR3 regions and to accomplish rearrangement in vitro as described, for example, by Hoogenboom and Winter, J. Mol. Biol., 1992, 227:381-88.

Screening of the libraries can be accomplished by various techniques known in the art. For example, the antigen can be used to coat the wells of adsorption plates, expressed on host cells affixed to adsorption plates or used in cell sorting, conjugated to biotin for capture with streptavidin-coated beads, or used in any other method for panning display libraries. The selection of antibodies with slow dissociation kinetics (e.g, good binding affinities) can be promoted by use of long washes and monovalent phage display as described in Bass, et al, Proteins, 1990, 8:309-14 and WO 92/09690, and by use of a low coating density of antigen as described in Marks et al, BiotechnoL, 1992, 10:779-83.

Exemplary phage display methods that can be used herein include those disclosed in Antibody Phage Display: Methods and Protocols (O'Brien and Aitken, eds., 2002); Brinkman, et al, J. Immunol. Methods, 1995, 182:41-50; Ames, et al, Immunol. Methods, 1995, 184:177-86; Kettleborough, et al., Eur. J. Immunol., 1994, 24:952-8; Persic, et al, Gene, 1997, 187:9-18; Burton et al., Advances in Immunology, 1994, 57:191-280; PCT Application No. PCT/GB91/01 134; International Publication Nos. WO 90/02809, WO 91/10737, WO 92/01047, WO 92/18619, WO 93/1 1236, WO 95/15982, WO 95/20401, and WO097/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

DNA encoding the monoclonal antibodies is readily isolated from the hybridoma cells and the screened libraries. Such DNA can be sequenced using conventional procedures (e.g., by using oligonucleotide probes that are capable of binding specifically to genes encoding the heavy and light chains of murine antibodies). Once isolated, the DNA may be placed into expression vectors, which are then transfected into host cells, such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody includes Skerra, et al, Curr. Opinion in Immunol., 1993, 5:256-62 and Pluckthun, Immunol. Revs., 1992, 130:151-88.

Once an antibody molecule provided herein has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies provided herein can be fused to heterologous polypeptide sequences described herein or otherwise known in the art to facilitate purification.

Polynucleotides

Provided herein is a polynucleotide encoding the binding molecule disclosed herein.

Polynucleotides disclosed herein can be at least about 5, at least about 10, at least about 15, at least about 20, at least about 25, at least about 30, at least about 40, at least about 50, at least about 100, at least about 200, at least about 300, at least about 400, at least about 500, at least about 1000, at least about 5000, at least about 10000, or at least about 15000 or more nucleotides in length, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc.

The present disclosure further relates to variants of the polynucleotides disclosed herein. The polynucleotide variants can contain alterations in the coding regions, non-coding regions, or both.

In some embodiments, a polynucleotide variant comprising a nucleotide sequence that is at least about 75%, about 80%, about 85%, about 90%, about 91%, about 92%, about 93%, about 94%, about 95%, about 96%, about 97%, about 98%, or about 99% identical to the nucleotide sequence of a polynucleotide disclosed herein.

In some embodiments, a polynucleotide variant contains substitutions, additions, or deletions that alter the properties or activities of the encoded polypeptide. In some embodiments, a polynucleotide variant contains silent substitutions, additions, or deletions that does not alter the properties or activities of the encoded polypeptide. In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, polynucleotides are codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, (xi) isolated removal of spurious translation initiation sites and/or (xii) elimination of fortuitous polyadenylation sites otherwise leading to truncated RNA transcripts.

It will be appreciated by those of ordinary skill in the art that, as a result of the degeneracy of the genetic code, there are many nucleotide sequences that encode a polypeptide, or fragment of variant thereof, as described herein. Some of these polynucleotides bear minimal homology to the nucleotide sequence of any native gene. Nonetheless, polynucleotides that vary due to differences in codon usage are specifically contemplated in particular embodiments, for example polynucleotides that are optimized for human and/or primate codon selection. Further, alleles of the genes comprising the polynucleotide sequences provided herein may also be used. Alleles are endogenous genes that are altered as a result of one or more mutations, such as deletions, additions and/or substitutions of nucleotides.

The polynucleotides contemplated herein, regardless of the length of the coding sequence itself, may be combined with other DNA sequences, such as promoters and/or enhancers, untranslated regions (UTRs), signal sequences, Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed in particular embodiments, with the total length preferably being limited by the ease of preparation and use in the intended recombinant DNA protocol.

Polynucleotides can be prepared, isolated, purified, manipulated, and/or expressed using any of a variety of well-established techniques known and available in the art.

Vectors

Provided herein are vectors comprising the polynucleotides or nucleic acid molecules disclosed herein.

In order to express binding molecule described herein in a cell, an expression cassette encoding the monoclonal antibody or antigen-binding fragment thereof can be inserted into a nucleic acid vector. The "expression cassette" contains the gene of interest. The cassette is positionally and sequentially oriented within the vector such that the nucleic acid in the cassette can be transcribed into RNA, and when necessary, translated into a protein or a polypeptide, undergo appropriate post-translational modifications required for activity in the host cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. The cassette can be removed and inserted into a plasmid or viral vector as a single unit.

The host cell may be co-transfected with two vectors provided herein, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature, 1986, 322:52; and Kohler, Proc. Natl. Acad. Sci. USA, 1980, 77:2197-9).

In some embodiments, vectors include, without limitation, plasmids, phagemids, cosmids, transposons, artificial chromosomes such as yeast artificial chromosome (YAC), bacterial artificial chromosome (BAC), or P1-derived artificial chromosome (PAC), bacteriophages such as lambda phage or M13 phage, and animal viruses. In some embodiments, the coding sequences of the monoclonal antibody or antigen-binding fragment thereof disclosed herein can be ligated into such vectors for expression in mammalian cells.

In some embodiments, non-viral vectors are used to deliver one or more polynucleotides contemplated herein. In some embodiments, the recombinant vector comprising a polynucleotide encoding the monoclonal antibody or antigen-binding fragment thereof described herein is a plasmid. Numerous suitable plasmid expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other plasmid vector may be used so long as it is compatible with the host cell.

In some embodiments, viral vectors are used to deliver one or more polynucleotides contemplated herein. Suitable viral vectors include, but are not limited to, viral vectors based on adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., U.S. Pat. No. 7,078,387; Ali et al., Hum Gene Ther 9:81 86, 1998, Flannery et al,, PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al,, Virol. (1988) 166:154-165; and Flotte et al., PNAS (1993) 90:10613-10617); alphaviruses; arenaviruses; baculovirus; herpes simplex virus; human immunodeficiency virus (see, e.g., Miyoshi et al., PNAS 94:10319 23, 1997; Takahashi et al., J Virol 73:7812 7816, 1999); poliovirus; poxvirus; retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); SV40; vaccinia virus; and the like. Examples of vectors are pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells.

In some embodiments, the vector is a non-integrating vector, including but not limited to, an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally. The vector is engineered to harbor the sequence coding for the origin of DNA replication or "ori" from a lymphotrophic herpes virus or a gamma herpesvirus, an adenovirus, SV40, a bovine papilloma virus, or a yeast, specifically a replication origin of a lymphotrophic herpes virus or a gamma herpesvirus corresponding to oriP of EBV. In some embodiments, the lymphotrophic herpes virus may be Epstein Barr virus (EBV), Kaposi's sarcoma herpes virus (KSHV), Herpes virus saimiri (HS), or Marek's disease virus (MDV). Epstein Barr virus (EBV) and Kaposi's sarcoma herpes virus (KSHV) are also examples of a gamma herpesvirus. A viral vector delivered by such viruses or viral particles may be referred to by the type of virus to deliver the viral vector (e.g., a lentiviral vector is a viral vector that is to be delivered by a lentivirus). A viral vector can contain viral elements (e.g., nucleotide sequences) necessary for packaging of the viral vector into the virus or viral particle, replicating the virus, or other desired viral activities. A virus containing a viral vector may be replication competent, replication deficient or replication defective.

In some embodiments, the vector is an integrating vector. In some embodiments, a polynucleotide is introduced into a target or host cell using a transposon vector system. In some embodiments, the transposon vector system comprises a vector comprising transposable elements and a polynucleotide contemplated herein; and a transposase. In some embodiments, the transposon vector system is a single transposase vector system, see, e.g., WO 2008/027384. Exemplary transposases include, but are not limited to: piggyBac, Sleeping Beauty, Mos1, Tc1/mariner, Tol2, mini-Tol2, Tc3, MuA, Himar I, Frog Prince, and derivatives thereof. The piggyBac transposon and transposase are described, for example, in U.S. Pat. No. 6,962,810, which is incorporated herein by reference in its entirety. The Sleeping Beauty transposon and transposase are described, for example, in Izsvak et al., J. Mol. Biol. 302: 93-102 (2000), which is incorporated herein by reference in its entirety. The Tol2 transposon which was first isolated from the medaka fish Oryzias latipes and belongs to the hAT family of transposons is described in Kawakami et al. (2000). Mini-Tol2 is a variant of Tol2 and is described in Balciunas et al. (2006). The Tol2 and Mini-Tol2 transposons facilitate integration of a transgene into the genome of an organism when co-acting with the Tol2 transposase. The Frog Prince transposon and transposase are described, for example, in Miskey et al., Nucleic Acids Res. 31:6873-6881 (2003).

In some embodiments, a polynucleotide sequence encoding the monoclonal antibody or antigen-binding fragment thereof disclosed herein is operably linked to one or more control elements that allow expression of the polynucleotide in both prokaryotic and eukaryotic cells. "Control elements" refer those non-translated regions of the vector which interact with host cellular proteins to carry out transcription and translation. Non-limiting examples of control elements include origin of replication, selection cassettes, constitutive and inducible promoters, enhancers, translation initiation signals (Shine Dalgarno sequence or Kozak sequence) introns, transcription terminators, 5' and 3' untranslated regions. See e.g., Bitter et al. (1987) Methods in Enzymology, 153:516-544) Such elements may vary in their strength and specificity. The transcriptional control element may be functional in either a eukaryotic cell (e.g., a mammalian cell) or a prokaryotic cell (e.g., bacterial or archaeal cell).

In some embodiments, polynucleotides encoding the monoclonal antibody or antigen-binding fragment thereof described herein are operably linked to a promoter and/or an enhancer. The term "promoter" as used herein refers to a recognition site of a polynucleotide (DNA or RNA) to which an RNA polymerase binds. An RNA polymerase initiates and transcribes polynucleotides operably linked to the promoter. In some embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide. The term "enhancer" refers to a segment of DNA which contains sequences capable of providing enhanced transcription and in some instances can function independent of their orientation relative to another control sequence. An enhancer can function cooperatively or additively with promoters and/or other enhancer elements.

Non-limiting examples of suitable eukaryotic promoters (promoters functional in a eukaryotic cell) include those from cytomegalovirus (CMV) immediate early, herpes simplex virus (HSV) thymidine kinase, a viral simian virus 40 (SV40) (e.g., early and late SV40), a spleen focus forming virus (SFFV) promoter, long terminal repeats (LTRs) from retrovirus (e.g., a Moloney murine leukemia virus (MoMLV) LTR promoter or a Rous sarcoma virus (RSV) LTR), a herpes simplex virus (HSV) (thymidine kinase) promoter, H5, P7.5, and P11 promoters from vaccinia virus, an elongation factor 1-alpha (EF1$\alpha$) promoter, early growth response 1 (EGR1) promoter, a ferritin H (FerH) promoter, a ferritin L (FerL) promoter, a Glyceraldehyde 3-phosphate dehydrogenase (GAPDH) promoter, a eukaryotic translation initiation factor 4A1 (EIF4A1) promoter, a heat shock 70 kDa protein 5 (HSPA5) promoter, a heat shock protein 90 kDa beta, member 1 (HSP90B1) promoter, a heat shock protein 70 kDa (HSP70) promoter, a $\beta$-kinesin ($\beta$-KIN) promoter, the human ROSA 26 locus (Irions et al., Nature Biotechnology 25, 1477-1482 (2007)), a Ubiquitin C (UBC) promoter, a phosphoglycerate kinase-1 (PGK) promoter, a cytomegalovirus enhancer/chicken $\beta$-actin (CAG) promoter, a $\beta$-actin promoter and a myeloproliferative sarcoma virus enhancer, negative control region deleted, dl587rev primer-binding site substituted (MND) promoter, and mouse metallothionein-1. Selection of the appropriate vector and promoter is well within the level of ordinary skill in the art.

In some embodiments, a polynucleotide sequence encoding the monoclonal antibody or antigen-binding fragment thereof described herein is operably linked to a constitutive promoter. In such embodiments, the polynucleotides encoding the monoclonal antibody or antigen-binding fragment thereof described herein are constitutively and/or ubiquitously expressed in a cell.

In some embodiments, a polynucleotide sequence encoding the monoclonal antibody or antigen-binding fragment thereof described herein is operably linked to an inducible promoter. In such embodiments, polynucleotides encoding the monoclonal antibody or antigen-binding fragment thereof described herein are conditionally expressed. As used herein, "conditional expression" may refer to any type of conditional expression including, but not limited to, inducible expression; repressible expression; expression in cells or tissues having a particular physiological, biological, or disease state (e.g., cell type or tissue specific expression) etc. Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, Gene, 323:67), the cumate inducible gene switch (WO 2002/088346), tetracycline-dependent regulatory systems, etc.

In some embodiments, the vectors described herein further comprise a transcription termination signal. Elements directing the efficient termination and polyadenylation of the heterologous nucleic acid transcripts increase heterologous gene expression. Transcription termination signals are generally found downstream of the polyadenylation signal. In some embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In some embodiments, the core poly(A) sequence is an ideal polyA sequence (e.g., AATAAA, ATTAAA, AGTAAA). In some embodiments, the poly(A) sequence is an SV40 polyA sequence, a bovine growth hormone polyA sequence (BGHpA), a rabbit β-globin polyA sequence (rβgpA), variants thereof, or another suitable heterologous or endogenous polyA sequence known in the art.

The expression vector may also include nucleotide sequences encoding protein tags (e.g., 6×His tag, hemagglutinin tag, green fluorescent protein, etc.) that are fused to the site-directed modifying polypeptide, thus resulting in a chimeric polypeptide.

Methods of introducing polynucleotides and recombinant vectors into a host cell are known in the art. Suitable methods include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al., Adv Drug Deliv Rev. 2012 Sep. 13. pii: S0169-409X(12)00283-9), microfluidics delivery methods (See e.g., International PCT Publication No. WO 2013/059343), and the like.

In some embodiments, delivery via electroporation comprises mixing the cells with the polynucleotides encoding the binding molecuke in a cartridge, chamber, or cuvette and applying one or more electrical impulses of defined duration and amplitude. In some embodiments, cells are mixed with polynucleotides encoding the binding molecule in a vessel connected to a device (e.g., a pump) which feeds the mixture into a cartridge, chamber, or cuvette wherein one or more electrical impulses of defined duration and amplitude are applied, after which the cells are delivered to a second vessel. Illustrative examples of polynucleotide delivery systems suitable for use in particular embodiments contemplated include, but are not limited to, those provided by Amaxa Biosystems, Maxcyte, Inc., BTX Molecular Delivery Systems, Neon™ Transfection Systems, and Copernicus Therapeutics Inc. Lipofection reagents are sold commercially (e.g., Transfectam™ and Lipofectin™). Cationic and neutral lipids that are suitable for efficient lipofection of polynucleotides have been described in the literature. See e.g., Liu et al. (2003) Gene Therapy. 10:180-187; and Balazs et al. (2011) Journal of Drug Delivery. 2011:1-12.

In some embodiments, polynucleotides encoding the monoclonal antibody or antigen-binding fragment thereof described herein are introduced to a cell in a non-viral delivery vehicle, such as a transposon, a nanoparticle (e.g., a lipid nanoparticle), a liposome, an exosome, an attenuated bacterium, or a virus-like particle. In some embodiments, the vehicle is an attenuated bacterium (e.g., naturally or artificially engineered to be invasive but attenuated to prevent pathogenesis including *Listeria monocytogenes*, certain *Salmonella* strains, *Bifidobacterium longum*, and modified *Escherichia coli*), bacteria having nutritional and tissue-specific tropism to target specific cells, and bacteria having modified surface proteins to alter target cell specificity. In some embodiments, the vehicle is a genetically modified bacteriophage (e.g., engineered phages having large packaging capacity, less immunogenicity, containing mammalian plasmid maintenance sequences and having incorporated targeting ligands). In some embodiments, the vehicle is a biological liposome. For example, the biological liposome is a phospholipid-based particle derived from human cells (e.g., erythrocyte ghosts, which are red blood cells broken down into spherical structures derived from the subject and wherein tissue targeting can be achieved by attachment of various tissue or cell-specific ligands), secretory exosomes, or subjectderived membrane-bound nanovescicles (30-100 nm) of endocytic origin (e.g., can be produced from various cell types and can therefore be taken up by cells without the need for targeting ligands).

In some embodiments, vectors comprising polynucleotides encoding the binding molecule described herein are introduced to cells by viral delivery methods, e.g., by viral transduction. A number of viral based systems have been developed for gene transfer into mammalian cells. For example, retroviruses provide a convenient platform for gene delivery systems. The heterologous nucleic acid can be inserted into a vector and packaged in retroviral particles using techniques known in the art. The recombinant virus can then be isolated and delivered to the engineered mammalian cell in vitro or ex vivo. A number of retroviral systems are known in the art. In some embodiments, adenovirus vectors are used. A number of adenovirus vectors are known in the art. In some embodiments, lentivirus vectors are used. In some embodiments, self-inactivating lentiviral vectors are used. For example, self-inactivating lentiviral vectors carrying the immunomodulator (such as immune checkpoint inhibitor) coding sequence and/or self-inactivating lentiviral vectors carrying chimeric antigen receptors can be packaged with protocols known in the art. The resulting lentiviral vectors can be used to transduce a mammalian cell (such as primary human T cells) using methods known in the art. Vectors derived from retroviruses such as lentivirus are suitable tools to achieve long-term gene transfer, because they allow long-term, stable integration of a transgene and its propagation in progeny cells. Lentiviral vectors also have low immunogenicity, and can transduce nonproliferating cells.

In some embodiments, the vehicle is a mammalian virus-like particle. For example, modified viral particles can be generated (e.g., by purification of the "empty" particles followed by ex vivo assembly of the virus with the desired cargo).

Compositions

Provided herein is a pharmaceutical composition comprising the binding molecule, the polynucleotide, and/or the vector disclosed herein.

In some embodiments, the pharmaceutical composition comprises at least one binding molecule present in solution at a concentration of about 1 mg/mL to about 100 mg/mL (e.g., 1, 5, 10, 15, 20, 25, 30, 35, 40, 45, 50, 55, 60, 65, 70, 75, 80, 85, 90, 95, or 100 mg/mL). In some embodiments, the binding molecule is present at a concentration of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL, about 62 mg/mL, about 63 mg/mL, about 64 mg/mL, about 65 mg/mL, about 66 mg/mL, about 67 mg/mL, about 68 mg/mL, about 69 mg/mL, about 70 mg/mL, about 71 mg/mL, about 72 mg/mL, about 73 mg/mL, about 74 mg/mL, about 75 mg/mL, about 76 mg/mL, about 77 mg/mL, about 78 mg/mL, about 79 mg/mL, about 80 mg/mL, about 81 mg/mL, about 82 mg/mL, about 83 mg/mL, about 84 mg/mL, about 85 mg/mL, about 86 mg/mL, about 87 mg/mL, about 88 mg/mL, about 89 mg/mL, about 90 mg/mL, about 91 mg/mL, about 92 mg/mL, about 93 mg/mL, about 94 mg/mL, about 95 mg/mL, about 96 mg/mL, about 97 mg/mL, about 98 mg/mL, about 99 mg/mL, or about 100 mg/mL including all ranges, subranges and values therebetween. In some embodiments, the binding molecule is present at a concentration of about 20 mg/mL to about 40 mg/mL, about 25 mg/mL to about 40 mg/mL, about 30 mg/mL to about 40 mg/mL, about 20 mg/mL to about 35 mg/mL, about 25 mg/mL to about 35 mg/mL, about 30 mg/mL to about 35 mg/mL, about 20 mg/mL to about 30 mg/mL or about 25 mg/mL to about 30 mg/mL. In some embodiments, the binding molecule is present at a concentration of from 25 mg/ml to about 31 mg/mL. In some embodiments, the binding molecule is present at a concentration of about 30 mg/mL. In some embodiments, the binding molecule is present at a concentration of about 25 mg/mL. In some embodiments, the binding molecule is present at a concentration of about 31 mg/mL. In some embodiments, the binding molecule is present at a concentration of about 1 mg/mL to about 21 mg/mL, about 6 mg/mL to about 21 mg/mL, about 11 mg/mL to about 21 mg/mL, about 1 mg/mL to about 16 mg/mL, about 6 mg/mL to about 16 mg/mL, about 11 mg/mL to about 16 mg/mL, about 1 mg/mL to about 11 mg/mL or about 6 mg/mL to about 11 mg/mL. In some embodiments, the binding molecule is present at a concentration of about 11 mg/mL.

In some embodiments, the pharmaceutical composition comprises two components, wherein each component comprises the binding molecule, the polynucleotide, or the vector disclosed herein, wherein each component is different. In some embodiments, the pharmaceutical compositions comprise three components, wherein each component comprising the binding molecule, the polynucleotide, or the vector disclosed herein, wherein each component is different. In some embodiments, the pharmaceutical compositions comprise four components, wherein each component comprises the binding molecule, the polynucleotide, or the vector disclosed herein, wherein each component is different.

In some embodiments, the present disclosure provides compositions comprising one or more binding molecules, described herein. In some embodiments, the present disclosure provides compositions comprising 2 binding molecules, described herein. For example, in some embodiments, the present disclosure provides a composition comprising UDIZ-007 and UDIZ-008.

In some embodiments, the pharmaceutical composition further comprises a pharmaceutically acceptable carrier. In some embodiments, the pharmaceutical composition comprises at least two or more pharmaceutically acceptable carriers. In some embodiments, the pharmaceutical composition comprises at least three or more pharmaceutically acceptable carriers.

Pharmaceutically acceptable carrier, diluent or excipient includes, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, and/or emulsifier which has been approved by the United States Food and Drug Administration as being acceptable for use in humans and/or domestic animals. Exemplary pharmaceutically acceptable carriers include, but are not limited to, sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter; waxes; animal and vegetable fats; paraffins; silicones; bentonites; silicic acid; zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations. Except insofar as any conventional media and/or agent is incompatible with the agents of the present disclosure, its use in therapeutic compositions is contemplated. Supplementary active ingredients also can be incorporated into the compositions.

Pharmaceutically acceptable salt includes both acid and base addition salts. Pharmaceutically-acceptable salts include the acid addition salts (formed with the free amino groups of the protein) and which are formed with inorganic acids such as, for example, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, ptoluenesulfonic acid, trifluoroacetic acid, undecylenic acid, and the like. Salts formed with the free carboxyl groups can also be derived from inorganic bases such as, for example, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In some embodiments, the pharmaceutically acceptable carrier comprises a surfactant. In some embodiments, the surfactant comprises polysorbate-80. In some embodiments, the pharmaceutically acceptable carrier comprises at least one stabilizer. In some embodiments, the stabilizer comprises L-histidine and/or L-histidine monohydrate. In some embodiments, the pharmaceutically acceptable carrier comprises a sugar. In some embodiments, the sugar comprises mannitol. In some embodiments, the sugar comprises sucrose. In some embodiments, the at least one pharmaceutically acceptable carrier comprises polysorbate-80, L-histidine, L-histidine monohydrate, and mannitol. In some embodiments, the at least one pharmaceutically acceptable carrier comprises polysorbate-80, L-histidine, L-histidine monohydrate, and sucrose.

In some embodiments, the pharmaceutically acceptable carrier comprises L-histidine. In some embodiments, the pharmaceutical composition comprises L-histidine present in solution at a concentration of about 0.5 mg/mL to about 1 mg/mL (e.g., 0.5, 0.55, 0.6, 0.65, 0.7, 0.75, 0.8, 0.85, 0.9, 0.95 or 1 mg/mL). In some embodiments, the L-histidine is present at a concentration of about 0.5 mg/mL, about 0.51 mg/mL, 0.52 mg/mL, about 0.53 mg/mL, about 0.54 mg/mL, about 0.55 mg/mL, about 0.56 mg/mL, about 0.57 mg/mL, about 0.58 mg/mL, about 0.59 mg/mL, about 0.6 mg/mL, about 0.61 mg/mL, 0.62 mg/mL, about 0.63 mg/mL, about 0.64 mg/mL, about 0.65 mg/mL, about 0.66 mg/mL, about 0.67 mg/mL, about 0.68 mg/mL, about 0.69 mg/mL, about 0.7 mg/mL, about 0.71 mg/mL, 0.72 mg/mL, about 0.73 mg/mL, about 0.74 mg/mL, about 0.75 mg/mL, about 0.76 mg/mL, about 0.77 mg/mL, about 0.78 mg/mL, about 0.79 mg/mL, about 0.8 mg/mL, about 0.81 mg/mL, 0.82 mg/mL, about 0.83 mg/mL, about 0.84 mg/mL, about 0.85 mg/mL, about 0.86 mg/mL, about 0.87 mg/mL, about 0.88 mg/mL, about 0.89 mg/mL, about 0.9 mg/mL, about 0.91 mg/mL, 0.92 mg/mL, about 0.93 mg/mL, about 0.94 mg/mL, about 0.95 mg/mL, about 0.96 mg/mL, about 0.97 mg/mL, about 0.98 mg/mL, about 0.99 mg/mL, or 1 mg/mL, including all ranges, subranges and values therebetween. In some embodiments, the L-histidine is present at a concentration of about 0.65 mg/mL to about 0.85 mg/mL, about 0.70 mg/mL to about 0.85 mg/mL, about 0.75 mg/mL to about 0.85 mg/mL, about 0.65 mg/mL to about 0.80 mg/mL, about 0.70 mg/mL to about 0.80 mg/mL, about 0.75 mg/mL to about 0.80 mg/mL, about 0.65 mg/mL to about 0.75 mg/mL or about 0.70 mg/mL to about 0.75 mg/mL. In some embodiments, the L-histidine is present at a concentration of about 0.76 mg/mL.

In some embodiments, the pharmaceutically acceptable carrier comprises L-histidine monohydrate. In some embodiments, the pharmaceutical composition comprises L-histidine monohydrate present in solution at a concentration of about 1 mg/mL to about 2 mg/mL (e.g., 1.1, 1.2, 1.3, 1.4, 1.5, 1.6, 1.7, 1.8, 1.9, or 2 mg/mL). In some embodiments, the L-histidine monohydrate is present at a concentration of about 1 mg/mL, about 1.1 mg/mL, about 1.12 mg/mL, about 1.13 mg/mL, about 1.14 mg/mL, about 1.15 mg/mL, about 1.16 mg/mL, about 1.17 mg/mL, about 1.18 mg/mL, about 1.19 mg/mL, about 1.2 mg/mL, about 1.22 mg/mL, about 1.23 mg/mL, about 1.24 mg/mL, about 1.25 mg/mL, about 1.26 mg/mL, about 1.27 mg/mL, about 1.28 mg/mL, about 1.29 mg/mL, about 1.30 mg/mL, about 1.31 mg/mL, about 1.32 mg/mL, about 1.33 mg/mL, about 1.34 mg/mL, about 1.35 mg/mL, about 1.36 mg/mL, about 1.37 mg/mL, about 1.38 mg/mL, about 1.39 mg/mL, about 1.40 mg/mL, about 1.41 mg/mL, about 1.42 mg/mL, about 1.43 mg/mL, about 1.44 mg/mL, about 1.45 mg/mL, about 1.46 mg/mL, about 1.47 mg/mL, about 1.48 mg/mL, about 1.49 mg/mL, about 1.50 mg/mL, about 1.51 mg/mL, about 1.52 mg/mL, about 1.53 mg/mL, about 1.54 mg/mL, about 1.55 mg/mL, about 1.56 mg/mL, about 1.57 mg/mL, about 1.58 mg/mL, about 1.59 mg/mL, about 1.60 mg/mL, about 1.61 mg/mL, about 1.62 mg/mL, about 1.63 mg/mL, about 1.64 mg/mL, about 1.65 mg/mL, about 1.66 mg/mL, about 1.67 mg/mL, about 1.68 mg/mL, about 1.69 mg/mL, about 1.70 mg/mL, about 1.71 mg/mL, about 1.72 mg/mL, about 1.73 mg/mL, about 1.74 mg/mL, about 1.75 mg/mL, about 1.76 mg/mL, about 1.77 mg/mL, about 1.78 mg/mL, about 1.79 mg/mL, about 1.80 mg/mL, about 1.81 mg/mL, about 1.82 mg/mL, about 1.83 mg/mL, about 1.84 mg/mL, about 1.85 mg/mL, about 1.86 mg/mL, about 1.87 mg/mL, about 1.88 mg/mL, about 1.89 mg/mL, about 1.90 mg/mL, about 1.91 mg/mL, about 1.92 mg/mL, about 1.93 mg/mL, about 1.94 mg/mL, about 1.95 mg/mL, about 1.96 mg/mL, about 1.97 mg/mL, about 1.98 mg/mL, about 1.99 mg/mL or about 2.0 mg/mL, including all ranges, subranges and values therebetween. In some embodiments, the L-histidine monohydrate is present at a concentration of about 1 mg/mL to about 1.2 mg/mL, about 1.05 mg/mL to about 1.2 mg/mL, about 1.1 mg/mL to about 1.2 mg/mL, about 1 mg/mL to about 1.15 mg/mL, about 1.05 mg/mL to about 1.15 mg/mL, about 1.10 mg/mL to about 1.15 mg/mL, about 1 mg/mL to about 1.1 mg/mL or about 1.05 mg/mL to about 1.1 mg/mL. In some embodiments, the L-histidine monohydrate is present at a concentration of about 1.08 mg/mL.

In some embodiments, the pharmaceutically acceptable carrier comprises mannitol. In some embodiments, the pharmaceutical composition comprises mannitol present in solution at a concentration of about 20 mg/mL to about 40 mg/mL (e.g., 20, 25, 30, 35, or 40 mg/mL). In some embodiments, the mannitol is present at a concentration of about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, or about 40 mg/mL including all ranges, subranges and values therebetween. In some embodiments, the mannitol is present at a concentration of about 20 mg/mL to about 40 mg/mL, about 25 mg/mL to about 40 mg/mL, about 30 mg/mL to about 40 mg/mL, about 20 mg/mL to about 35 mg/mL, about 25 mg/mL to about 35 mg/mL, about 30 mg/mL to about 35 mg/mL, about 20 mg/mL to about 30 mg/mL or about 25 mg/mL to about 30 mg/mL. In some embodiments, the mannitol is present at a concentration of about 32 mg/mL. In other embodiments, the pharmaceutically acceptable carrier comprises sucrose. In some embodiments, the pharmaceutical composition comprises sucrose present in solution at a concentration of about 50 mg/mL to about 100 mg/mL (e.g., 50, 55, 60, 65, 70, 75, 80, 85, 90, 95 or 100 mg/mL including all ranges, subranges and values therebetween). For example, the sucrose is present at a concentration of about 50 mg/mL to about 100 mg/mL, about 55 mg/mL to about 95 mg/mL, about 60 mg/mL to about 90 mg/mL, about 65 mg/mL to about 85 mg/mL, about 70 mg/mL to about 80 mg/mL. In some embodiments, the sucrose is present at a concentration of about 80 mg/mL.

In some embodiments, the pharmaceutically acceptable carrier comprises polysorbate-80. In some embodiments, the pharmaceutical composition comprises polysorbate-80 present in solution at a concentration of about 0.5 mg/mL to about 1.5 mg/mL (e.g., 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45 or 1.5 mg/mL). In some embodiments, the polysorbate-80 is present at a concentration of about 0.5 mg/mL, about 0.51 mg/mL, 0.52 mg/mL, about 0.53 mg/mL, about 0.54 mg/mL, about 0.55 mg/mL, about 0.56 mg/mL, about 0.57 mg/mL, about 0.58 mg/mL, about 0.59 mg/mL, about 0.6 mg/mL, about 0.61 mg/mL, 0.62 mg/mL, about 0.63 mg/mL, about 0.64 mg/mL, about 0.65 mg/mL, about 0.66 mg/mL, about 0.67 mg/mL, about 0.68 mg/mL, about 0.69 mg/mL, about 0.7 mg/mL, about 0.71 mg/mL, 0.72 mg/mL, about 0.73 mg/mL, about 0.74 mg/mL, about 0.75 mg/mL, about 0.76 mg/mL, about 0.77 mg/mL, about 0.78 mg/mL, about 0.79 mg/mL, about 0.8 mg/mL, about 0.81 mg/mL, 0.82 mg/mL, about 0.83 mg/mL, about 0.84 mg/mL, about 0.85 mg/mL, about 0.86 mg/mL, about 0.87 mg/mL, about 0.88 mg/mL, about 0.89 mg/mL, about 0.9 mg/mL, about 0.91 mg/mL, 0.92 mg/mL, about 0.93 mg/mL, about 0.94 mg/mL, about 0.95 mg/mL, about 0.96 mg/mL, about 0.97 mg/mL, about 0.98 mg/mL, about 0.99 mg/mL, about 1 mg/mL, about 1.01 mg/mL, 1.02 mg/mL, about 1.03 mg/mL, about 1.04 mg/mL, about 1.05 mg/mL, about 1.06 mg/mL, about 1.07 mg/mL, about 1.08 mg/mL, about 1.09 mg/mL, about 1.1 mg/mL, about 1.11 mg/mL, 0.12 mg/mL, about 1.13 mg/mL, about 1.14 mg/mL, about 1.15 mg/mL, about 1.16 mg/mL, about 1.17 mg/mL, about 1.18 mg/mL, about 1.19 mg/mL, about 1.2 mg/mL, about 1.21 mg/mL, 1.22 mg/mL, about 1.23 mg/mL, about 1.24 mg/mL, about 1.25 mg/mL, about 1.26 mg/mL, about 1.27 mg/mL, about 1.28 mg/mL, about 1.29 mg/mL, about 1.3 mg/mL, about 1.31 mg/mL, 1.32 mg/mL, about 1.33 mg/mL, about 1.34 mg/mL, about 1.35 mg/mL, about 1.36 mg/mL, about 1.37 mg/mL, about 1.38 mg/mL, about 1.39 mg/mL, about 1.4 mg/mL, about 1.41 mg/mL, 1.42 mg/mL, about 1.43 mg/mL, about 1.44 mg/mL, about 1.45 mg/mL, about 1.46 mg/mL, about 1.47 mg/mL, about 1.48 mg/mL, about 1.49 mg/mL or about 1.50 mg/mL, including all ranges, subranges and values therebetween. In some embodiments, the polysorbate-80 is present at a concentration of about 0.90 mg/mL to about 1.1 mg/mL, about 0.95 mg/mL to about 1.1 mg/mL, about 1 mg/mL to about 1.1 mg/mL, about 0.90 mg/mL to about 1.05 mg/mL, about 0.95 mg/mL to about 1.05 mg/mL, about 1 mg/mL to about 1.05 mg/mL, about 0.90 mg/mL to about 1 mg/mL or about 0.95 mg/mL to about 1 mg/mL. In some embodiments, the polysorbate-80 is present at a concentration of about 1.0 mg/mL. In other embodiments, the polysorbate-80 is present at a concentration of about 0.4 mg/mL to about 0.6 mg/mL, about 0.45 mg/mL to about 0.6 mg/mL or about 0.5 mg/mL to about 0.6 mg/mL. In some embodiments, the polysorbate-80 is present at a concentration of about 0.5 mg/mL.

In some embodiments, the pharmaceutical composition comprises a pH of about 4 to about 8 (e.g., 4, 4.5, 5, 6, 6.5, 7, 7.5 or 8). In some embodiments, the pH is about 4, 5, 6, 7, or 8, including all ranges, subranges and values therebetween. In some embodiments, the pH is about 4 to about 8, about 5 to about 8, about 6 to about 8, about 7 to about 8, about 4 to about 7, about 5 to about 7, about 6 to about 7, about 4 to about 6, or about 5 to about 6. In some embodiments, the pH is about 6.0.

In some embodiments, the pharmaceutical composition comprises about 1 mg/mL to about 100 mg/mL of the binding molecule, about 0.5 mg/mL to about 1 mg/mL of L-histidine, about 1 mg/mL to about 2 mg/mL of L-histidine monohydrate, about 20 mg/mL to about 40 mg/mL of mannitol, about 0.5 mg/mL to 1.5 mg/mL of polysorbate-80 and wherein the pH of the pharmaceutical composition is about 4 to about 8.

In some embodiments, the pharmaceutical composition comprises about 11 mg/mL of the binding molecule, about 0.76 mg/mL of L-histidine, about 1.08 mg/mL of L-histidine monohydrate, about 32 mg/mL of mannitol, about 1.0 mg/mL of polysorbate-80 and wherein the pH of the pharmaceutical composition is about 6.0. In some embodiments, the pharmaceutical composition comprises about 31 mg/mL of the binding molecule, about 0.76 mg/mL of L-histidine, about 1.08 mg/mL of L-histidine monohydrate, about 32 mg/mL of mannitol, about 1.0 mg/mL of polysorbate-80 and wherein the pH of the pharmaceutical composition is about 6.0. In some embodiments, the pharmaceutical composition comprises about 30 mg/mL of the binding molecule, about 0.76 mg/mL of L-histidine, about 1.08 mg/mL of L-histidine monohydrate, about 32 mg/mL of mannitol, about 1.0 mg/mL of polysorbate-80 and wherein the pH of the pharmaceutical composition is about 6.0.

In some embodiments, the pharmaceutical composition comprises 11 mg/mL of the binding molecule, 0.76 mg/mL of L-histidine, 1.08 mg/mL of L-histidine monohydrate, 32 mg/mL of mannitol, 1.0 mg/mL of polysorbate-80 and wherein the pH of the pharmaceutical composition is 6.0. In some embodiments, the pharmaceutical composition comprises 31 mg/mL of the binding molecule, 0.76 mg/mL of L-histidine, 1.08 mg/mL of L-histidine monohydrate, 32 mg/mL of mannitol, 1.0 mg/mL of polysorbate-80 and wherein the pH of the pharmaceutical composition is 6.0. In some embodiments, the pharmaceutical composition comprises 30 mg/mL of the binding molecule, 0.76 mg/mL of L-histidine, 1.08 mg/mL of L-histidine monohydrate, 32 mg/mL of mannitol, 1.0 mg/mL of polysorbate-80 and wherein the pH of the pharmaceutical composition is 6.0.

In some embodiments, the pharmaceutical composition consists of 11 mg/mL of the binding molecule, 0.76 mg/mL of L-histidine, 1.08 mg/mL of L-histidine monohydrate, 32 mg/mL of mannitol, 1.0 mg/mL of polysorbate-80 and wherein the pH of the pharmaceutical composition is 6.0. In some embodiments, the pharmaceutical composition consists of 31 mg/mL of the binding molecule, 0.76 mg/mL of L-histidine, 1.08 mg/mL of L-histidine monohydrate, 32 mg/mL of mannitol, 1.0 mg/mL of polysorbate-80 and wherein the pH of the pharmaceutical composition is 6.0. In some embodiments, the pharmaceutical composition consists of 30 mg/mL of the binding molecule, 0.76 mg/mL of L-histidine, 1.08 mg/mL of L-histidine monohydrate, 32 mg/mL of mannitol, 1.0 mg/mL of polysorbate-80 and wherein the pH of the pharmaceutical composition is 6.0.

In some embodiments, the pharmaceutical composition comprises an osmolality of about 1 to about 1,000 mOsm/kg (e.g., 1, 50, 100, 150, 200, 250, 300, 350, 400, 450, 500, 550, 600, 650, 700, 750, 800, 850, 900, 950 or 1,000 mOsm/kg). In some embodiments, the osmolality is about 1 to about 1,000 mOsm/kg, about 100 to about 1,000 mOsm/kg, about 200 to about 1,000 mOsm/kg, about 300 to about 1,000 mOsm/kg, about 400 to about 1,000 mOsm/kg, about 500 to about 1,000 mOsm/kg, about 600 to about 1,000 mOsm/kg, about 700 to about 1,000 mOsm/kg, about 800 to about 1,000 mOsm/kg, about 900 to about 1,000 mOsm/kg, about 1 to about 900 mOsm/kg, about 100 to about 900 mOsm/kg, about 200 to about 900 mOsm/kg, about 300 to about 900 mOsm/kg, about 400 to about 900 mOsm/kg, about 500 to about 900 mOsm/kg, about 600 to about 900 mOsm/kg, about 700 to about 900 mOsm/kg, about 800 to about 900 mOsm/kg, about 1 to about 800 mOsm/kg, about 100 to about 800 mOsm/kg, about 200 to about 800 mOsm/kg, about 300 to about 800 mOsm/kg, about 400 to about 800 mOsm/kg, about 500 to about 800 mOsm/kg, about 600 to about 800 mOsm/kg, about 700 to about 800 mOsm/kg, about 1 to about 700 mOsm/kg, about 100 to about 700 mOsm/kg, about 200 to about 700 mOsm/kg, about 300 to about 700 mOsm/kg, about 400 to about 700 mOsm/kg, about 500 to about 700 mOsm/kg, about 600 to about 700 mOsm/kg, about 1 to about 600 mOsm/kg, about 100 to about 600 mOsm/kg, about 200 to about 600 mOsm/kg, about 300 to about 600 mOsm/kg, about 400 to about 600 mOsm/kg, about 500 to about 600 mOsm/kg, about 1 to about 500 mOsm/kg, about 100 to about 500 mOsm/kg, about 200 to about 500 mOsm/kg, about 300 to about 500 mOsm/kg, about 400 to about 500 mOsm/kg, about 1 to about 400 mOsm/kg, about 100 to about 400 mOsm/kg, about 200 to about 400 mOsm/kg, about 300 to about 400 mOsm/kg, about 1 to about 300 mOsm/kg, about 100 to about 300 mOsm/kg, about 200 to about 300 mOsm/kg, about 1 to about 200 mOsm/kg, about 100 to about 200 mOsm/kg, or about 1 to about 200 mOsm/kg. In some embodiments, the osmolality is about 180 to about 200 mOsm/kg, about 185 to about 200 mOsm/kg, about 190 to about 200 mOsm/kg, about 180 to about 195 mOsm/kg, about 185 to about 195 mOsm/kg, 190 to about 195 mOsm/kg, about 180 to about 190 mOsm/kg or about 185 to about 190 mOsm/kg. In some embodiments, the osmolality is about 190 mOsm/kg. In some embodiments, the osmolality is 190 mOsm/kg.

In some embodiments, the pharmaceutical composition comprises about 11 mg/mL of the binding agent, about 0.76 mg/mL of L-histidine, about 1.08 mg/mL of L-histidine monohydrate, about 32 mg/mL of mannitol, about 1.0 mg/mL of polysorbate-80, and wherein the pH of the pharmaceutical composition is about 6.0 and the osmolality is about 190 mOsm/kg. In some embodiments, the pharmaceutical composition comprises about 31 mg/mL of the binding agent, about 0.76 mg/mL of L-histidine, about 1.08 mg/mL of L-histidine monohydrate, about 32 mg/mL, about 1.0 mg/mL of polysorbate-80, and wherein the pH of the pharmaceutical composition is about 6.0 and the osmolality is about 190 mOsm/kg. In some embodiments, the pharmaceutical composition comprises about 30 mg/mL of the binding agent, about 0.76 mg/mL of L-histidine, about 1.08 mg/mL of L-histidine monohydrate, about 32 mg/mL, about 1.0 mg/mL of polysorbate-80, and wherein the pH of the pharmaceutical composition is about 6.0 and the osmolality is about 190 mOsm/kg.

In some embodiments, the pharmaceutical composition comprises 11 mg/mL of the binding agent, 0.76 mg/mL of L-histidine, 1.08 mg/mL of L-histidine monohydrate, 32 mg/mL, 1.0 mg/mL of polysorbate-80, and wherein the pH of the pharmaceutical composition is 6.0 and the osmolality is 190 mOsm/kg. In some embodiments, the pharmaceutical composition comprises 31 mg/mL of the binding agent, 0.76 mg/mL of L-histidine, 1.08 mg/mL of L-histidine monohydrate, 32 mg/mL, 1.0 mg/mL of polysorbate-80, and wherein the pH of the pharmaceutical composition is 6.0 and the osmolality is 190 mOsm/kg. In some embodiments, the pharmaceutical composition comprises 30 mg/mL of the binding agent, 0.76 mg/mL of L-histidine, 1.08 mg/mL of L-histidine monohydrate, 32 mg/mL, 1.0 mg/mL of polysorbate-80, and wherein the pH of the pharmaceutical composition is 6.0 and the osmolality is 190 mOsm/kg.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions provided herein can be provided as a controlled release or sustained release system. In some embodiments, a pump may be used to achieve controlled or sustained release (see, e.g., Sefton, Crit. Ref. Biomed. Eng. 14: 201-40 (1987); Buchwald et al., Surgery 88: 507-16 (1980); and Saudek et al., N. Engl. J. Med. 321: 569-74 (1989)). In some embodiments, polymeric materials can be used to achieve controlled or sustained release of a prophylactic or therapeutic agent or a composition provided herein (see, e.g., Medical Applications of Controlled Release (Langer and Wise eds., 1974); Controlled Drug Bioavailability, Drug Product Design and Performance (Smolen and Ball eds., 1984); Ranger and Peppas, J. Macromol. Sci. Rev. Macromol. Chem. 23: 61-126 (1983); Levy et al., Science 228: 190-92 (1985); During et al., Ann. Neurol. 25: 351-56 (1989); Howard et al., J. Neurosurg. 71: 105-12 (1989); U.S. Pat. Nos. 5,679,377; 5,916,597; 5,912,015; 5,989,463; and 5,128,326; PCT Publication Nos. WO 99/15154 and WO 99/20253). Examples of polymers used in sustained release formulations include, but are not limited to, poly (2-hydroxy ethyl methacrylate), poly (methyl methacrylate), poly (acrylic acid), poly (ethylene-co-vinyl acetate), poly (methacrylic acid), polyglycolides (PLG), polyanhydrides, poly (N-vinyl pyrrolidone), poly (vinyl alcohol), polyacrylamide, poly (ethylene glycol), polylactides (PLA), poly (lactide-co-glycolides) (PLGA), and polyorthoesters. In some embodiments, the polymer used in a sustained release formulation is inert, free of leachable impurities, stable on storage, sterile, and biodegradable. In some embodiments, a controlled or sustained release system can be placed in proximity of a particular target tissue, for example, the kidney, thus requiring only a fraction of the systemic dose (see, e.g., Goodson, Medical Applications of Controlled Release Vol. 2, 115-38 (1984)). Controlled release systems are discussed, for example, by Langer, Science 249: 1527-33 (1990). Any technique known to one of skill in the art can be used to produce sustained release formulations comprising one or more agents as described herein (see, e.g., U.S. Pat. No. 4,526,938, PCT publication Nos. WO 91/05548 and WO 96/20698, Ning et al., Radiotherapy & Oncology 39: 179-89 (1996); Song et al., PDA J. of Pharma. Sci. & Tech. 50: 372-97 (1995); Cleek et al., Pro. Int'l. Symp. Control. Rel. Bioact. Mater. 24: 853-54 (1997); and Lam et al., Proc. Int'l. Symp. Control Rel. Bioact. Mater. 24: 759-60 (1997)).

The active ingredients may also be entrapped in microcapsules prepared, for example, by coascervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition.

In order for the pharmaceutical compositions to be used for in vivo administration, they are preferably sterile. The pharmaceutical composition may be rendered sterile by filtration through sterile filtration membranes. The pharmaceutical compositions provided herein generally can be placed into a container having a sterile access port, for example, an intravenous solution bag or vial having a stopper pierceable by a hypodermic injection needle.

In some embodiments, the pharmaceutical compositions disclosed herein are for use in treating a cancer in a subject. In some embodiments, the pharmaceutical compositions disclosed herein are for use in the prevention of cancer in a subject. In some embodiments, the subject is a mammal. In some embodiments, the subject is human. The details related to treatment and prevention are disclosed in the "Therapeutic Methods and Applications" section below.

Therapeutic Methods and Applications

Provided herein are methods of treating a disease or disorder in a subject, comprising administering to the subject a therapeutically effective amount of the binding molecule, or pharmaceutical compositions thereof disclosed herein. Also provided herein are methods of preventing a disease or disorder in a subject, comprising administering to the subject a therapeutically effective amount of the binding molecule, or pharmaceutical compositions thereof disclosed herein.

In some embodiments, the method described herein may be used in the treatment of a cell-proliferative disorder, such as cancer. In some embodiments, the method described herein may be used in the prevention of a cell-proliferative disorder, such as cancer. In some embodiments, the cancer is blood cancer. In some embodiments, the cancer is solid tumor. For example, cancers that may be treated using the compositions and methods disclosed herein include, but are not limited to, leukemia, lymphoma, myeloma, carcinoma, sarcoma, or brain and spinal cord cancer. In some embodiments, the cancer is chronic lymphocytic leukemia (CLL), B cell acute lymphocytic leukemia (B-ALL), acute lymphoblastic leukemia (ALL), acute myeloid leukemia (AML), non-Hodgkin's lymphoma (NHL), diffuse large cell lymphoma (DLCL), diffuse large B cell lymphoma (DLBCL), Hodgkin's lymphoma, multiple myeloma, renal cell carcinoma (RCC), hepatocellular carcinoma, melanoma, mesothelioma, colorectal cancer, bladder cancer, breast cancer, colorectal cancer, ovarian cancer, prostate cancer, lung cancer, esophageal cancer, pancreatic cancer, head and neck cancer, liver cancer, cervical cancer, breast cancer, astrocytoma, medulloblastoma, and neuroblastoma. In some embodiments, the cancer is insensitive or resistant.

In some embodiments, the subject may be a neonate, a juvenile, or an adult. In some embodiments, the subject is human. In some embodiments, the subject is non-human primates (e.g., monkeys, baboons, and chimpanzees), mice, rats, bovines, horses, household cats, tigers and other large cats, dogs, pigs, rabbits, goats, deer, sheep, ferrets, gerbils, guinea pigs, hamsters, bats, and birds (e.g., chickens, turkeys, and ducks).

In some embodiments, treating refers to the treatment of a disease in a mammal, e.g., in a human, including (a) inhibiting the disease, i.e., arresting disease development or preventing disease progression; (b) relieving the disease, i.e., causing regression of the disease state or relieving one or more symptoms of the disease; and (c) curing the disease, i.e., remission of one or more disease symptoms. In some embodiments, treatment results in an improvement or remediation of the symptoms of the disease. In some embodiments, treatment may refer to a short-term (e.g., temporary and/or acute) and/or a long-term (e.g., sustained) improvement or remediation in one or more disease symptoms. In some embodiments, the improvement is an observable or measurable improvement. In some embodiments, the improvement is an improvement in the general feeling of well-being of the subject. In some embodiments, administration of the pharmaceutical compositions disclosed herein may reduce one or more symptoms of cancer, including but not limited to, death, fatigue, area of thickening under the skin, abnormal bump, weight changes, skin changes, fever and night sweats.

Administration of the binding molecule, or pharmaceutical compositions thereof can occur by infusion (e.g., continuous or bolus), injection, irrigation, inhalation, consumption, electro-osmosis, hemodialysis, iontophoresis, and other methods known in the art.

In some embodiments, administration route is intraarterial, intracranial, intradermal, intraduodenal, intrammamary, intrameningeal, intraperitoneal, intrathecal, intratumoral, intravenous, intravitreal, ophthalmic, parenteral, spinal, subcutaneous, ureteral, urethral, vaginal, or intrauterine. In some embodiments, administration route is local or systemic.

The effective amount of the binding molecule, or pharmaceutical compositions thereof administered to a particular subject will depend on a variety of factors, several of which will differ from patient to patient including the disorder being treated and the severity of the disorder; activity of the specific agent(s) employed; the age, body weight, general health, sex and diet of the patient; the timing of administration, route of administration; the duration of the treatment; drugs used in combination; the judgment of the prescribing physician; and like factors known in the medical arts. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

Dosage amounts of the binding molecule, or pharmaceutical compositions disclosed herein can typically be in the range of from about 0.0001 mg/kg/day to about 1000 mg/kg/day, but can be higher or lower, depending upon, among other factors, the activity of the compound, its bioavailability, and various factors discussed above. In some embodiments, the dose is from about 0.0001 mg/kg to about 1000 mg/kg of body weight per day. In some embodiments, the dose is from about 0.001 mg/kg to about 1000 mg/kg of body weight per day. In some embodiments, the dose is from about 0.01 mg/kg to about 1000 mg/kg of body weight per day. In some embodiments, the dose is from about 0.1 mg/kg to about 100 mg/kg of body weight per day. In some embodiments, the dose is from about 0.5 mg/kg to about 50 mg/kg of body weight per day. In some embodiments, the dose is from about 1 mg/kg to about 25 mg/kg of body weight per day. In some embodiments, the dose is from about 5 mg/kg to about 15 mg/kg of body weight per day. In some embodiments, the dose is about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg.

The number of administrations of treatment to a subject may vary. In some embodiments, introducing the binding molecules, or pharmaceutical compositions thereof into the subject may be a one-time event. In some embodiments, such treatment may require an on-going series of repeated treatments (e.g., once per day, once per week, or multiple times per day or week). In some embodiments, multiple administrations of the pharmaceutical compositions may be required before an effect is observed. The exact protocols depend upon the disease or condition, the stage of the disease and parameters of the individual subject being treated.

In some embodiments, the binding molecules, or pharmaceutical compositions thereof disclosed herein are administered in combination with one or more additional therapeutic composition(s).

In some embodiments, the binding molecule, or pharmaceutical compositions disclosed herein are administered in combination with additional therapeutic composition(s). In some embodiments, the binding molecule, or pharmaceutical compositions disclosed herein and the additional therapeutic composition(s) are administered simultaneously. In some embodiments, the binding molecule, or pharmaceutical compositions disclosed herein is administered before the additional therapeutic composition(s). In some embodiments, the pharmaceutical compositions disclosed herein is administered after the additional therapeutic composition(s).

In some embodiments, administration of the binding molecule, or pharmaceutical compositions disclosed herein in combination with the additional therapeutic composition (s) results in an enhanced therapeutic effect in a cancer than is observed by treatment with either the pharmaceutical compositions disclosed herein or the additional therapeutic composition alone. In some embodiments, the cancer is resistant, refractory, or insensitive to treatment by the additional therapeutic composition alone. In some embodiments, the cancer is partially resistant, partially refractory, or partially insensitive to treatment by the additional therapeutic composition alone.

In some embodiments, the second therapeutic composition is an immune checkpoint inhibitor. Several immune checkpoint inhibitors are known in the art and have received FDA approval for the treatment of one or more cancers. For example, FDA-approved PD-L1 inhibitors include Atezolizumab (Tecentriq®, Genentech), Avelumab (Bavencio®, Pfizer), and Durvalumab (Imfinzi®, AstraZeneca); FDA-approved PD-1 inhibitors include Pembrolizumab (Keytruda®, Merck) and Nivolumab (Opdivo®, Bristol-Myers Squibb); and FDA-approved CTLA-4 inhibitors include Ipilimumab (Yervoy®, Bristol-Myers Squibb). Additional inhibitory immune checkpoint molecules that may be the target of future therapeutics include A2AR, B7-H3, B7-H4, BTLA, IDO, LAG3 (e.g., BMS-986016, under development by BSM), KIR (e.g., Lirilumab, under development by BSM), TIM3, TIGIT, and VISTA.

In some embodiments, the second therapeutic composition is CAR expressing immune effector cells. Non-limiting examples of such CARS include CD171-specific CARs (Park et al., Mol Ther (2007) 15(4):825-833), EGFRvIII-specific CARs (Morgan et al., Hum Gene Ther (2012) 23(10):1043-1053), EGF-R-specific CARs (Kobold et al., J Natl Cancer Inst (2014) 107(1):364), carbonic anhydrase K-specific CARs (Lamers et al., Biochem Soc Trans (2016) 44(3):951-959), FR-α-specific CARs (Kershaw et al., Clin Cancer Res (2006) 12(20):6106-6015), HER2-specific CARs (Ahmed et al., J Clin Oncol (2015) 33(15)1688-1696; Nakazawa et al., Mol Ther (2011) 19(12):2133-2143; Ahmed et al., Mol Ther (2009) 17(10):1779-1787; Luo et al., Cell Res (2016) 26(7):850-853; Morgan et al., Mol Ther (2010) 18(4):843-851; Grada et al., Mol Ther Nucleic Acids (2013) 9(2):32), CEA-specific CARs (Katz et al., Clin Cancer Res (2015) 21(14):3149-3159), IL13Rα2-specific CARs (Brown et al., Clin Cancer Res (2015) 21(18):4062-4072), GD2-specific CARs (Louis et al., Blood (2011) 118(23):6050-6056; Caruana et al., Nat Med (2015) 21(5): 524-529), ErbB2-specific CARs (Wilkie et al., J Clin Immunol (2012) 32(5):1059-1070), VEGF-R-specific CARs (Chinnasamy et al., Cancer Res (2016) 22(2):436-447), FAP-specific CARs (Wang et al., Cancer Immunol Res (2014) 2(2):154-166), MSLN-specific CARs (Moon et al, Clin Cancer Res (2011) 17(14):4719-30), NKG2D-specific CARs (VanSeggelen et al., Mol Ther (2015) 23(10):1600-1610), CD19-specific CARs (Axicabtagene ciloleucel (Yescarta®) and Tisagenlecleucel (Kymriah®). See also, Li et al., J Hematol and Oncol (2018) 11(22), reviewing clinical trials of tumor-specific CARs.

Exemplary Embodiments

Embodiment 1: A binding molecule that binds to programmed cell death protein 1 (PD-1), wherein the binding molecule comprises:

a. a variable heavy chain CDR1 (HCDR1) comprising an amino acid sequence of SEQ ID No: 1 or a HCDR1 having one to two amino acid substitutions as compared to the sequence of SEQ ID No: 1;
b. a variable heavy chain CDR2 (HCDR2) comprising an amino acid sequence of SEQ ID No: 2 or a HCDR2 having one to two amino acid substitutions as compared to the sequence of SEQ ID No: 2; and
c. a variable heavy chain CDR3 (HCDR3) comprising an amino acid sequence of SEQ ID No: 3 or a HCDR3 having one to two amino acid substitutions as compared to the sequence of SEQ ID No: 3, wherein the binding molecule is numbered with reference to the Kabat numbering system.

Embodiment 1: The binding molecule of embodiment 1, wherein the binding molecule comprises:

a. a variable light chain CDR1 (LCDR1) comprising an amino acid sequence of SEQ ID No: 4 or a LCDR1 having one to two amino acid substitutions as compared to the sequence of SEQ ID No: 4;
b. a variable light chain CDR2 (LCDR2) comprising an amino acid sequence of SEQ ID No: 5 or a LCDR2 having one to two amino acid substitutions as compared to the sequence of SEQ ID No: 5; and
c. a variable light chain CDR3 (LCDR3) comprising an amino acid sequence of SEQ ID No: 6 or a LCDR3 having one to two amino acid substitutions as compared to the sequence of SEQ ID No: 6, wherein the binding molecule is numbered with reference to the Kabat numbering system.

Embodiment 3: The binding molecule of embodiment 1 or embodiment 2, wherein the binding molecule comprises:

a. a variable heavy chain CDR1 (HCDR1) comprising an amino acid sequence of SEQ ID No: 1 or a HCDR1 having one to two amino acid substitutions as compared to the sequence of SEQ ID No: 1;
b. a variable heavy chain CDR2 (HCDR2) comprising an amino acid sequence of SEQ ID No: 2 or a HCDR2 having one to two amino acid substitutions as compared to the sequence of SEQ ID No: 2;
c. a variable heavy chain CDR3 (HCDR3) comprising an amino acid sequence of SEQ ID No: 3 or a HCDR3 having one to two amino acid substitutions as compared to the sequence of SEQ ID No: 3;
d. a variable light chain CDR1 (LCDR1) comprising an amino acid sequence of SEQ ID No: 4 or a LCDR1 having one to two amino acid substitutions as compared to the sequence of SEQ ID No: 4;
e. a variable light chain CDR2 (LCDR2) comprising an amino acid sequence of SEQ ID No: 5 or a LCDR2 having one to two amino acid substitutions as compared to the sequence of SEQ ID No: 5; and a variable light chain CDR3 (LCDR3) comprising an amino acid sequence of SEQ ID No: 6 or a LCDR3 having one to two amino acid substitutions as compared to the sequence of SEQ ID No: 6.

Embodiment 4: The binding molecule of any one of embodiments 1 to 3, wherein the binding molecule comprises:

a. a variable heavy chain CDR1 (HCDR1) comprising an amino acid sequence of SEQ ID No: 1;
b. a variable heavy chain CDR2 (HCDR2) comprising an amino acid sequence of SEQ ID No: 2;
c. a variable heavy chain CDR3 (HCDR3) comprising an amino acid sequence of SEQ ID No: 3;
d. a variable light chain CDR1 (LCDR1) comprising an amino acid sequence of SEQ ID No: 4;
e. a variable light chain CDR2 (LCDR2) comprising an amino acid sequence of SEQ ID No: 5; and
f. a variable light chain CDR3 (LCDR3) comprising an amino acid sequence of SEQ ID No: 6.

Embodiment 5: The binding molecule of any one of embodiments 1 to 4, wherein the binding molecule binds amino acid residues of 80-115 (SEQ ID NO: 29) of the human PD-1 when numbered in accordance with SEQ ID NO: 25.

Embodiment 6: The binding molecule of any one of embodiments 1 to 5, wherein the HCDR1, HCDR2, and HCDR3 of the binding molecule binds residues 80-104 (SEQ ID NO: 26).

Embodiment 7: The binding molecule of any one of embodiments 1 to 5, wherein the HCDR2, LCDR1, and LCDR2, of the binding molecule binds residues 105-115 (SEQ ID NO: 27).

Embodiment 8: A binding molecule, wherein the binding molecule binds to an epitope of human PD-1 having amino acid residues of 80-115 (SEQ ID NO: 29) when numbered in accordance with SEQ ID NO: 25.

Embodiment 9: The binding molecule of any one of embodiments 1 to 8, wherein the amino acid residues of 105-115 (SEQ ID NO: 27) of the human PD-1 do not overlap with the residues involved in hPD-1:hPD-L1 interaction.

Embodiment 10: The binding molecule of any one of embodiments 1 to 8, wherein the binding molecule sterically blocks interaction between hPD-1 and hPD-L1.

Embodiment 11: The binding molecule of any one of embodiments 1 to 10, wherein the binding molecule comprises a heavy chain variable domain (VH) comprising an amino acid sequence that is at least 85% identical to SEQ ID No: 19, and a light chain variable domain (VL) comprising an amino acid sequence that is at least 85% identical to SEQ ID No: 20.

Embodiment 12: The binding molecule of any one of embodiments 1 to 11, wherein the binding molecule comprises a VH comprising an amino acid sequence of SEQ ID No: 19, and a VL comprising an amino acid sequence of SEQ ID No: 20.

Embodiment 13: The binding molecule of any one of embodiments 1 to 12, wherein the binding molecule is a monoclonal antibody or antigen-binding fragment thereof.

Embodiment 14: The binding molecule of any one of embodiments 1 to 13, wherein the binding molecule is a fully human monoclonal antibody or antigen-binding fragment.

Embodiment 15: The binding molecule of embodiment 13 or 14, wherein the monoclonal antibody or antigen-binding fragment thereof comprises an IgG isotype selected from the group consisting of IgG1, IgG2, IgG3, IgG4, and a variant thereof.

Embodiment 16: The binding molecule of embodiment 15, wherein the binding molecule is a fully human monoclonal antibody comprising an IgG4-PE.

Embodiment 17: The binding molecule of embodiment 16, wherein the binding molecule comprises a heavy chain comprising an amino acid sequence that is at least about 85% identical to SEQ ID No: 21, and a light chain comprising an amino acid sequence that is at least about 85% identical to SEQ ID No: 22.

Embodiment 18: The binding molecule of embodiment 17, wherein the binding molecule comprises a heavy chain comprising an amino acid sequence of SEQ ID No: 21, and a light chain comprising an amino acid sequence of SEQ ID No: 22.

Embodiment 19: The binding molecule of embodiment 15, wherein the binding molecule is a fully human monoclonal antibody comprising an IgG1-LALA.

Embodiment 20: The binding molecule of embodiment 19, wherein the binding molecule comprises a heavy chain comprising an amino acid sequence that is at least about 85% identical to SEQ ID No: 23, and a light chain comprising an amino acid sequence that is at least about 85% identical to SEQ ID No: 24.

Embodiment 21: The binding molecule of embodiment 20, wherein the binding molecule comprises a heavy chain comprising an amino acid sequence of SEQ ID No: 23, and a light chain comprising an amino acid sequence of SEQ ID No: 24.

Embodiment 22: The binding molecule of any one of embodiments 6 to 21, wherein the binding molecule blocks the interaction between PD-1 and programmed cell death ligand 1 (PD-L1).

Embodiment 23: A polynucleotide encoding the binding molecule of any one of embodiments 1 to 22.

Embodiment 24: A vector, comprising the polynucleotide of embodiment 23.

Embodiment 25: A pharmaceutical composition comprising the binding molecule of any one of embodiments 1 to 22, the polynucleotide of embodiment 23, or the vector of embodiment 24.

Embodiment 26: The pharmaceutical composition of embodiment 25, wherein the pharmaceutical composition further comprises a pharmaceutically acceptable carrier.

Embodiment 27: The pharmaceutical composition of embodiment 25 or 26, wherein the pH of the pharmaceutical composition is about 4.0 to about 8.0.

Embodiment 28: The pharmaceutical composition of embodiment 27, wherein the pH of the pharmaceutical composition is about 6.0.

Embodiment 29: The pharmaceutical composition of any one of embodiments 25 to 28, wherein the binding molecule is present at a concentration of about 1 mg/mL to about 100 mg/mL.

Embodiment 30: The pharmaceutical composition of embodiment 29, wherein the binding molecule is present at a concentration of about 31 mg/mL.

Embodiment 31: The pharmaceutical composition of embodiment 29, wherein the binding molecule is present at a concentration of about 25 mg/mL.

Embodiment 32: The pharmaceutical composition of any one of embodiments 25 to 31, wherein L-histidine is present at a concentration of about 0.5 mg/mL to about 1 mg/mL.

Embodiment 33: The pharmaceutical composition of embodiment 32, wherein L-histidine is present at a concentration of about 0.76 mg/mL.

Embodiment 34: The pharmaceutical composition of any one of embodiments 26 to 33, wherein L-histidine monohydrate is present at a concentration of about 1 mg/mL to about 2 mg/mL.

Embodiment 35: The pharmaceutical composition of embodiment 34, wherein L-histidine monohydrate is present at a concentration of about 1.08 mg/mL.

Embodiment 36: The pharmaceutical composition of any one of embodiments 26 to 35, wherein mannitol is present at a concentration of about 20 mg/mL to about 40 mg/mL.

Embodiment 37: The pharmaceutical composition of embodiment 36, wherein the mannitol is present at a concentration of about 32 mg/mL.

Embodiment 38: The pharmaceutical composition of any one of embodiments 26 to 35, wherein sucrose is present at a concentration of about 75 mg/mL to about 85 mg/mL.

Embodiment 39: The pharmaceutical composition of embodiment 38, wherein the sucrose is present at a concentration of about 80 mg/mL.

Embodiment 40: The pharmaceutical composition of any one of embodiments 26 to 39, wherein polysorbate-80 is present at a concentration of about 0.5 mg/mL to about 1.5 mg/mL.

Embodiment 41: The pharmaceutical composition of any one of embodiments 36 to 37, wherein polysorbate-80 is present at a concentration of about 1.0 mg/mL.

Embodiment 42: The pharmaceutical composition of any one of embodiments 38 to 39, wherein polysorbate-80 is present at a concentration of about 1.0 mg/mL.

Embodiment 43: The pharmaceutical composition of embodiment 26, wherein the pharmaceutical composition comprises about 31 mg/mL of the binding molecule, about 0.76 mg/mL of L-histidine, about 1.08 mg/mL of L-histidine monohydrate, about 32 mg/mL of mannitol, about 1.0 mg/mL of polysorbate-80, and wherein the pH of the pharmaceutical composition is about 6.0.

Embodiment 44: The pharmaceutical composition of embodiment 26, wherein the pharmaceutical composition comprises about 25 mg/mL of the binding molecule, about 0.76 mg/mL of L-histidine, about 1.08 mg/mL of L-histidine monohydrate, about 80 mg/ml sucrose, about 0.5 mg/mL of polysorbate-80, and wherein the pH of the pharmaceutical composition is about 6.0.

Embodiment 45: A method of treating a cancer in a subject in need thereof, comprising administering to the subject a therapeutically effective amount of the pharmaceutical composition of any one of embodiments 26 to 44.

Embodiment 46: A method of preventing a cancer in a subject in need thereof, comprising administering to the subject a therapeutically effective amount of the pharmaceutical composition of any one of embodiments 26 to 44.

Embodiment 47: The method of embodiment 45 or 46, wherein the administering of the binding molecule activates the immune system of the subject.

Embodiment 48: The method of any one of embodiments 45 to 47, wherein the therapeutically effective amount of the pharmaceutical composition is administered with a therapeutically effective amount of one or more additional therapeutic agent.

Embodiment 49: The method of embodiment 48 wherein the one or more additional agent comprises an anti-PD1 antibody.

Embodiment 50: The method of any one of embodiments 45 to 49, wherein the cancer is a solid tumor.

Embodiment 51: The method of any one of embodiments 45 to 49, wherein the cancer is a blood cancer.

Embodiment 52: The method of any one of embodiments 50 to 51, wherein the cancer is resistant, refractory, and/or insensitive to at least one prior therapeutic agent to treat the cancer.

Embodiment 53: The method of embodiment 52 wherein the at least one prior therapeutic agent comprises an anti-PD1 antibody.

Embodiment 54: Use of the pharmaceutical composition of any one of embodiments 26 to 44 to treat cancer in a subject in need thereof.

Embodiment 55: The use of embodiment 54, wherein the cancer is a solid tumor.

Embodiment 56: The use of embodiment 55, wherein the cancer is a blood cancer.

Embodiment 57: Means for treating a cancer in a subject in need thereof, the improvement comprising administering to the subject in need thereof an effective amount of the binding molecule of any one of embodiments 1 to 22, or the pharmaceutical composition of any one of embodiments 25 to 44.

Embodiment 58: The means of embodiment 57, wherein the wherein the cancer is resistant, refractory, and/or insensitive to at least one prior anti-PD1 antibody to treat the cancer.

Embodiment 59: A binding molecule wherein the binding molecule binds to human PD-1, comprising amino acids residues 80-115 when numbered in accordance with SEQ ID NO: 25, and wherein the binding molecule blocks the interaction between hPD-1 and hPD-L1.

Embodiment 60: A pharmaceutical composition comprising the binding molecule of embodiment 59 and a carrier.

Embodiment 61: The binding molecule of embodiment 59 for use in a method of treating a cancer in a subject in need thereof.

EXAMPLES

The following is a description of various methods and materials used in the studies. They are put forth so as to provide those of ordinary skill in the art with a complete disclosure and description of how to make and use the present disclosure, and are not intended to limit the scope of what the inventors regard as their invention, nor are they intended to represent that the experiments below were performed and are all of the experiments that may be performed. It is to be understood that exemplary descriptions written in the present tense were not necessarily performed, but rather that the descriptions can be performed to generate the data and the like associated with the teachings of the present invention. Efforts have been made to ensure accuracy with respect to numbers used (e.g., amounts, percentages, etc.), but some experimental errors and deviations should be accounted for.

Example 1—Selection of Human Variable Regions Specific for PD-1

Specific antibodies for human PD-1 (hPD-1) were obtained through phage display using synthetic libraries of human variable regions in a single-chain variable fragment (scFv) format. The synthetic libraries were constructed with the IGHV3-23*01 and IGKV1-39*01 gene segments, which are widely used in natural and therapeutic antibodies. The selection process is summarized in FIG. 1. After three rounds of selection in solution with decreasing concentrations (100, 10, and 1 nM) of recombinant biotinylated hPD-1 protein, 315 clones were tested for identification of anti-PD-1 specific and unique sequences, resulting in 215 positive and 60 unique scFvs. Out of these unique scFvs, the top six scFvs were selected for conversion to human hIgG4-PE.

Example 2—Conversion to hIgG4PE, hIgG1-LALA and hIgG1

Figure 2A:
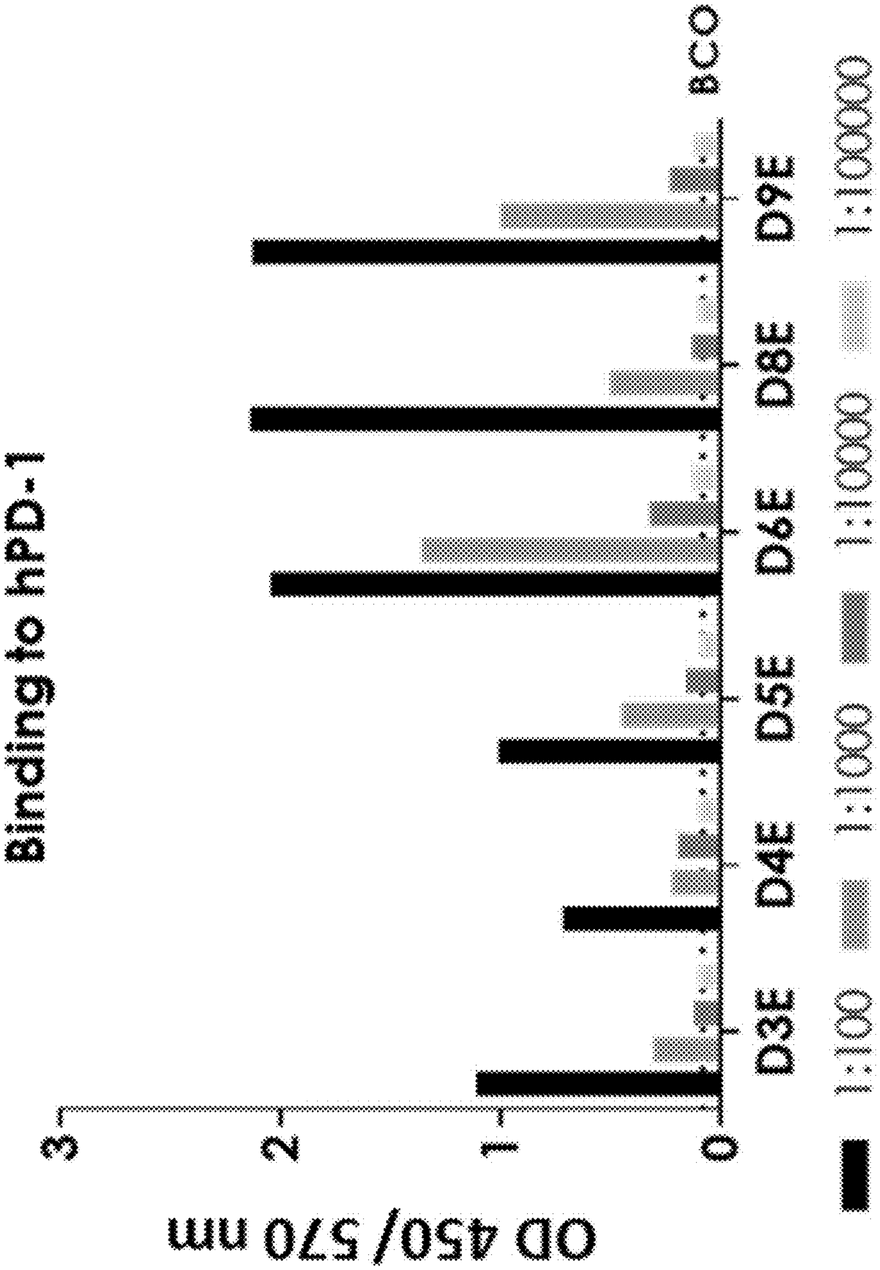
FIGS. 2A and 2B show differences in binding and expression of anti-PD1 antibodies to human PD1 (hPD-1).
Figure 2B:
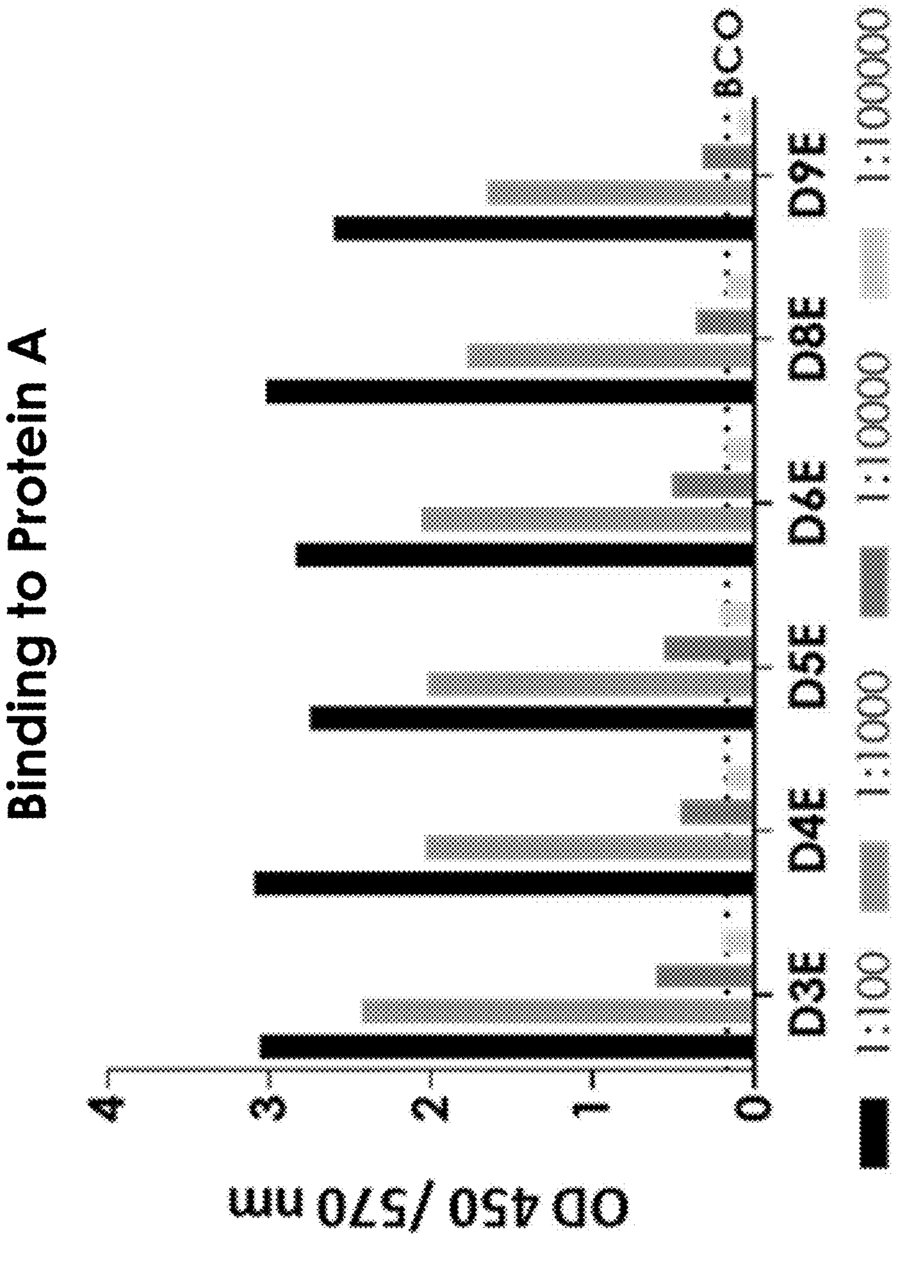

The variable heavy chain regions (VH) of the top six clones were amplified by PCR and cloned into expression vectors containing the constant heavy chain regions of a human IgG4-PE. The mutations "PE" in hIgG4 are used to stabilize this isotype and eliminate residual effector functions, with "P" being Proline to Serine at position 228 and "E" Glutamic Acid to Leucine at position 235 (Kabat numbering). The mutation "P" stabilizes the IgG4 hinge region that naturally tends to form combinations with other IgG4s, whereas "E" eliminates any residual effector activity of antibodies by abolishing binding with Fcγ receptors. The variable light chain regions (VL) were cloned into a vector containing the constant domain of the human kappa chain. Transfection-grade plasmids were generated and co-transfected into Expi293F cells by lipotransfection. The transfection supernatants were evaluated for hPD-1 binding and Protein A binding after the fourth day of incubation of the transfected cells (FIGS. 2A and 2B). See Table 19 below.

TABLE 19

Binding and blocking of six best scFv converted to hIgG4PE. As a negative control the antibody 3C5, an anti-VEGFR3 antibody, with an hIgG4PE isotype, expressed and Protein-A purified side-by-side with the anti-PD-1 antibodies, was used.

| Antibody name | Binding to hPD-1 $EC_{50}$ (μg/mL) | Blocking hPD-1:hPD-L1 $IC_{50}$ (μg/mL) |
|---|---|---|
| D3E | 0.043 | 0.852 |
| D4E | 0.082 | 0.535 |
| D5E | 0.06 | 0.406 |
| D6E | 0.011 | 0.095 |
| D8E | 0.056 | 1.839 |
| D9E | 0.066 | 0.541 |
| 3C5 | — | — |

Notably, although all antibodies are similarly expressed (FIGS. 2A and 2B), D6E had a superior binding to hPD-1 than the other antibodies.

Based on these results, D6E, hereinafter referred to as UDIZ-008, was selected for further characterization.

The variable regions of UDIZ-008 are encoded by human germline genes IGHV3-23*01 and IGKV1-39*01 (FIG. 3), which are widely used in natural and therapeutic antibodies. The HCDR3 has a length of 10 amino acids, typical of human antibodies.

Furthermore, UDIZ-008 was converted into two additional therapeutic formats: hIgG1-LALA (referred herein as UDIZ-007) and hIgG1 (herein referred as D63E). hIgG1-LALA has been described as an alternative therapeutic isotype to hIgG4, with the advantage of being more stable and producing higher yields than hIgG4, thus facilitating the pharmaceutical development. The "LALA" mutations (L234A/L235A) reduce binding to FcγRI, FcγRII, and FcγRIII receptors as well as to complement C1q, achieving a similar effect to hIgG4, leading to attenuated effector functions and hence, avoiding depletion of the T-cells. UDIZ-007 and UDIZ-008 antibodies have the same variable (V) regions but were engineered with two distinct isotypes, hIgG1-LALA and hIgG4-PE, respectively (see Table 4). D63E has the same as antibody sequence of UDIZ-007 but no "LALA" mutations, and was used as a control.

The isotype, Fc mutations and allotype, as well as the theoretical MW and pI of UDIZ-007, UDIZ-008, D63E, calculated from the amino acid sequence, are summarized in Table 4.

TABLE 4

Theoretical parameters of UDIZ-008, UDIZ-007, and D63E

| ID | Human Isotype | Fc Mutations | Allotype | MW (Da) | pI |
|---|---|---|---|---|---|
| UDIZ-007 | IgG1 | L234A L235A | G1m17,1 | 144,369.97 | 8.24 |
| UDIZ-008 | IgG4 | S228P L235E | nG4m(a) | 143,834.91 | 6.58 |
| D63E | IgG1 | — | G1m17,1 | 144,201.65 | 8.24 |

Example 3—Antibody Expression in Chinese Hamster Ovary (CHO) Cells

To further characterize UDIZ-007 and UDIZ-008, as well as the isotype controls, generated with the V regions of the anti-lysozyme antibody (D1.3) converted to hIgG1-LALA (herein referred as D92) and hIgG4-PE (herein referred as D55), were expressed at GenScript using CHO cells, which is the platform that eventually will be used to manufacture the clinical material. CHO expression products were purified using Protein A (MabSelect PrismA™) and kept in PBS buffer, pH 7.2. Initial characterization of these four antibodies is shown in Table 5.

TABLE 5

Quality attributes obtained by GenScript

| Antibody | Total mass (mg) | Concentration (A280 nm) [mg/mL] | Purity (% monomer) | Endotoxin Content (E.U./mg) |
|---|---|---|---|---|
| UDIZ-007 | 126.14 | 4.38 | ≥95% (SDS-PAGE under N.R. conditions) 94% (SEC-HPLC) | ≤0.1 |
| UDIZ-008 | 111.10 | 4.48 | ≥90% (SDS-PAGE in N.R. conditions) 89% (SEC-HPLC) | ≤0.2 |
| D92C (IgG1-LALA) | 548.73 | 12.06 | ≥95% (SDS-PAGE in N.R. conditions) 97% (SEC-HPLC) | ≤0.1 |
| D55C (IgG4-PE) | 1,396.34 | 11.54 | ≥95% (SDS-PAGE in N.R. conditions) 95% (SEC-HPLC) | ≤0.1 |

NR: Non-reducing.

Figure 4A:
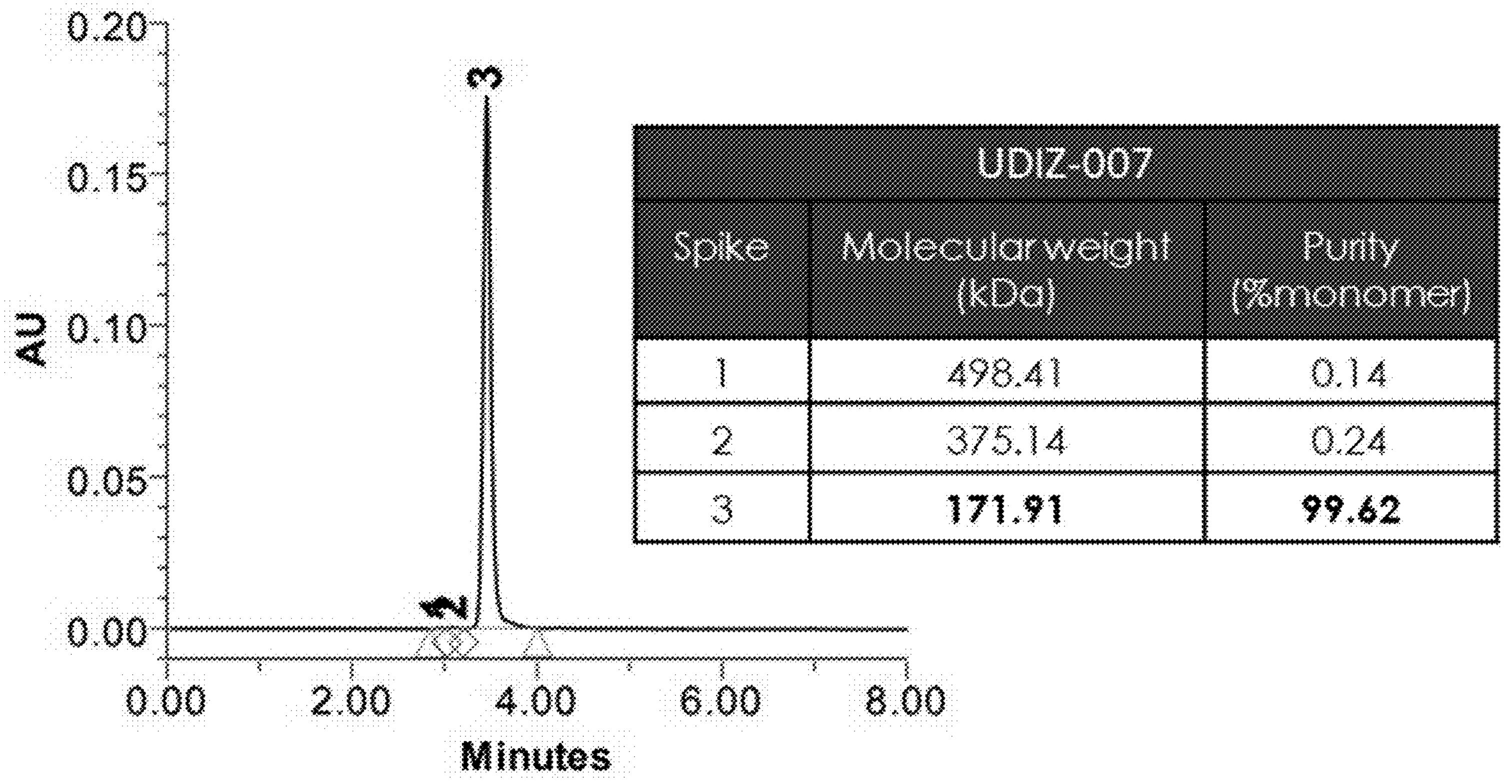
FIGS. 4A and 4B show the monomeric content of UDIZ-007 (FIG. 4A) and UDIZ-008 (FIG. 4B).
Figure 4B:
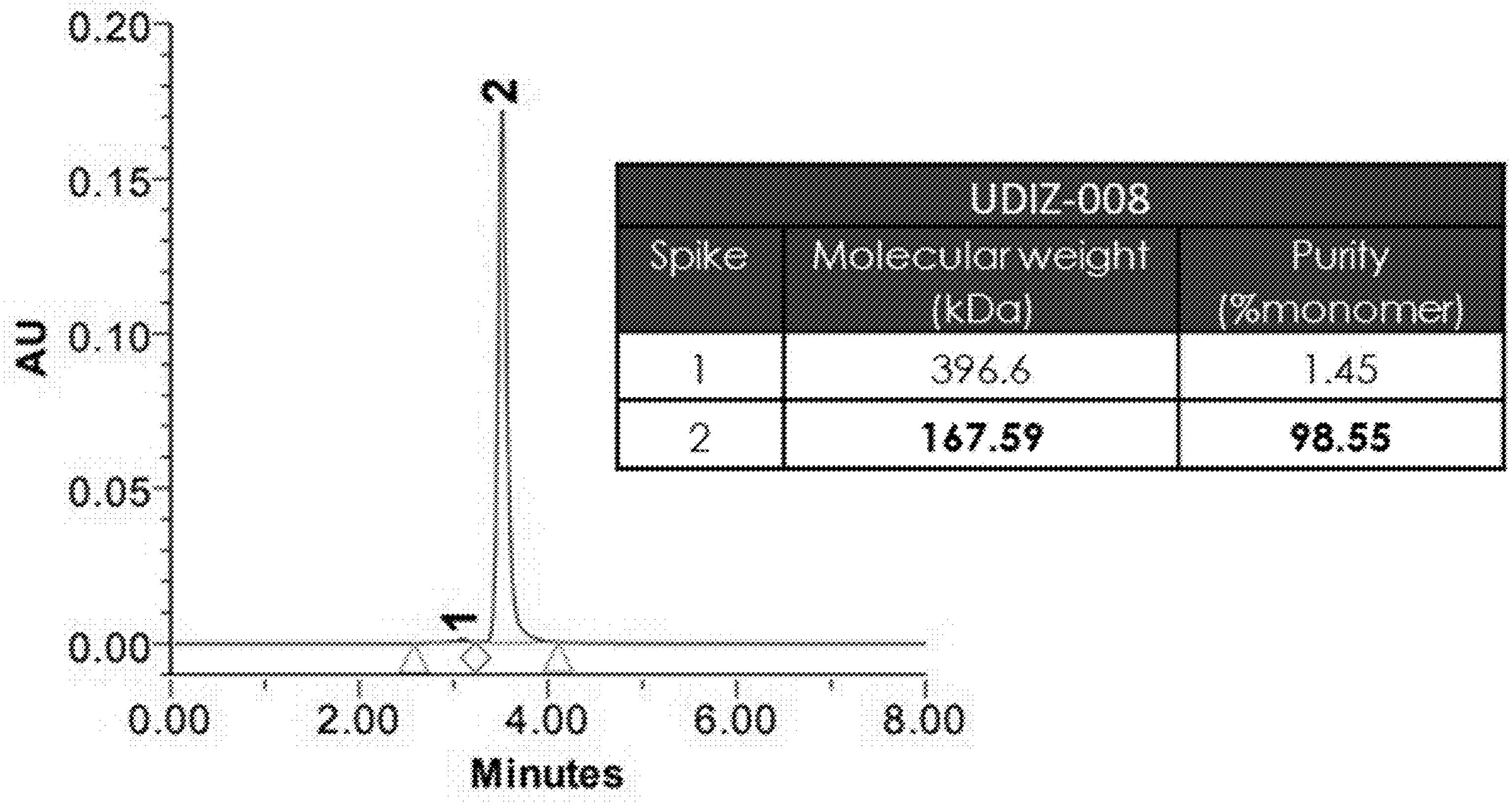

Since the monomeric content of UDIZ-007 (94%) and UDIZ-008 (89%) was below 95%, the GenScript initial material was polished using a Superose™ 6 increase 10/300 GL Cat. 29-0915-96 column. The column was previously sanitized with 0.2 M NaOH for 30 min and equilibrated with 1 column volume (CV) employing 1×PBS at pH 7.4 as mobile phase. Injections of 500 μL of each of the antibodies were made at a flow rate of 0.5 mL/min. The fractions corresponding to the monomer were collected and concentrated in Amicon Ultra-15 diafiltration tubes Cat. UFC905096. The monomer content of UDIZ-007 and UDIZ-008 reached 99.62% and 98.55%, respectively (FIGS. 4A and 4B).

Example 4—Physiochemical Characterization of UDIZ-007 and UDIZ-008

The following assays were performed to assess the physicochemical profiles of UDIZ-007 and UDIZ-008:

1. Antibody sterility test,
2. Determination of bacterial endotoxin content,
3. Molecular identity in polyacrylamide gels with SDS (SDS-PAGE),
4. Determination of intact mass by Mass Spectrometry (M.S.),
5. Thermal stability by Protein Thermal Shift™
6. Determination of the dissociation constant (KD) for hPD-1 by Surface Plasmon Resonance (SPR), and
7. Determination of the dissociation constant (KD) for Cynomolgus monkey PD-1 (cyno; cPD-1) by SPR.

Antibody Sterility Test

After polishing UDIZ-007 and UDIZ-008, both antibodies were sterilized by filtration (0.22 μm pore size filters). To corroborate their sterility, an aliquot of each antibody was inoculated in rich medium (trypticasein soy broth) and incubated for 48 h at 37° C. and 5% CO2. Bacterial growth was not observed in any of the antibodies, therefore both samples were considered sterile.

Determination of Bacterial Endotoxin Content

The endotoxin content of UDIZ-007 and UDIZ-008 was determined by the Limulus Amebocyte Lysate method. Samples of interest were mixed in dilutions with an endotoxin standard and deposited in a 96-well flat-bottom plate. They were then incubated at 37° C. for 1 h to observe possible gel formation and interpolated onto a standard endotoxin curve. For products used in preclinical research, an endotoxin content of <3 E.U./mL was suggested. Batches obtained from UDIZ-007 and UDIZ-008 showed a 2 U.E./mL and 0.25 UE/mL, respectively, indicating that they could be used in in vitro and in vivo assays.

Molecular Identity in SDS-Polyacrylamide Gels (SDS-PAGE)

The electrophoretic profiles of UDIZ-007 and UDIZ-008 were determined under non-reducing and reducing conditions using b-mercaptoethanol (Table 6). In non-reducing conditions, bands of 129.3-134.5 kDa corresponding to IgG were observed. Under reducing conditions, two bands were observed, one of 47.6-49.4 kDa corresponding to the heavy chains and the other of 24.4-25.9 kDa corresponding to the light chains, also consistent with the typical pattern of an IgG. In both cases, no contaminating proteins were observed.

TABLE 6

Molecular identity in non-reducing and reducing conditions

| Antibodies | Non-reducing Conditions | Reducing Conditions |
|---|---|---|
| UDIZ-007 | 134.5 kDa | 47.6 kDa (heavy chain) 24.4 kDa (light chain) |
| UDIZ-008 | 129.3 kDa | 49.4 kDa (heavy chain) 25.9 kDa (light chain) |

Determination of Intact Mass by Mass Spectrometry (M.S.)

The intact mass (peptide chain plus glycosylations) of UDIZ-007 and UDIZ-008 was determined by M.S. using a Vion® model ESI-Q-IMS-ToF hybrid spectrometer coupled to an Acquity® UPLC class I liquid chromatograph system. Antibodies were injected at 2 mg/mL and cleaned in line with a BEH C4, 1.7 μm, 2.1 mm×100 mm column, and a mobile phase of acetonitrile/water+0.1% formic acid. The results were processed using UNIFI® software, and the mass/charge (m/z) data were deconvoluted using the MaxEnt1 algorithm with a maximum tolerance of 100 ppm.

Figure 5A:
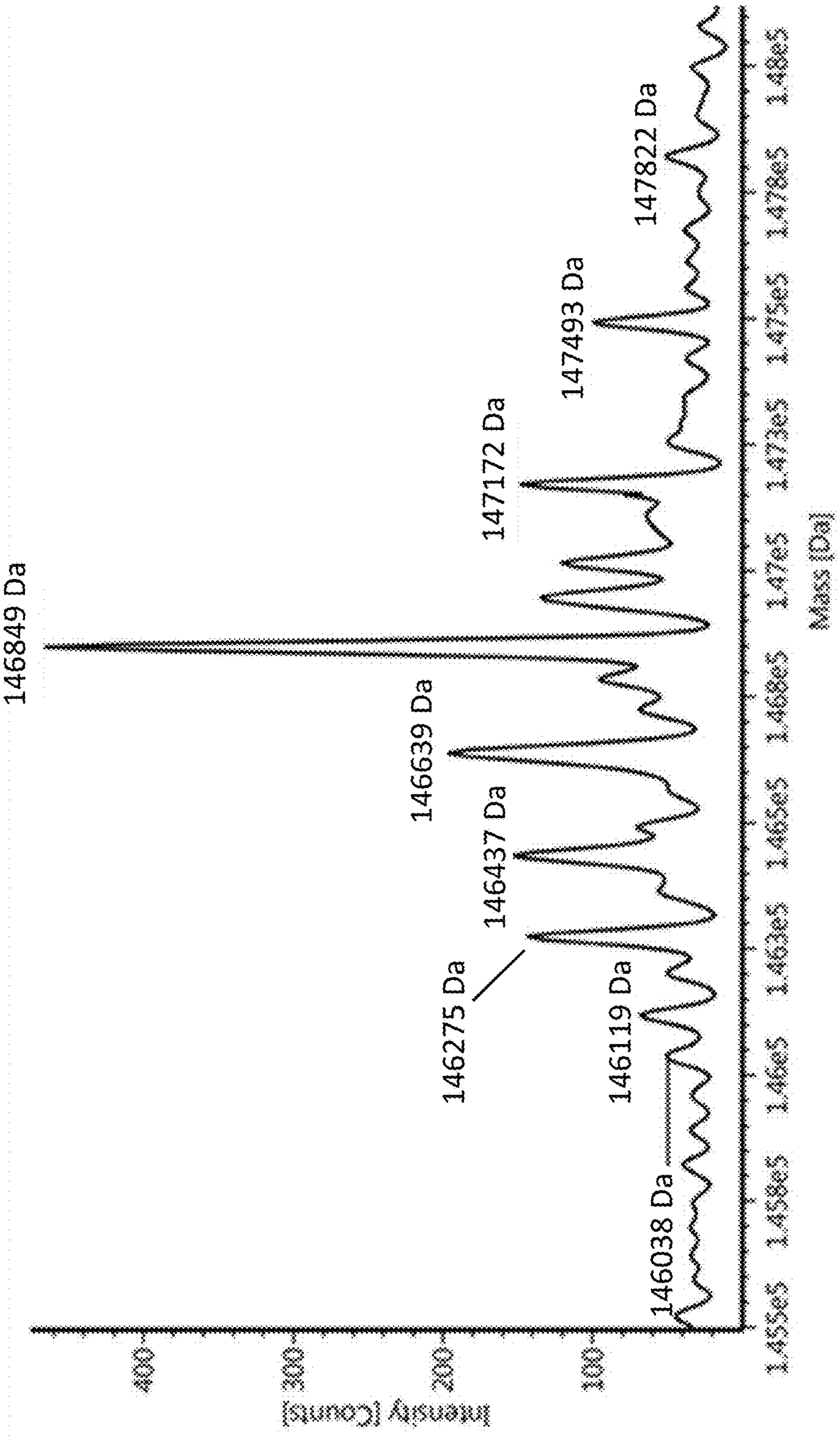
FIGS. 5A and 5B show the intact mass profile of UDIZ-007 (FIG. 5A) and UDIZ-008 (FIG. 5B). All signals were identified with a maximum error of 100 ppm.
Figure 5B:
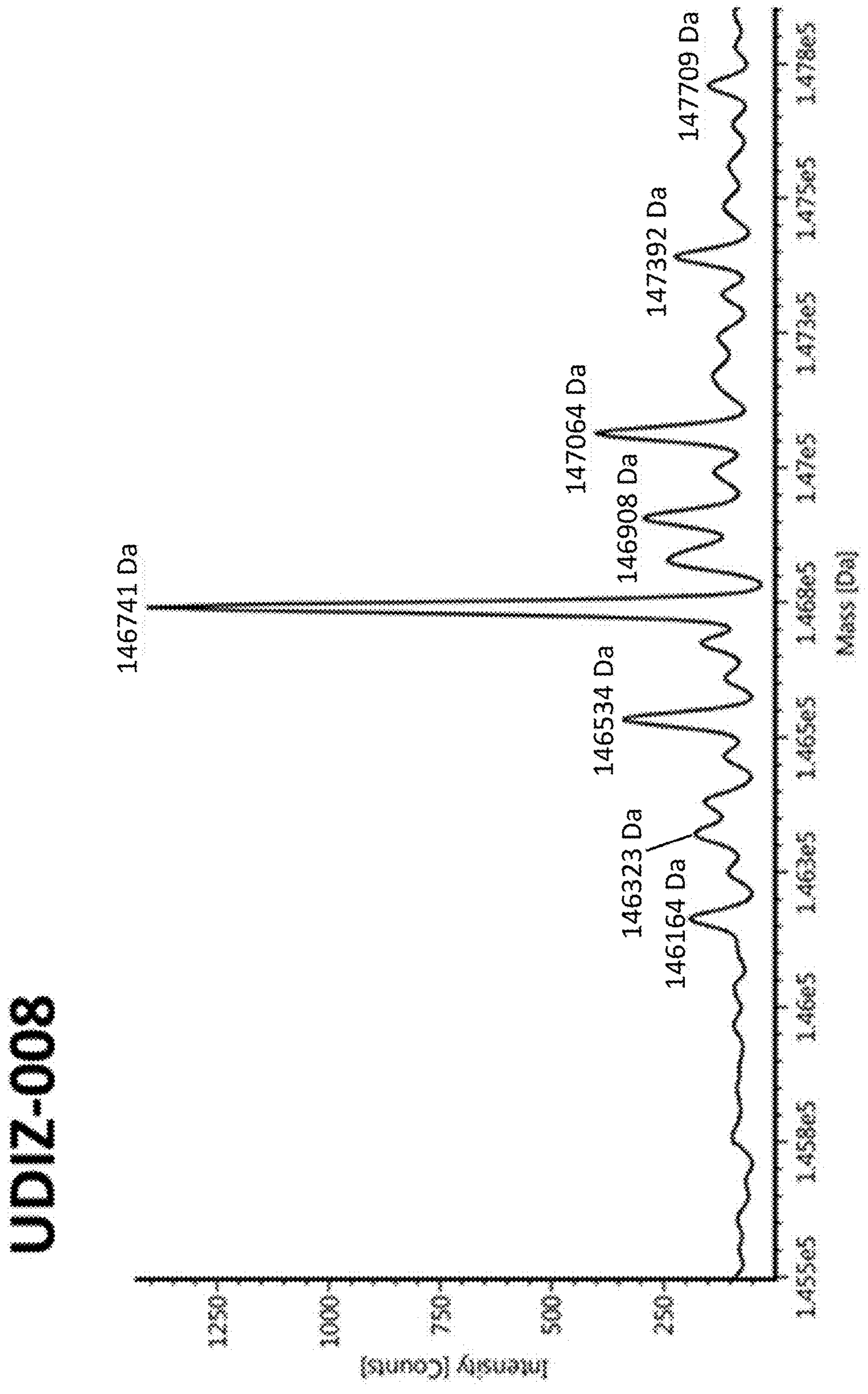

Intact Mass analysis of UDIZ-007 (FIG. 5A) and UDIZ-008 (FIG. 5B) and Table 7 revealed a predominant peak corresponding to the glycoform G0F/G0F, with masses of 146,849 Da and 146,741 Da, respectively. These main peaks differed from the calculated mass by −6.05 Da for UDIZ-007 and −4.66 Da for UDIZ-008. In addition to this principal species, both antibodies exhibited glycoforms commonly found in FDA-approved therapeutic monoclonal antibodies. These included the combinations man5/G0F (observed at 146,641 Da in UDIZ-007 and 146,534 Da in UDIZ-008), G1F/G1F (147,172 Da and 147,062 Da, respectively), and G0F/G1F (147,025 Da and 146,907 Da, respectively).

TABLE 7

Intact mass values of the major isoforms of the UDIZ-007 and UDIZ-008 antibodies. (All massvalues were obtained with error < 100 ppm)

| Antibodies | Theoretical mass aglycosylated (Da) | Experimental principal masses (Da) |
|---|---|---|
| UDIZ-007 | 143,999 | 146,437 |
| | | 146,639 |
| | | 146,849 |
| | | 147,172 |
| UDIZ-008 | 143,889 | 146,534 |
| | | 146,741 |
| | | 146,908 |
| | | 147,064 |

Thermal Stability (Tm) Determined by Protein Thermal Shift™

Figure 6A:
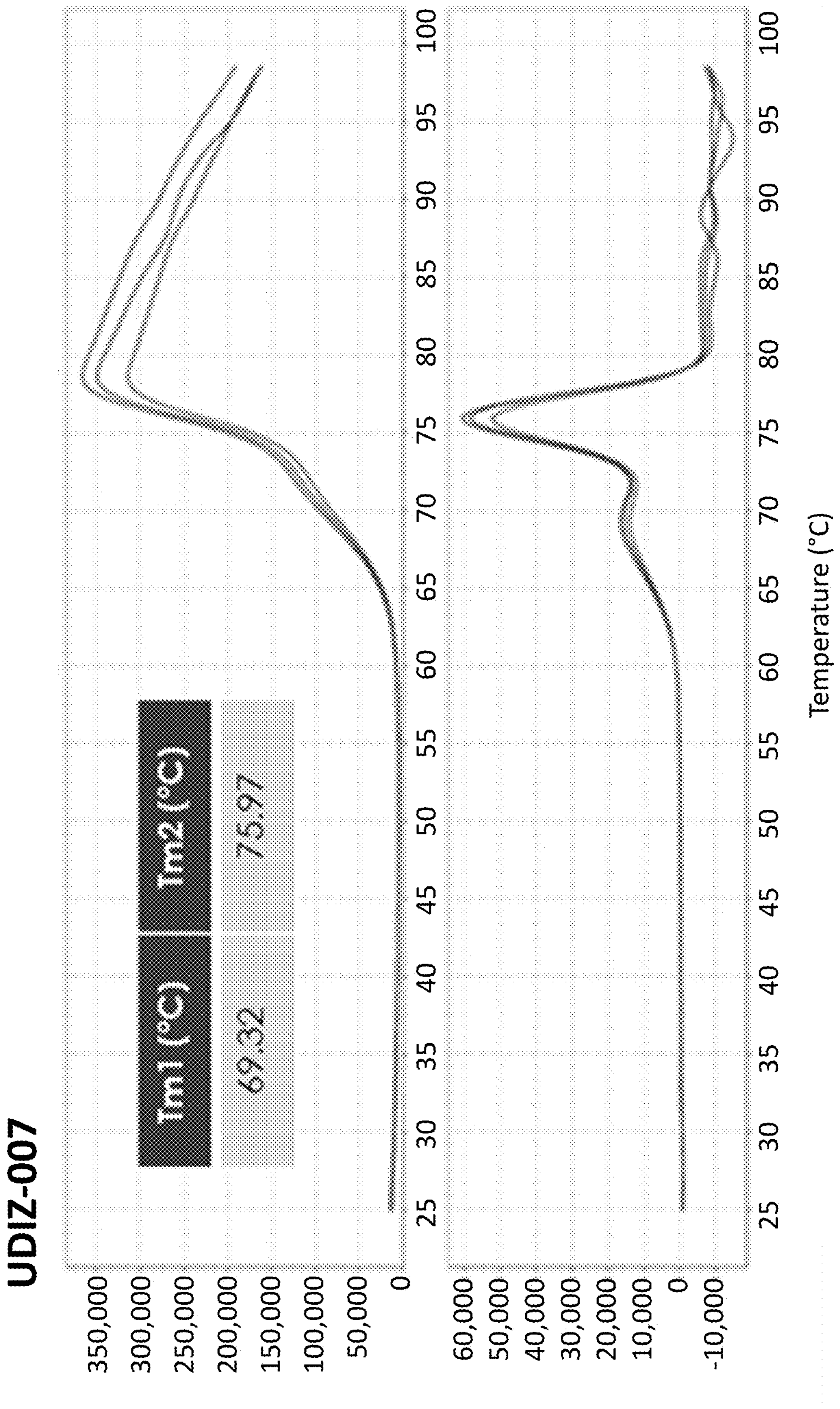
FIGS. 6A and 6B show the thermal stability profile of UDIZ-007 (FIG. 6A) and UDIZ-008 (FIG. 6B).
Figure 6B:
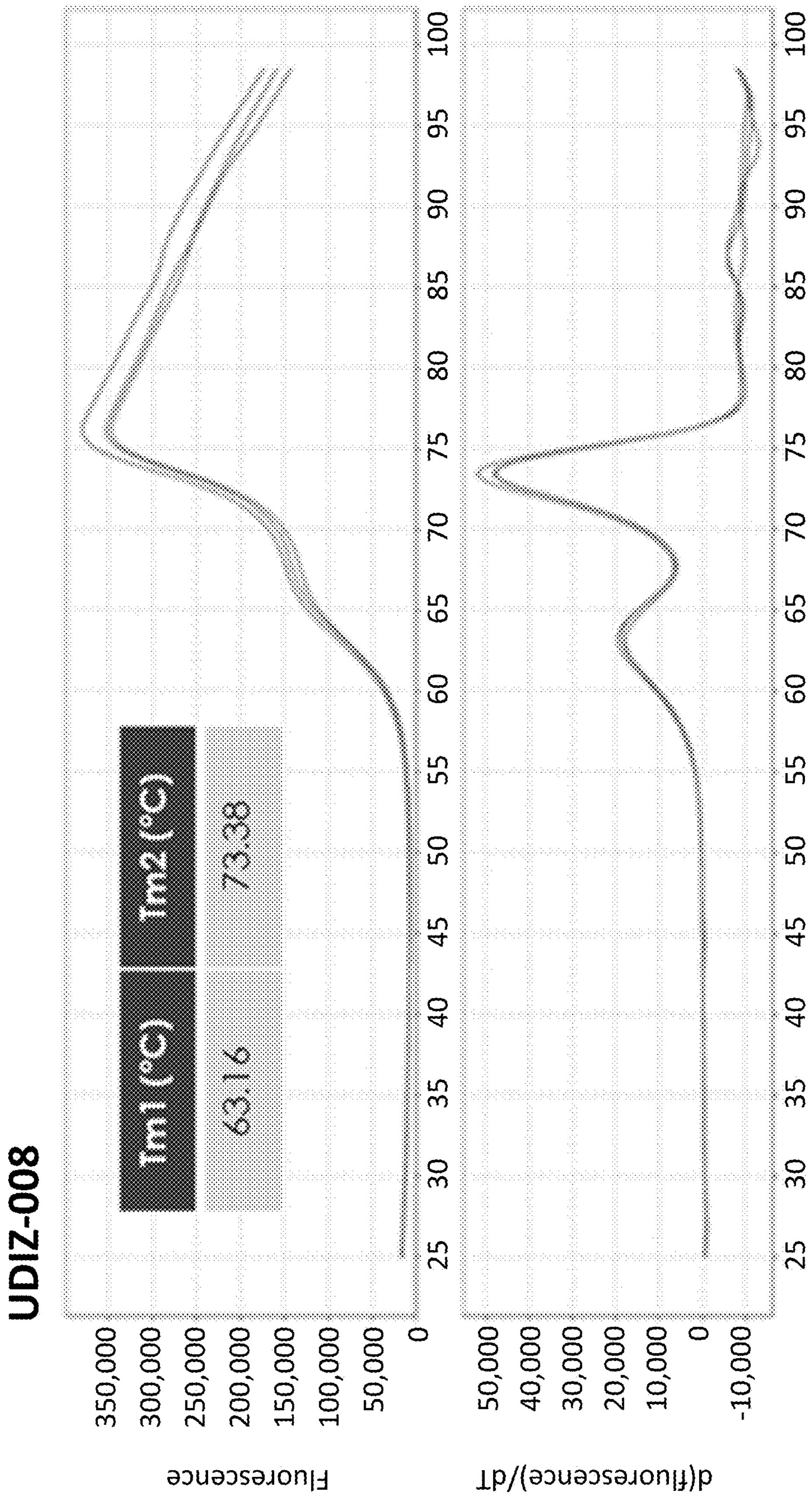

UDIZ-007 and UDIZ-008 were prepared in PBS with the Sypro Orange fluorophore. The samples were submitted for temperatures from 25° C. to 99° C., and the change in structure was observed on a 7500 Fast Real-Time PCR machine. Each sample was run in triplicate, and the results were processed with Applied Biosystems' Protein Thermal Shift™ software. The results are in FIGS. 6A and 6B. In both UDIZ-007 and UDIZ-008 two melting temperatures (Tms) were observed, the first thermal transition (Tm1) corresponding to the $C_H2$ domain, which is the least stable of the IgGs, and the second thermal transition (Tm2) corresponded to the Fab. The first Tm (Tm1) of UDIZ-007 was 69.32° C., higher by 6.0° C. than that of UDIZ-008, which is consistent with the fact that hIgG1 that was more stable than hIgG4. The second Tm (Tm2) of UDIZ-008 was 73.38° C., slightly lower (2.0° C.) than UDIZ-007, possibly due to the destabilizing effect of the IgG4 isotype.

Determination of the dissociation constant ($K_D$) for human PD-1 (hPD-1) by Surface Plasmon Resonance (SPR)

Figure 7A:
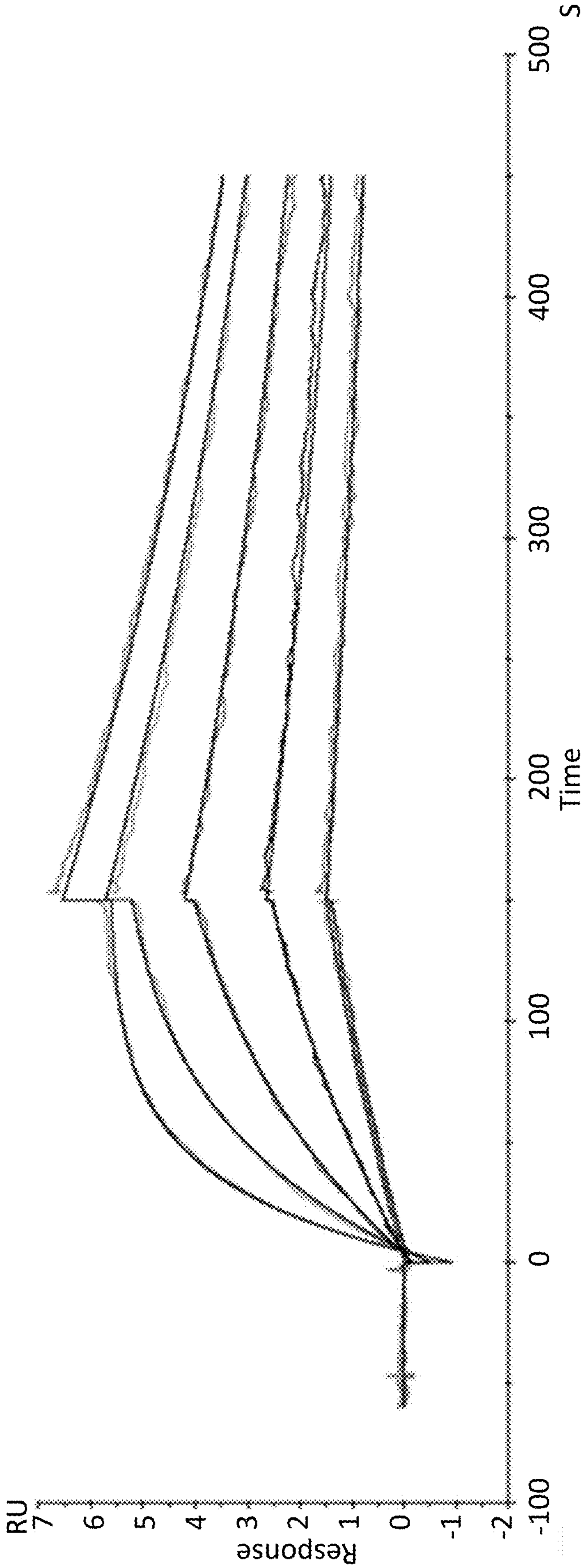
FIGS. 7A and 7B show the binding affinity of UDIZ-007 (FIG. 7A) and UDIZ-008 (FIG. 7B) for hPD-1 measured by surface plasmon resonance (SPR). Each line represents a concentration of hPD-1, including 100, 50, 25, 12.5, 6.25, and 3.125 nM, with a constant concentration of 30 nM of antibody.
Figure 7B:
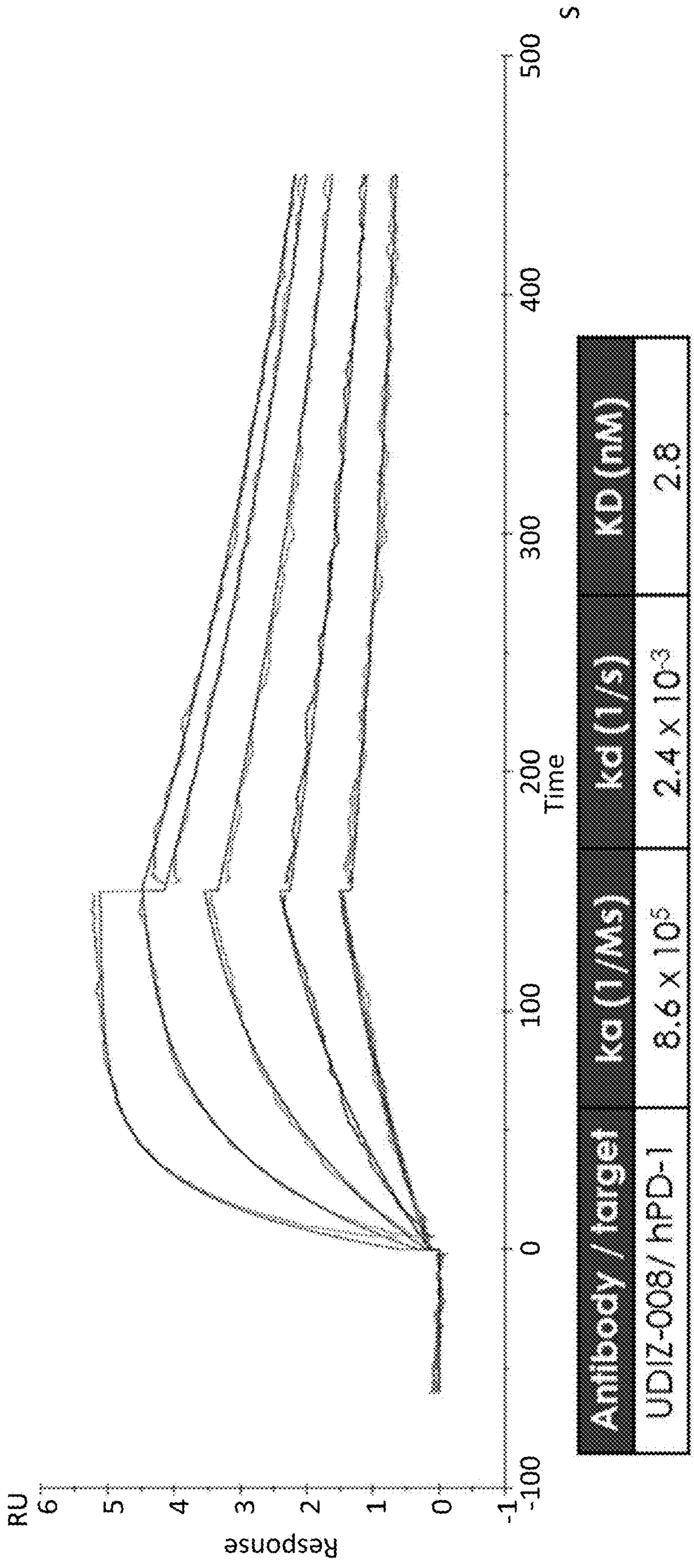

The affinity ($K_D$) of UDIZ-007 and UDIZ-008 affinity for hPD-1 was measured in a Biacore T-200. The $K_D$ was calculated as the dissociation rate constant (kd) divided the association rate constant (ka). FIGS. 7A and 7B show the sensograms corresponding to UDIZ-007 and UDIZ-008, respectively. The kinetic parameter values and $K_D$ for UDIZ-008 was 2.8 nM (Table 8), which is slightly lower than that of UDIZ-007 (3.5 nM), with both UDIZ-007 and UDIZ-008 $K_D$ values similar to that of Keytruda® (2.3 nM), determined in the same conditions. The $K_D$ value determined for Keytruda® also coincided with the value reported in the literature for this antibody (2.5 nM) (Brown et al. PLoS One. 2020; 15(3)).

TABLE 8

Kinetic parameters of UDIZ-007, UDIZ-008, and Keytruda ® by hPD-1

| Antibody | ka (1/Ms) | kd (1/s) | $K_D$ (nM) |
|---|---|---|---|
| UDIZ-007 | $6.0 \times 10^5$ | $2.1 \times 10^{-3}$ | 3.5 |
| UDIZ-008 | $8.6 \times 10^5$ | $2.4 \times 10^{-3}$ | 2.8 |
| Keytruda ® | $2.5 \times 10^5$ | $3.0 \times 10^{-3}$ | 2.3 |

Determination of $K_D$ for PD-1 of Cynomolgus Monkey (cPD-1) by SPR

Figure 8A:
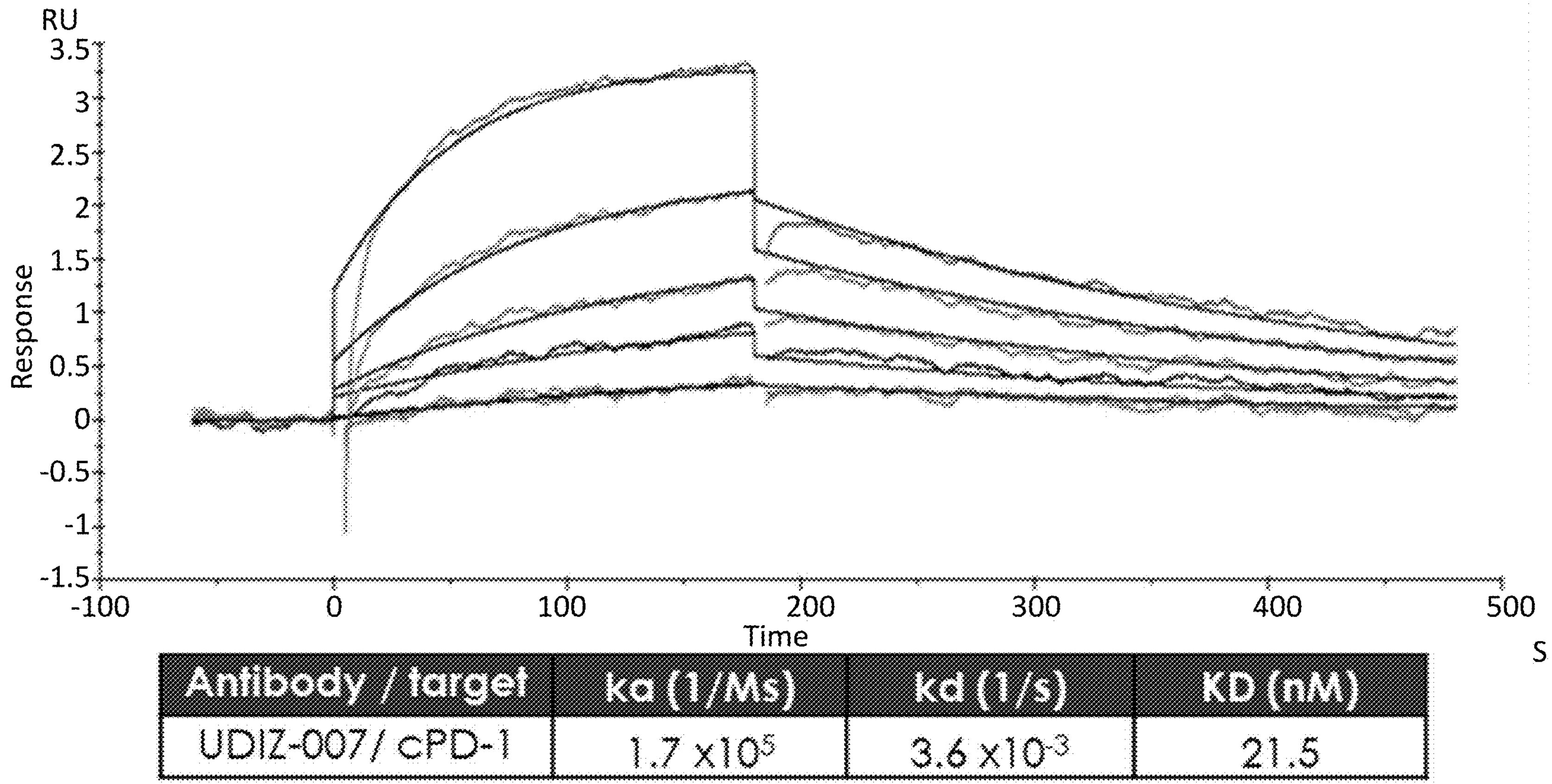
FIGS. 8A and 8B show the binding affinity of UDIZ-007 (FIG. 8A) and UDIZ-008 (FIG. 8B) for PD-1 of cynomolgus monkey (cPD-1) measured by SPR. Each line represents a concentration of cPD-1, including 100, 50, 25, 12.5, 6.25, and 3.125 nM, with 30 nM of antibody.
Figure 8B:
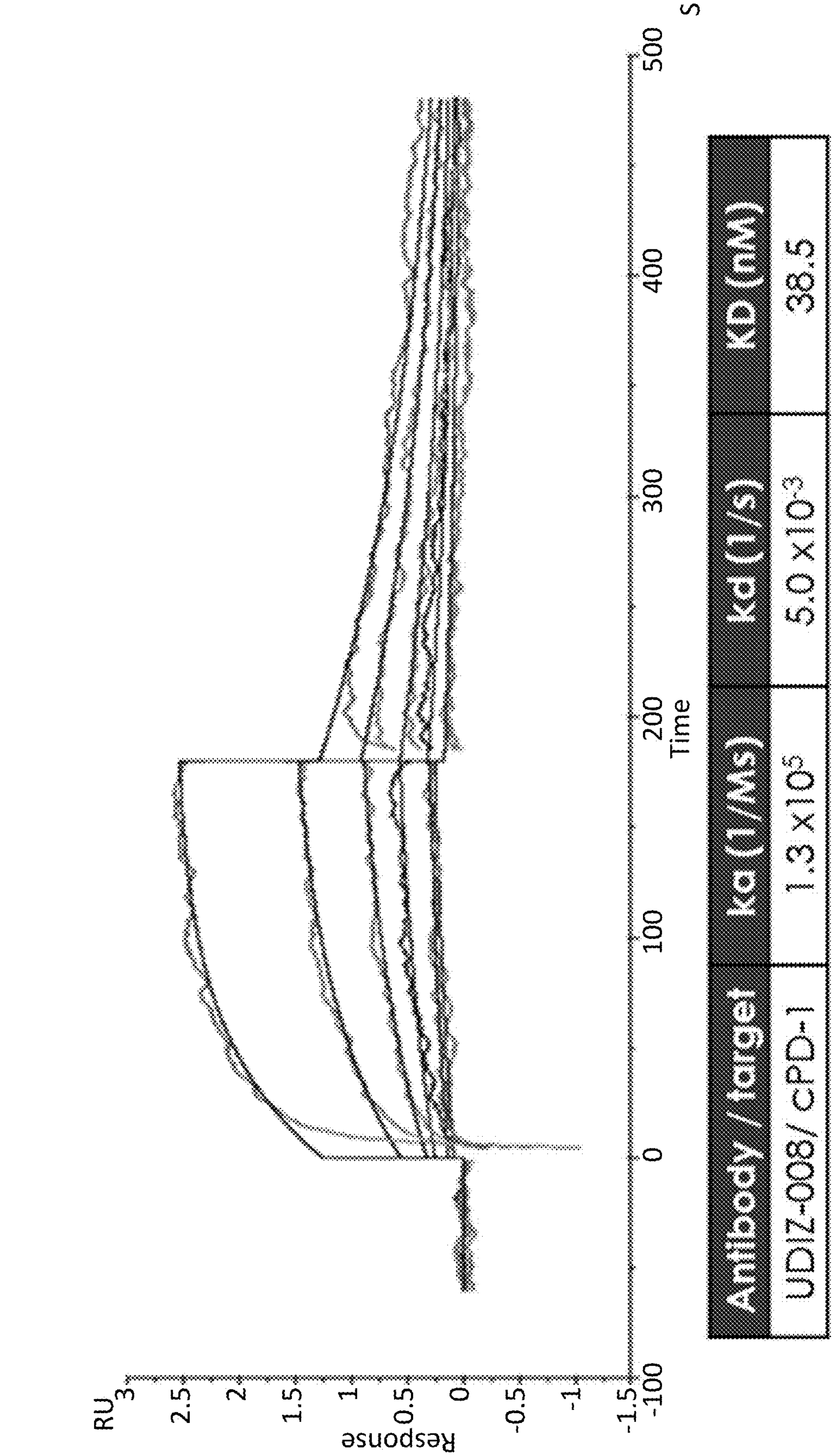

The sensograms corresponding to UDIZ-007 and UDIZ-008 are shown in FIGS. 8A and 8B and the ka, kd and $K_D$ values summarized in Table 9.

TABLE 9

Kinetic parameters of UDIZ-007 and UDIZ-008 by cPD-1

| Antibody | ka (1/Ms) | kd (1/s) | $K_D$ (nM) |
|---|---|---|---|
| UDIZ-007 | $1.7 \times 10^5$ | $3.6 \times 10^{-3}$ | 21.5 |
| UDIZ-008 | $1.3 \times 10^5$ | $5.0 \times 10^{-3}$ | 38.5 |

The $K_D$ of UDIZ-007 (21.5 nM) was lower than that of UDIZ-008 (38.5 nM). Both dissociation constants were lower than that $K_D$ of Keytruda® reported in the literature (3.6 nM) (Gjetting T, et al. MAbs. 2019; 11(4):666-680).

It should be noted that the difference between the $K_D$ of UDIZ-007 between hDP-1 and cPD-1 is less than one order of magnitude (~6×), which is indicative that the potential toxicological outcome for UDIZ-007 in non-human primates (NHP) could be translated to humans.

Example 5—Functional Characterization of UDIZ-007 and UDIZ-008 Antibodies

The following assays were used for the functional characterization of UDIZ-007 and UDIZ-008:

1. Binding ELISA to hPD-1,
2. Binding ELISA to cPD-1,
3. Mouse PD-1 binding ELISA (mPD-1),
4. Binding to related molecules of the CD28 family of receptors,
5. Binding to PD-1 in Jurkat cells,
6. Blocking PD-1/PD-L1 binding in vitro,
7. ELISA for binding to the C1q fraction of the complement system, and
8. Mixed lymphocyte reaction.

Human PD-1 (hPD-1) Binding ELISA

Figure 9A:
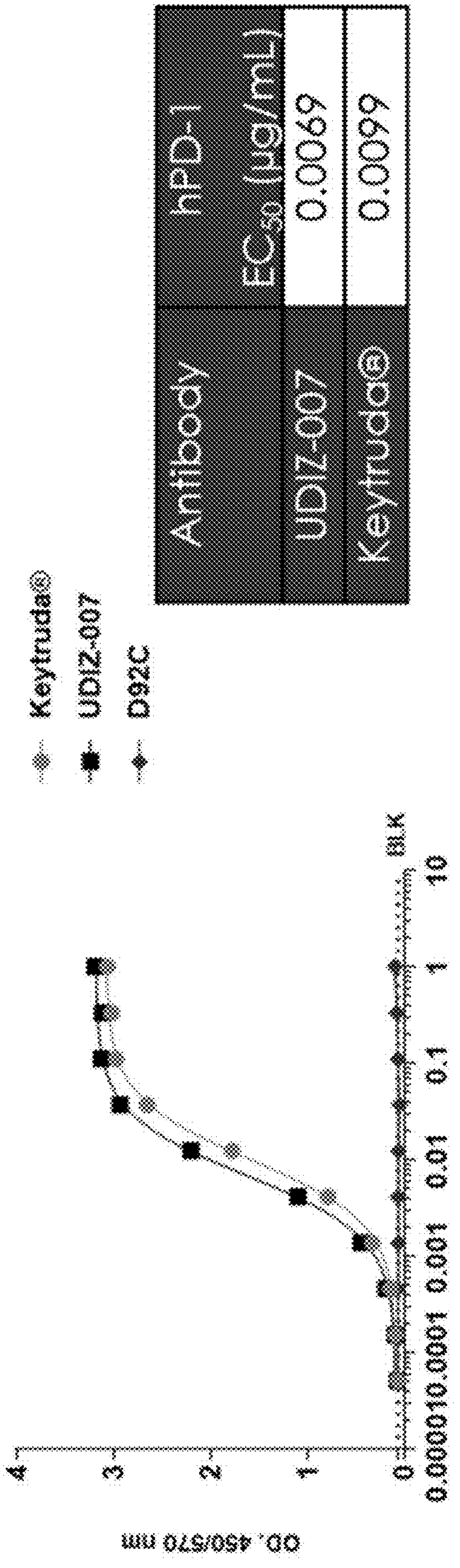
FIGS. 9A and 9B show binding of UDIZ-007 (FIG. 9A) and UDIZ-008 (FIG. 9B) to hPD-1 by ELISA. Keytruda® was used as a reference. The negative controls D92C and D55C, which have the V regions of an unrelated, anti-Lysozyme antibody, to PD-1, correspond to the IgG1-LALA and IgG4-PE isotypes, respectively.
Figure 9B:
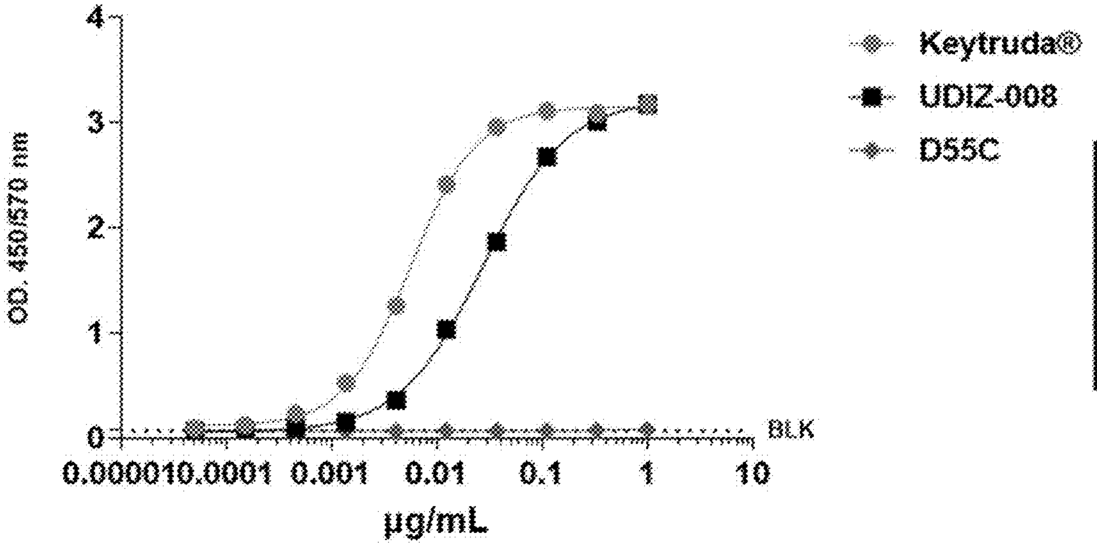

ELISA plates were coated with hPD-1 at a concentration of 0.5 μg/mL. Increasing concentrations of UDIZ-007, UDIZ-008, and Keytruda® were added to the coated ELISA plates. Antigen-antibody binding was evidenced by the addition of a horseradish peroxidase-conjugated anti-human IgG secondary antibody (Cat: ab97225, Abcam) and the subsequent addition of the substrate tetramethylbenzidine for color generation. Optical density (O.D.) values were plotted as a function of concentration (FIGS. 9A and 9B), and the dose-response curve was fitted to a 4-parameter non-linear regression model, from which the 50% effective concentration ($EC_{50}$) was determined. It should be noted that the secondary antibody had a better affinity for IgG1-LALA than for IgG4-PE, explaining why binding to hPD-1 was superior for UDIZ-007 than Keytruda®, even though in the previous section it is reported that the affinity of UDIZ-007, UDIZ-008, and Keytruda® for hPD-1 are similar.

Cynomolgus Monkey PD-1 (cPD-1) Binding ELISA

This binding assay was similar to the previous one but comprised coating the ELISA plates with cPD-1 instead of hPD-1. As shown in FIGS. 10A-10C, UDIZ-007 and UDIZ-008 have a binding pattern similar to that of Keytruda®.

Mouse PD-1 Binding ELISA (mPD-1)

This assay was similar to the hPD-1 and cPD-1 binding ELISAs but coating with mPD-1 (mPD-1) the ELISA plate. The results are shown in FIGS. 11A-11C. UDIZ-007 and UDIZ-008 do not bind to mPD-1. The lack of binding to mPD-1 by UDIZ-007 and UDIZ-008 was somewhat predictable, provided that the binding region of hPD-L1 on hPD-1, and thus the blocking site of functional antibodies, including Keytruda®, differed structurally from the binding site of mPD-L1 on mPD-1.

Binding to Related Molecules of the CD28 Receptor Family

Assessment of UDIZ-007 and UDIZ-008 binding to related molecules of the CD28 family including CD28, CTLA-4, and ICOS was performed by indirect ELISA. It is relevant to note that although the heavy and light chain variable domains of UDIZ-007 and UDIZ-008 are identical, both antibodies were evaluated in this analysis. UDIZ-007 (FIGS. 12A-12D) nor UDIZ-008 (FIGS. 13A-13D) bind CD28, CTLA-4, and ICOS. Since CD28 and ICOS have T-cell activity enhancement, whereas BTLA-4, CTLA-4, and PD-1 function as suppressors, binding of UDIZ-007 and UDIZ-008 to hPD-1 but not to members of the CD28 family, is expected to minimize the risk of adverse effects due to the lack of binding to other molecules involved in the T-cell immune regulation.

PD-1 Binding in Jurkat Cells

Assessment of binding to hPD-1 expressed on the cell surface was performed by flow cytometry using Jurkat cells stably transfected to overexpress hPD-1. The binding of hPD-1-specific antibodies was detected by staining with a phycoerythrin-coupled anti-hIgG secondary antibody. Both, UDIZ-007 (FIG. 14A) and UDIZ-008 (FIG. 14B) bind hPD-1 in the concentration range of 0.0001 to 0.1 μg/mL, with $EC_{50}$ values only departing 3× from Keytruda® (FIG. 14C).

Blocking hPD-1:hPD-L1 Binding in the Cellular Context

The biological in vitro activity of UDIZ-007 and UDIZ-008 was assessed by their ability to block hPD-1 binding to hPD-L1 in in vitro cell co-culture. This assay involved plating a cell line (CHO-K1) constitutively expressing hPD-L1 and a T-cell receptor (TCR) activator. CHO-K1 was incubated with a recombinant Jurkat cell line that stably overexpresses hPD-1 and contains a conditional expression of the luciferase gene under the control of nuclear factor of activated T-cells (NFAT) response elements located upstream of the TATA promoter. The NFAT stimulation is monitored by measuring luciferase activity and the fold induction of luminescence is obtained by the effect of anti-PD-1 antibodies on co-cultured Jurkat cells and CHO-K1 as shown in FIGS. 15A-15B. Both UDIZ-007 and UDIZ-008 blocked the interaction between hPD-1 and hPD-L1 with $EC_{50}$ values of 0.1229 and 0.1372 μg/mL, respectively (FIG. 15C). Keytruda® and Opdivo® were used as a reference.

Blockade of hPD-1 Interaction with hPD-L1 and hPD-L2

Figure 16A:
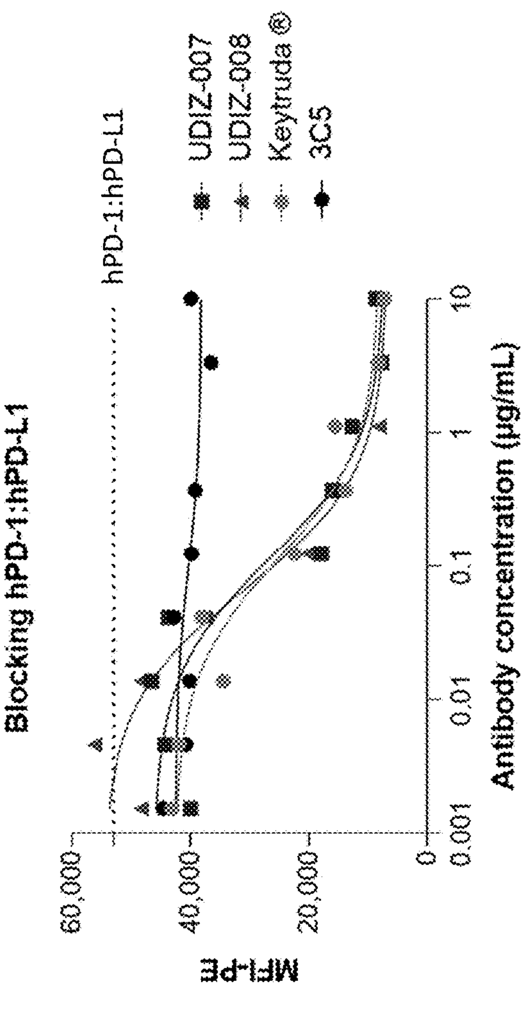
FIGS. 16A-16B show the flow cytometry of hPD-L1 and hPD-L2 blockade by UDIZ-007 and UDIZ-008.
Figure 16B:
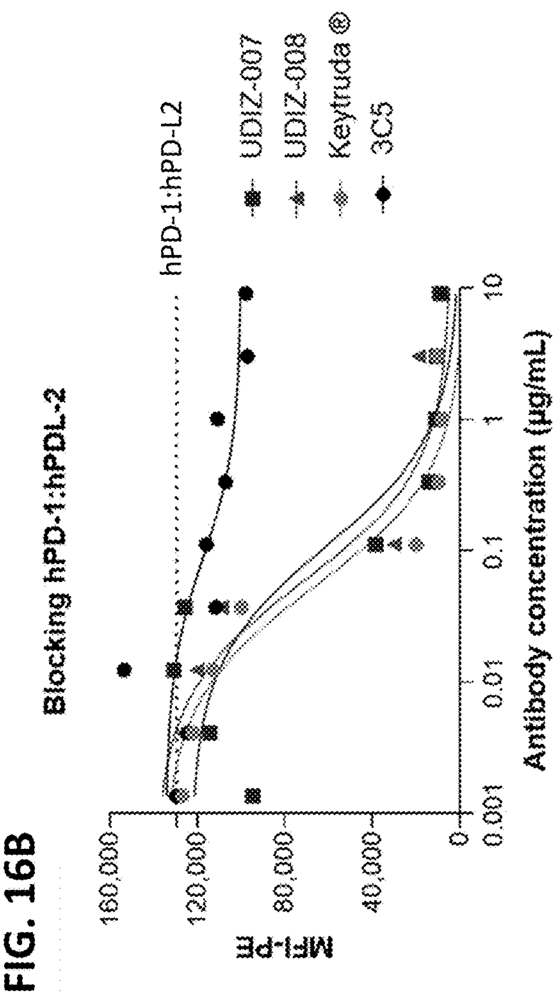

The functionality of UDIZ-007 and UDIZ-008 in blocking hPD-1:hPD-L1 and hPD-1:hPD-L2 interactions were assessed by flow cytometry (FIGS. 16A-16B). Both antibodies competently inhibited the binding of human hPD-1: PD-L1 and hPD-L2.

Mixed Lymphocyte Reaction (MLR)

Figure 17:
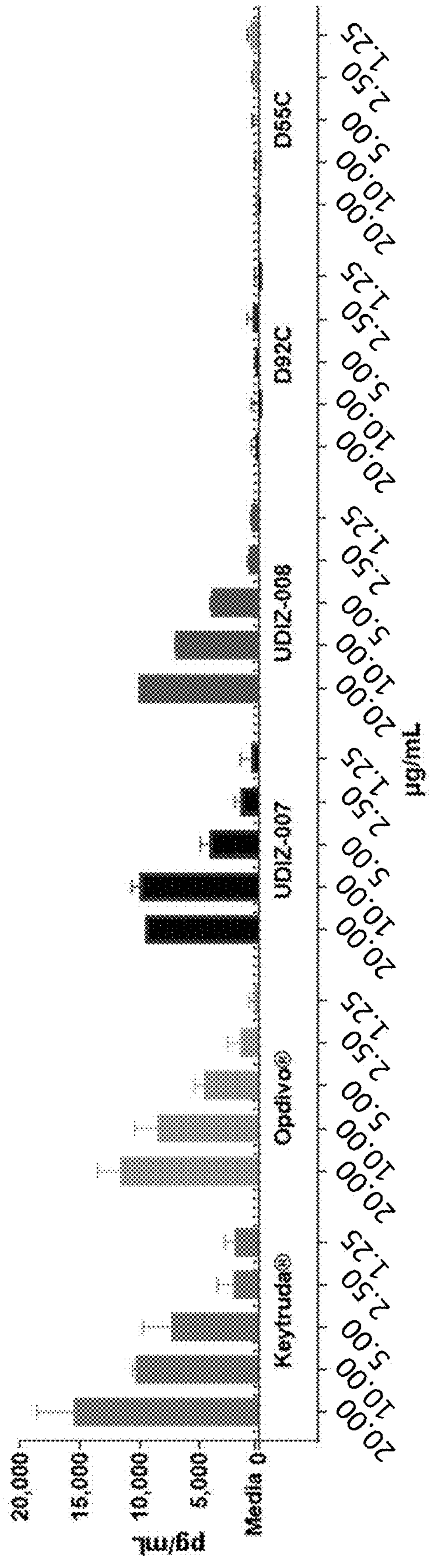
FIG. 17 shows UDIZ-007 and UDIZ-008 IFN-γ production in supernatant of a functional lymphocyte mixed reaction assay. Keytruda® and Opdivo® were used as references. D92C and D55C were used as negative controls.

This in vitro functional assay served as a precursor to the efficacy assays performed in the examples below, as it constituted an activity assay that evaluates the response of the T-cells and effector immune cells from human donors, and thus, unlike the cell-blocking assays in the previous sections, cells naturally expressing hPD-1 and hPD-L1 are used in this assay. Briefly, a primary co-culture of previously activated CD4+ T lymphocytes ($1\times10^5$ cells/well) was incubated with allogeneic dendritic cells ($1\times10^4$ cells/well) in the presence or absence of anti-PD-1 antibody. Activated CD4+ T lymphocytes and allogeneic dendritic cells were obtained from differentiating PBMCs (peripheral blood mononuclear cells) isolated from healthy donors and activated with anti-CD3 and CD28 antibodies (T-lymphocytes) or differentiated with IL-4 to GMCSF (dendritic cells). If antibodies block the hPD-1:hPD-L1 interaction, IFNγ is released. If the interaction is not blocked, T-lymphocytes remain inactivated and do not release IFNγ. As shown in FIG. 17, both UDIZ-007 and UDIZ-008 increased IFNγ release in a dose-response manner, a phenomenon consistent with that observed with Keytruda® and Opdivo®, used as reference antibodies. Notably, the data presented in FIG. 17 are an example of several independent assays showing similar results.

Example 6—FC Functional Characterization of UDIZ-007 and UDIZ-008

The Fc characterization included:

1. Assessment of the interaction with the human neonatal receptor (FcRn) by SPR
2. Interaction with FcγRIIIa (CD16a), FcγRIIa (CD32a), and FcγRI (CD64) receptors by SPR
3. Binding to human Cq1 by ELISA.

Figure 18A:
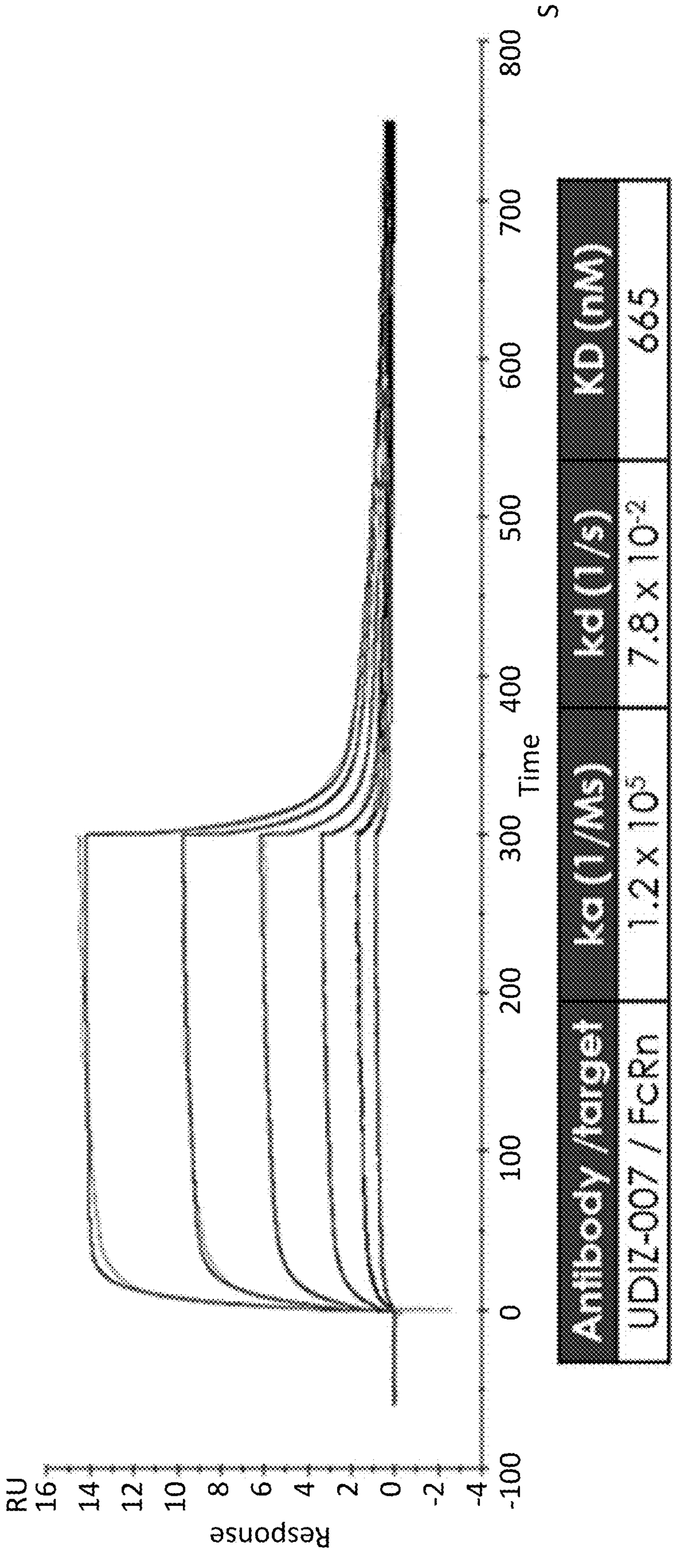
FIGS. 18A-18B show the affinity of UDIZ-007 (FIG. 18A) and UDIZ-008 (FIG. 18B) for the hFcRn receptor as assessed by SPR.
Figure 18B:
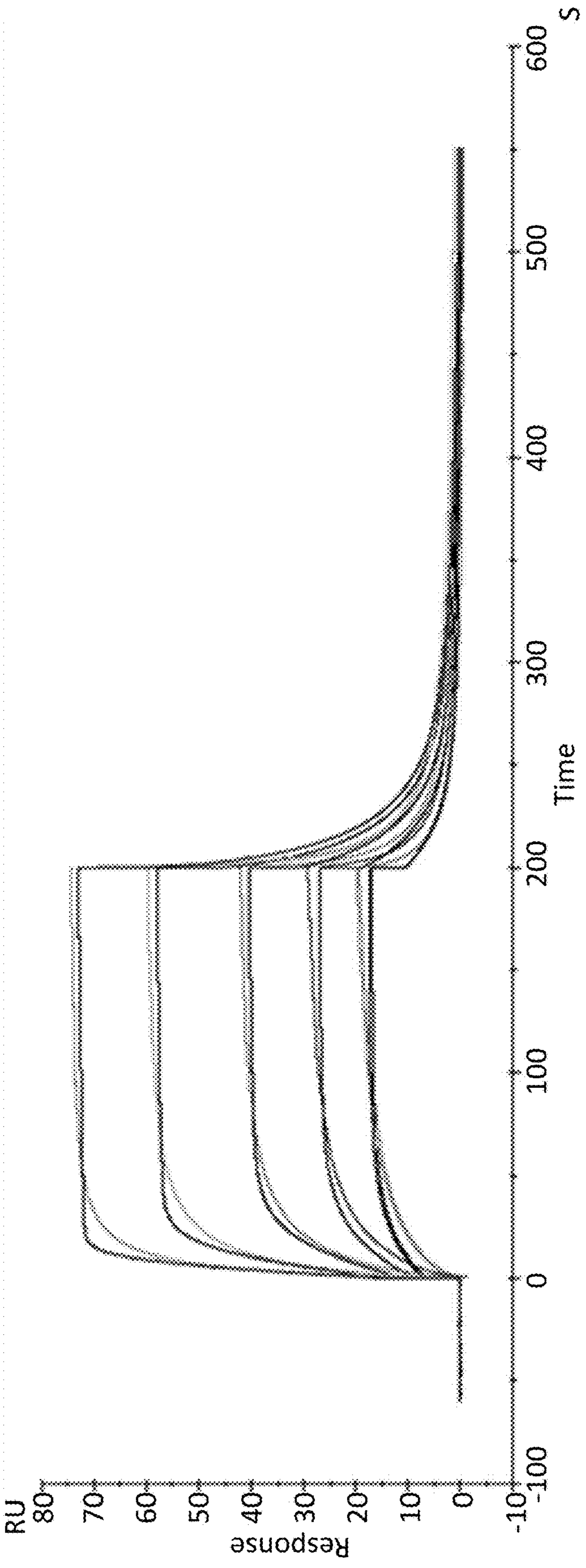

Determination of the Affinity Constant ($K_D$) for the Human Neonatal Receptor (hFcRn) by SPR This assay was performed using a CM5 CHIP sensitized with human FcRn, to which UDIZ-007 and UDIZ-008 antibodies were flown in a range of concentrations of 18.75 to 300 nM. The sensograms of UDIZ-007 and UDIZ-008 binding to FcRn are shown in FIGS. 18A and 18B. The $K_D$ of UDIZ-007 (665 nM) was in the same order of magnitude as other IgG1s, such as adalimumab (672 nM) and infliximab (727 nM).

Determination of the $K_D$ or FcγRI, FcγRIIa, and FcγRIIIa Receptors Using SPR

Determination of the $K_D$ of UDIZ-007 and UDIZ-008 for the receptors FcγRI (CD64), FcγRIIa (CD32a), and FcγRIIIa (CD16a) was performed using a CM5 CHIP sensitized with an anti-Histidine antibody that captured the respective receptors. UDIZ-007 and UDIZ-008 were flown over the CHIP in the range of concentrations of 62.5 nM to 1,000 nM.

Table 10 summarizes the ka, kd and $K_D$ values of UDIZ-007, UDIZ-008 and the control antibody D63E to the FcγRs. In contrast to D63E, UDIZ-007 and UDIZ-008, do not bind to FcγRI, FcγRIIa, and FcγRIIIa, which are essential for triggering effector functions. Human FcγRIIIa is expressed on innate immune cells such as macrophages and N.K. cells and is the most relevant receptor for antibody-dependent cellular cytotoxicity (ADCC) of therapeutic antibodies. The two polymorphic forms of the receptor, FcγRIIIa 158V and FcγRIIIa 158F, were used for characterization, where 158V has been associated with higher cytotoxic activity. Therefore, as expected UDUZ-007 and UDIZ-008 should have low toxicity due to low or no binding to the FcγRs.

TABLE 10

Affinity values of D63E, UDIZ-007 and UDIZ-008 for FcγRI, FcγRIIa, FcγRIIIa 158V and FcγRIIIa 158F receptors

| | FcγRI (CD64) | | | FcγRIIa (CD32a) | | | FcγRIIIa 158V & 158F (CD16a) | | |
|---|---|---|---|---|---|---|---|---|---|
| Parameter | D63E | UDIZ-007 | UDIZ-008 | D63E | UDIZ-007 | UDIZ-008 | D63E | UDIZ-007 | UDIZ-008 |
| Kα (1/ms) | $2.5 \times 10^{4}$ | ND | ND | $7.8 \times 10^{2}$ | ND | ND | $3.0 \times 10^{3}$ (158V) | ND | ND |
| Kd (1/s) | $8.6 \times 10^{-4}$ | ND | ND | $5.1 \times 10^{-3}$ | ND | ND | $7.2 \times 10^{-4}$ (158V) | ND | ND |
| KD (M) | $3.4 \times 10^{-8}$ | — | — | $6.5 \times 10^{-6}$ | — | — | $2.4 \times 10^{-7}$ (158V) | — | — |

ND: Not Detectable

ELISA for Binding to the C1q Fraction of the Complement System

Binding to the C1q fraction of the human complement system (FIGS. 19A-19C) was determined by indirect ELISA using MabThera®, a commercial IgG1 therapeutic antibody (Rituximab) that binds FcγRs, as a positive control. The results indicate that UDIZ-007 (FIG. 19A) and UDIZ-008 (FIG. 19B), being IgG1-LALA or IgG4-PE, did not bind to the C1q fraction of the human complement system, in contrast with Rituximab that is a hIgG1 and thus, binds C1q.

Example 7—Epitope Mapping

The epitope of UDIZ-007 was determined by crosslinking mass spectrometry (XL-MS). Since UDIZ-007 has the same V regions as UDIZ-008, it was assumed that both antibodies bind the same epitope.

Briefly, hPD-1 and UDIZ-007 were incubated at a 2.8 to one ratio and the complex was incubated with deuterated cross-linking agents and subjected to multi-enzyme digestion. After enrichment, the mixture was analyzed using high-resolution mass spectrometry (nLC-Q-Exactive mass spectrometry).

The epitope was located at residues 80-115 when numbered in accordance with SEQ ID NO: 25 (AAFPEDRSQPGQDCRFRVTQLPNGRDFHMSVVRARR, SEQ ID NO: 29) (FIG. 20) and encompassed the C'D loop, and β-strands D and E. The N-terminal region of hPD-1 (residues 80-104: AAFPEDRSQPGQDCRFRVTQLPNGR (SEQ ID NO: 26) was involved in the interaction with the three HCDRs whereas, the C-terminal region (residues 105-115: DFHMSVVRARR (SEQ ID NO: 27) was bound by HCDR2 and LCDR1 and LCDR2. LCDR3 was not identified as in contact hPD-1.

Figure 21A:
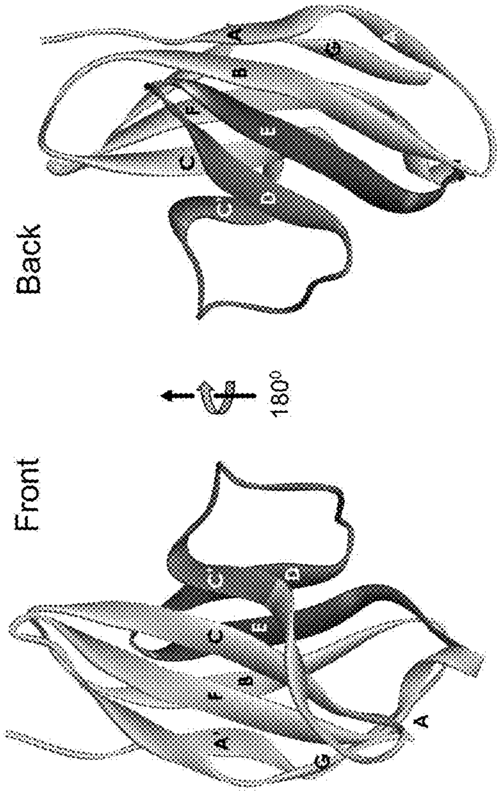
FIG. 21A shows a ribbon representation of hPD1 (PDBID: 4ZQK) indicating its secondary structure and the residues identified as in contact with UDIZ-007.
Figure 21B:
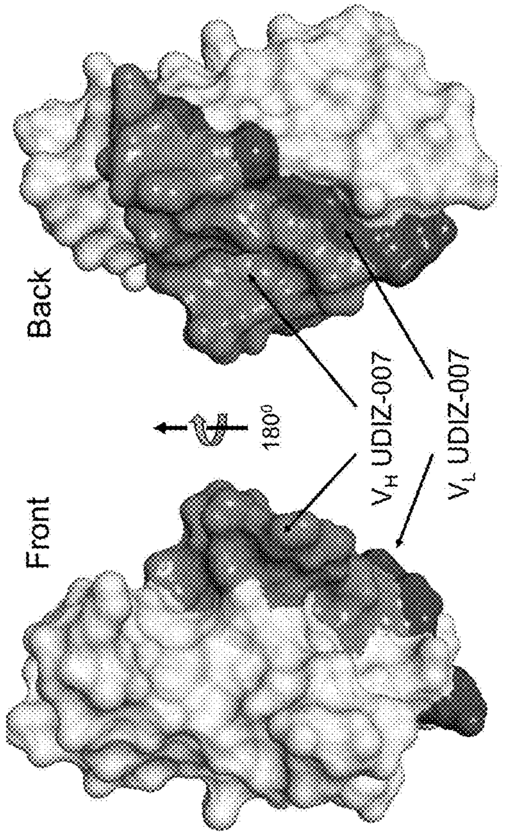
FIG. 21B shows the solvent accessible surface representation of hPD-1 in the same orientation as the ribbon representation mapping the exposed surface of the epitope.
Figure 21C:
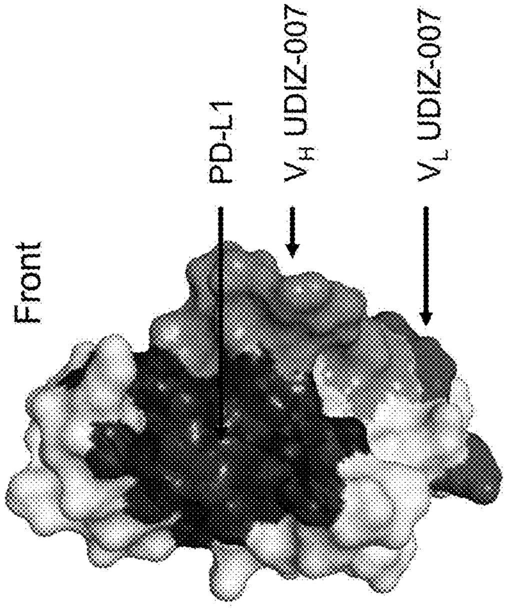
FIG. 21C shows the UDIZ-007 epitope and the interface with hPD-L1. The hPD-L1 binding site was determined with PDBePISA (Proteins, Interfaces, Structures and Assemblies; www.ebi.ac.uk/pdbe/pisa/) using the PDB structure 4ZQK. The Figures were generated with BIOVIA Discovery Studio 2020.

FIG. 21A shows a ribbon representation of hPD1 (PDBID: 4ZQK) indicating its secondary structure and the residues identified as in contact with UDIZ-007. FIG. 21B shows the solvent accessible surface representation of hPD-1 in the same orientation as the ribbon representation, mapping the exposed surface of the epitope. FIG. 21C shows the UDIZ-007 epitope and the interface with hPD-L1.

Remarkably, the epitope UDIZ-007 (and by extension UDIZ-008) does not overlap with the residues involved in the hPD-1:hPD-L1 interaction. hPD-1 binds hPD-L1 with the front β-sheet face built by CC'FG strands (FIG. 21C) whereas, hPD-1 binds UDIZ-007 with the C'D loop, and β-strands D and F. These β-strands are on the opposite side of hPD-L1 binding site, suggesting that UDIZ-007 MOA is not by directly outcompeting hPD-L1 interaction with hPD-1. The C'D loop, on the other hand, is highly flexible and in fact is unstructured and missed in some experimental structures. Also, it has different conformations free or in complex with diverse ligands and important differences have been found at the PD-L1 binding site due to single amino acid substitutions in hPD-1 leading to notable differences between the human and the mouse ortholog in the C'D loop. Thus, an alternative (or complementary) explanation to the UDIZ-007/008 MOA, could be that the binding of UDIZ-007 to the C'D loop of hPD-1 stabilizes a conformation that prevents the interaction with hPD-L1.

A comparison with the epitopes recognized by anti-PD-1 antibodies of known structure in complex with hPD-1 (SEQ ID NO: 28) (FIG. 22) shows that UDIZ-007 epitope is unique. Overall, three regions can be identified in the epitopes of anti-PD-1 antibodies: (1) the N-loop and β-strands A' and A (residues 25-43); (2) the C'D loop and C and C' β-strands (residues 59-100); and (3) the FG loop (residues 121-144). Out of the 16 different antibodies from 21 crystallography structural data, four (Nivolumab, GY-5, D12, and Toripalimab) bind regions 1, 2 and 3, one antibody (NBO1a) binds regions 1 and 3, and most of the antibodies (11 structures) bind regions 2 and 3 only. UDIZ-007 epitope partially overlaps with region 2 and binds a region of hPD-1 mainly located in the β-strand between regions 2 and 3. None of the antibodies in FIG. 22 have epitopes that map onto this region of hPD-1.

Figure 22:
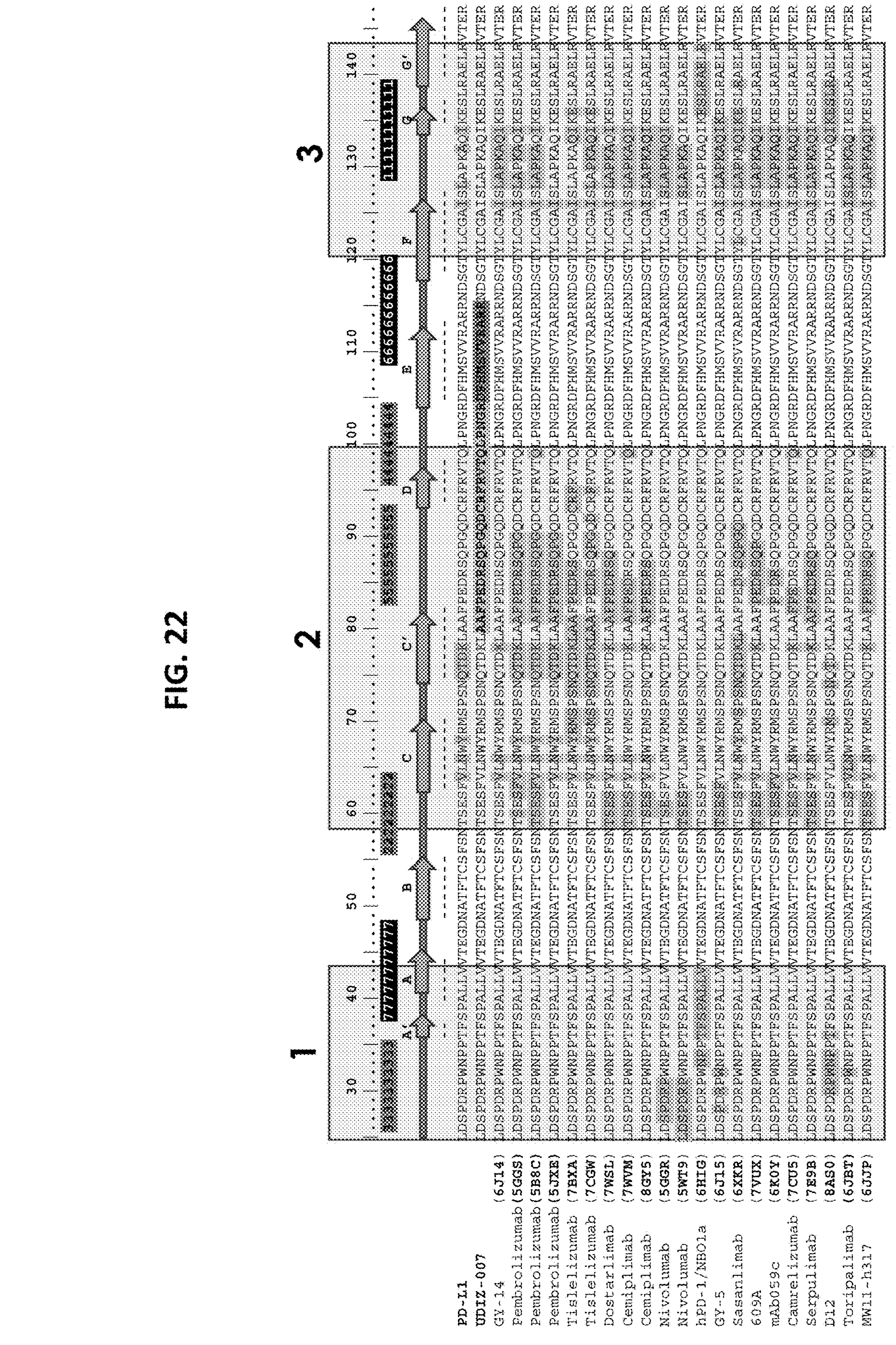
FIG. 22 shows a comparison of UDIZ-007 epitope with the epitopes identified in crystallographic structural data from 21 antibody structures (16 anti-PD-1 unique antibodies) of known structures in complex with hPD-1 (SEQ ID NO: 28). Three structures for Pembrolizumab, two for Nivolumab, two for Cemiplimab, and two Tislelizumab solved in different crystallization conditions are included in the Figure to show slight differences in the epitope recognized by the same antibody. The interface between the antibodies and hPD-1 were determined by PDBePISA. Only residues (25-147) of hPD-1 where at least one anti-PD-1 antibody binds hPD-1 are highlighted in gray. The boxes (1-3) enclose the epitope regions recognized by the antibodies. UDIZ-007 epitope is indicated in the hPD-1 sequence as in FIG. 20. On top, the residues identified as antagonist (light gray) or agonist (dark grey) epitopes as reported at Kensuke Suzuki et al. 2023 (Sci Immunol. 2023 Jan. 13; 8(79)).

The epitope specificity plays an important role in defining the anti-PD-1 antibody functions. For instance, the evaluation of antibodies targeting hPD-1 in a functional in vitro assay revealed that Pembrolizumab is a slightly more effective PD-1 blocker than Nivolumab. As shown in FIG. 22, Pembrolizumab and Nivolumab bind different hPD-1 epitopes. Further, a recently systematic analysis of a panel of anti-PD-1 antibodies binding hybrids of hPD-1/mPD-1 indicated that the membrane-proximal extracellular region of PD-1 has agonist activity in sharp contrast to the binding of the membrane-distal region by antagonistic antibodies (Suzuki K, et al. Sci Immunol. 2023; 8(79)). Therefore, it is reasonable to expect that the UDIZ-007 unique epitope could lead to differences in oncology indications with respect to the approved antibodies or being efficacious where the known antibodies have shown limited application.

Moreover, UDIZ-007 and UDIZ-008 alone, in combination with other approved anti-PD1 approved antibodies, or as part of multi-specific therapeutics formats that link UDIZ-007 and UDIZ-008 with antibodies binding non-overlapping epitopes to enhance the specificity of current anti-PD1 therapeutic antibodies could be valuable new therapeutic options to treat cancer.

Example 8—Pilot Efficacy Study of UDIZ-007 AND UDIZ-008

The efficacy of UDIZ-007 and UDIZ-008 was evaluated in a syngeneic tumor model. Female B-hDP-1 transgenic mice (C57BL/6-Pdcd1tm1(PDCD1)/Bcgen), in which exon 2 of the mouse PD-1 gene encoding the extracellular domain was replaced with exon 2 of hPD-1. Colon carcinoma ($1\times10^6$ hPD-L1-MC38 cells) were subcutaneously implanted with in the right lower flank of each mouse. The cells had replaced the mouse H2-t23 and PD-L1 genes with the coding sequence of human HLA-E and hPD-L1, causing them to highly express hPD-L1. Once the tumors reached a size of 75-125 $mm^3$, the mice were stratified into five groups of six animals each (Table 11). The five groups included three antibodies to be tested: UDIZ-007, UDIZ-008, and Keytruda®, and two isotype controls: D92C (D.13 IgG1-LALA) and D55C (D1.3 IgG4-PE).

TABLE 11

Experimental groups for the efficacy model.

| Group | Treatment | Dose (mg/Kg) | Route of administration | Number of total doses | Experimental administration days |
|---|---|---|---|---|---|
| 1 | D92C (IgG1-LALA) | 10 | I.P. | 6 | 0, 3, 7, 10, 14, 17 |
| 2 | D55C (IgG4-PE) | 10 | I.P. | 6 | 0, 3, 7, 10, 14, 17 |
| 3 | Keytruda ® (pembrolizumab) | 10 | I.P. | 6 | 0, 3, 7, 10, 14, 17 |
| 4 | UDIZ-007 (IgG1-LALA) | 10 | I.P. | 6 | 0, 3, 7, 10, 14, 17 |
| 5 | UDIZ-008 (IgG4-PE) | 10 | I.P. | 6 | 0, 3, 7, 10, 14, 17 |
| 6 | No treatment and no tumor | 0 | N.A. | — | — |

I.P.: intraperitoneal; NA: not applicable.

Figure 23:
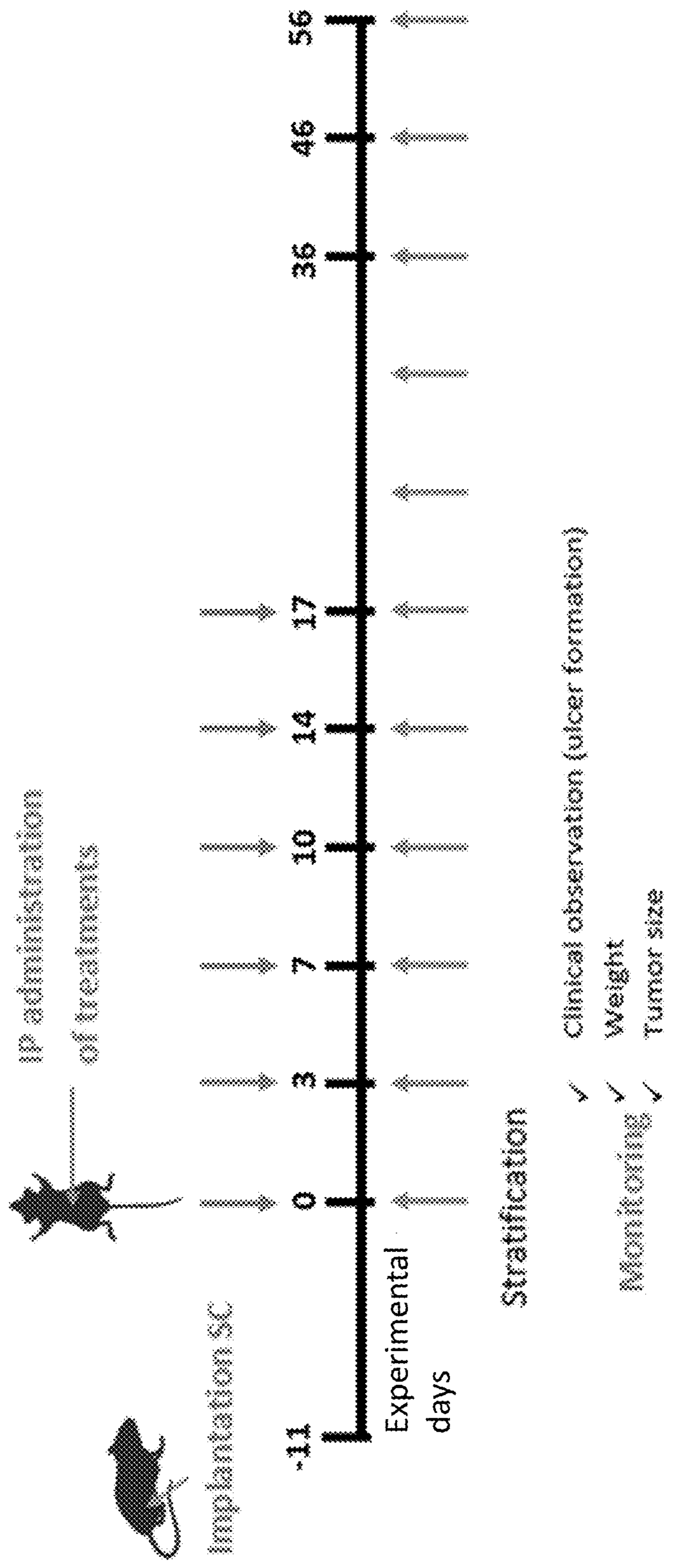
FIG. 23 shows the efficacy study design of UDIZ-007 and UDIZ-008.

The dosing schedule (FIG. 23) consisted of six intraperitoneal (I.P.) administrations for each treatment, as shown in Table 11. Monitoring of the animals was performed from day 0 (start of treatments) to day 56. During this period, weight loss, tumor volume, or tumor size were measured, and the formation of tumor ulceration was monitored.

Figure 24:
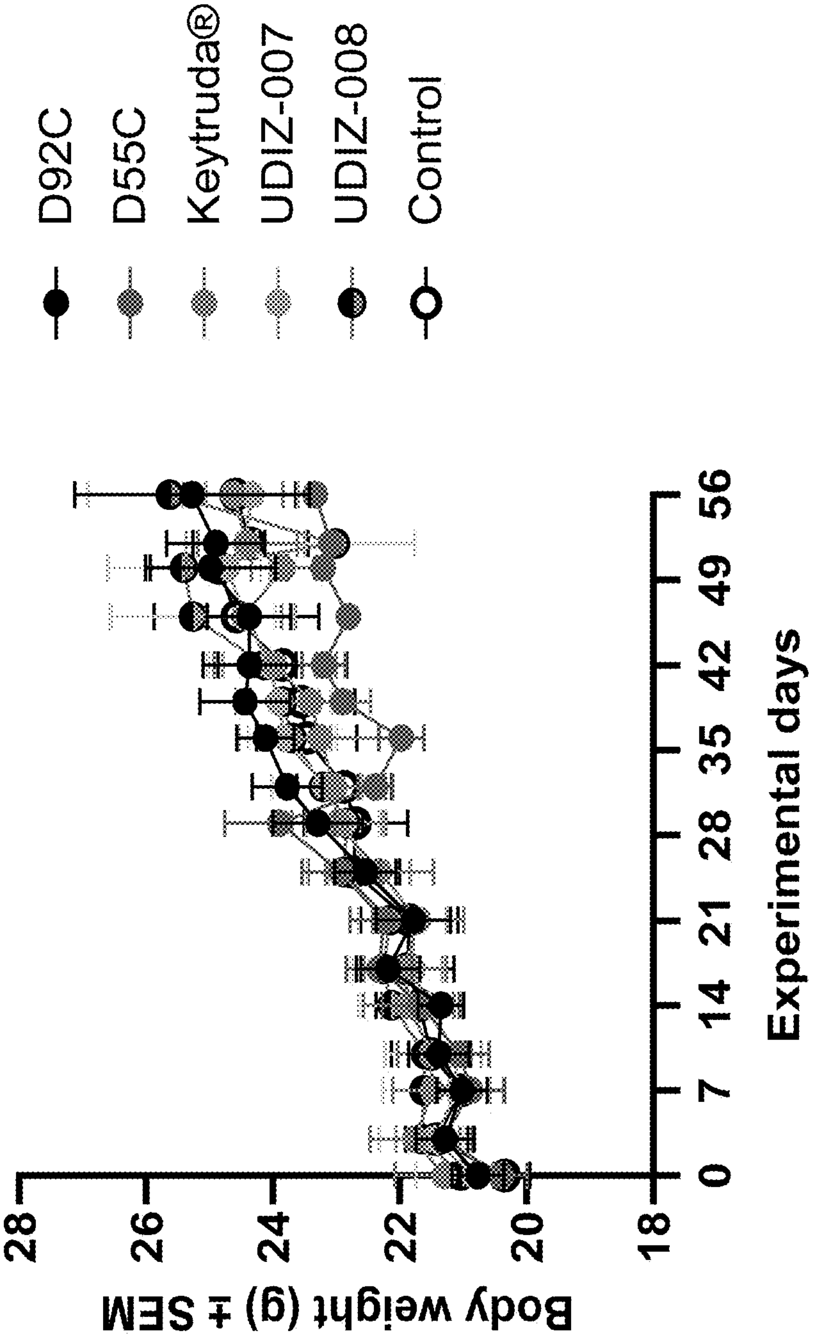
FIG. 24 shows the body weight gain of mice treated with isotype controls Keytruda®, anti-PD-1 antibodies, and non-treated group.
Figure 25A:
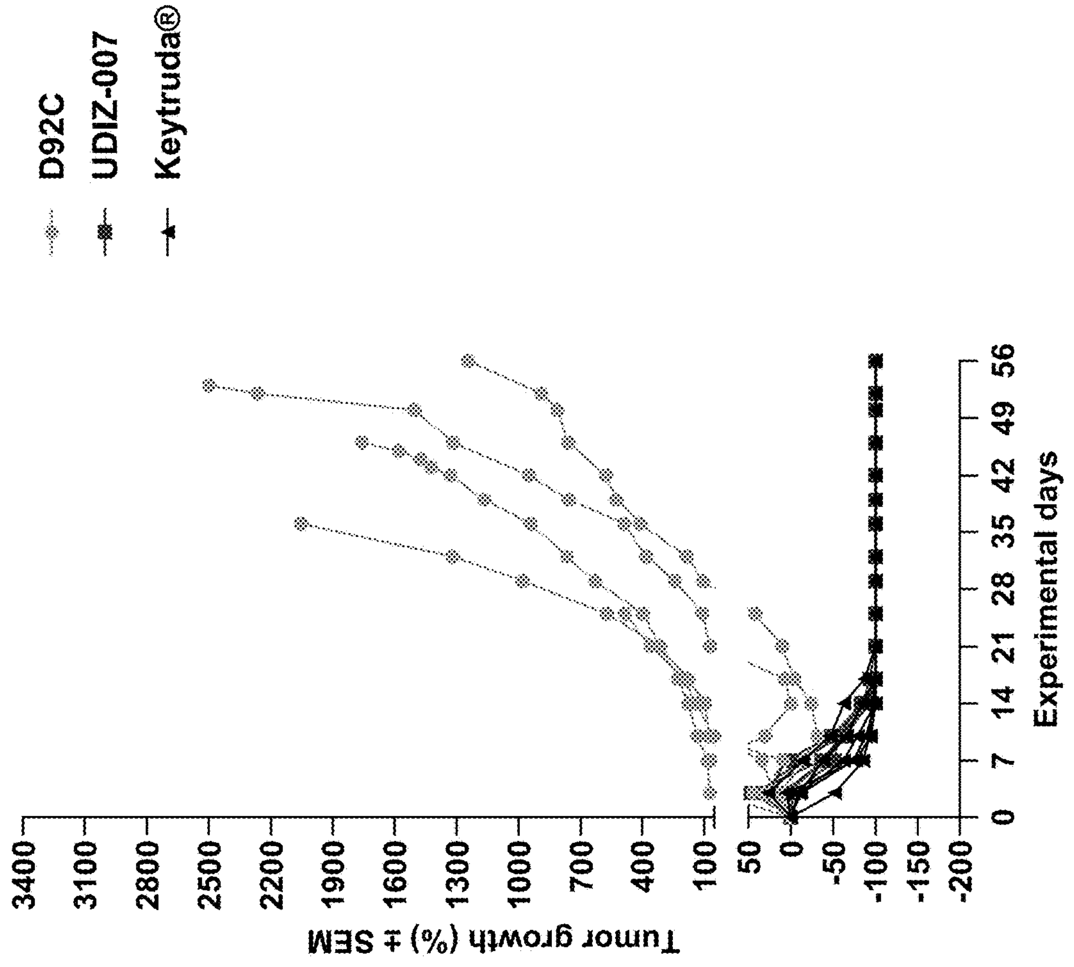
FIGS. 25A-25C show the individual mouse tumor growth treated with UDIZ-007 and UDIZ-008, isotype controls D92C and D55C. Keytruda® was used as a reference.
Figure 25B:
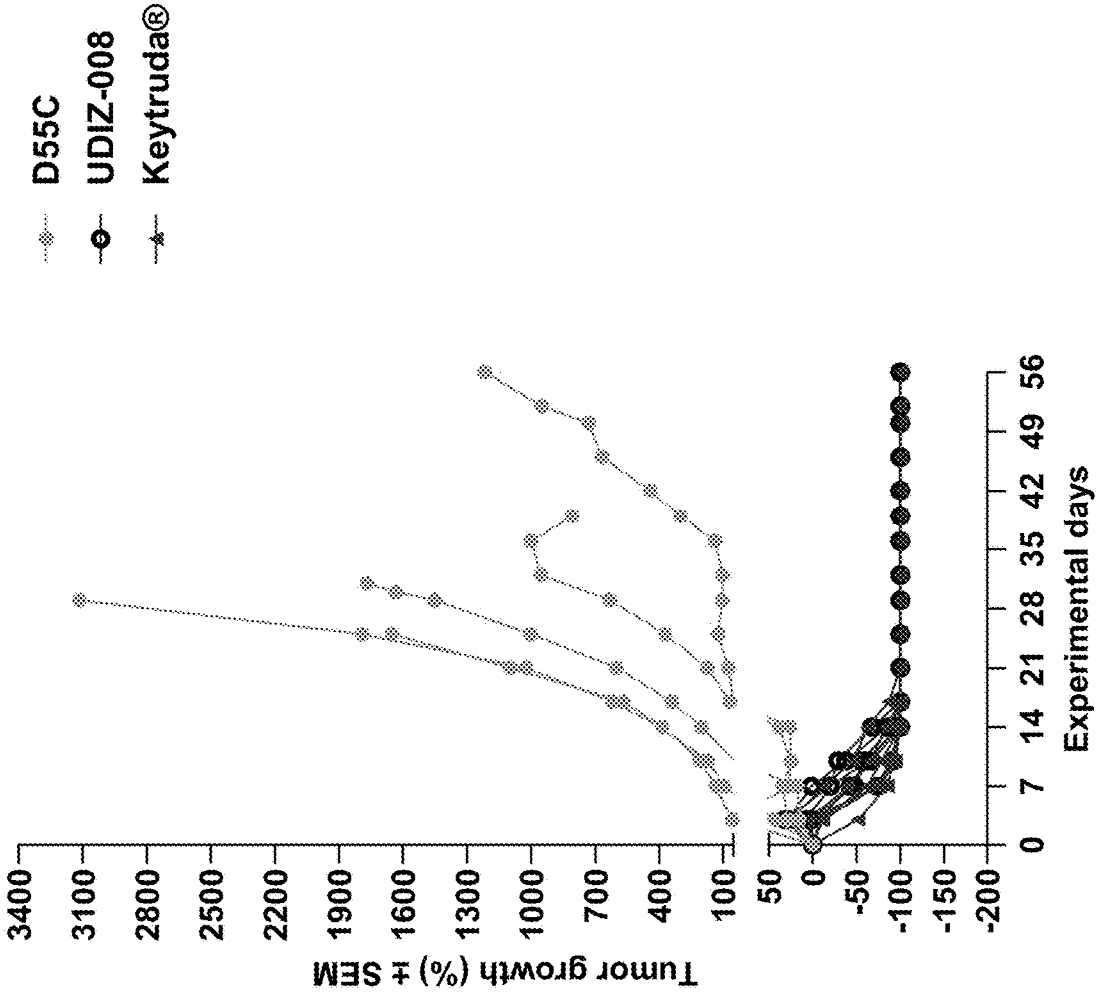
Figure 25C:
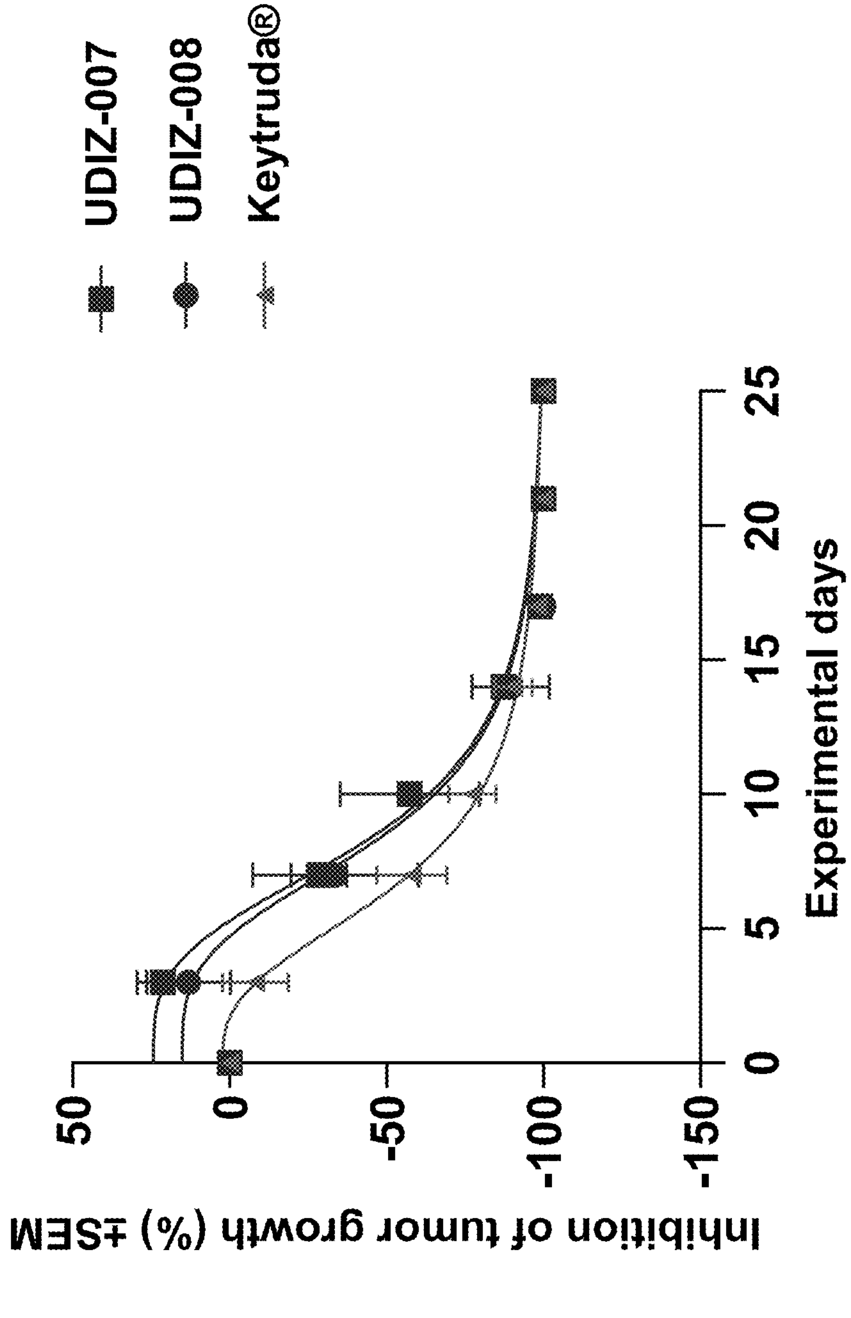

UDIZ-007, UDIZ-008 and Keytruda®, as well as the isotype controls (D92C and D55C) did not significantly modify the body weight gain of the mice during the study (FIG. 24). However, the isotype control groups showed (FIGS. 25A and 25B) an exponential growth of the tumors, in sharp contrast with UDIZ-007, UDIZ-008 and Keytruda®, where the tumors started to shrink after the first week of antibody treatments (FIG. 25C) and disappear around day 17. In fact, the potency of inhibiting tumor growth ($IC_{50}$ expressed in days), estimated by non-linear regression analysis, was 8.12, 7.72 and 5.4 days for UDIZ-008, UDIZ-007 and Keytruda®, respectively. Moreover, no tumor relapse was observed UDIZ-007 (FIG. 25A) and UDIZ-008 (FIG. 25B), similar to Keytruda® during the entire experimental period (56 days). Furthermore, the groups treated with UDIZ-007, UDIZ-008 and Keytruda® had no tumor ulcerations or general lesions, except for one mouse in both the UDIZ-007 and Keytruda® groups (Table 12). While UDIZ-007 and Keytruda® eliminated the tumor in all animals, mice with severe overall lesions could not recover. Survival for both isotype controls (D92C and D55C) was 33.33%, for UDIZ-007 and Keytruda®, were 88.33% and for UDIZ-008 was 100%.

TABLE 12

Clinical evaluation of the efficacy model in B-hDP-1 mice

| Treatment | Survival | Clinical observations |
|---|---|---|
| D92C | 33.33% | 3 mice had mild to moderate ulcerations from day 39 to day 56.<br>1 mouse showed moderate ulceration from day 17 and progressed to severe ulceration from day 21.<br>4 mice were euthanized on days 25, 36, 46, and 53, respectively, for severe symptomatology. |
| D55C | 33.33% | 1 mouse showed moderate ulceration from day 36 and progressed to severe ulceration by day 39.<br>1 mouse presented a moderate lesion by day 50 and progressed to severe by day 52.<br>4 mice were euthanized on days 25, 26, 31, and 39, respectively, due to severe symptomatology. |

TABLE 12-continued

Clinical evaluation of the efficacy model in B-hDP-1 mice

| Treatment | Survival | Clinical observations |
|---|---|---|
| Keytruda ® | 83.33% | 1 mouse presented a moderate lesion from day 21 and progressed to severe by day 25.<br>1 mouse was euthanized on the 25th due to severe symptomatology.<br>None of the mice showed ulceration of the tumors. |
| UDIZ-007 | 83.33% | 1 mouse presented a moderate lesion from day 20 and progressed to severe by day 25.<br>1 mouse was euthanized on the 25th due to severe symptomatology.<br>None of the mice showed ulceration of the tumors. |
| UDIZ-008 | 100% | No mice showed ulcerations on tumors or general lesions. |

Different doses of UDIZ-007 were also tested in the transgenic mouse model for hPD-1. At the highest dose (10 mg/kg), the tumors disappeared around day 17, similar to Keytruda® at the same dose (10 mg/kg), consistent with the previous assay. At 25% of the dose (2.5 mg/kg) a total tumor eradication was observed around day 25. At a 10-fold lower dose (1 mg/kg), the tumors shrank but did not completely disappear, indicating a correlation between the dose of UDIZ-007 and efficacy (tumor eradication).

In summary, both UDIZ-007 and UDIZ-008 antibodies eradicated tumors at 10 mg/kg in a transgenic mouse model for hPD-1 and UDIZ-007 showed a dose-response relationship. Therefore, UDIZ-007/008 alone, in combination with other anti-PD-1 approved antibodies, or as part of multi-specific therapeutic formats linking UDIZ-007/008 with antibodies binding non-overlapping epitopes to enhance the specificity of current anti-PD-1 therapeutic antibodies, could be a new valuable therapeutic option to treat cancer.

Example 9—Pilot Pharmaceutical Development: Formulation and Stability

The potential of UDIZ-007 and UDIZ-008 to be successfully developed as a pharmaceutical product was determined at several levels:

1. Stability at acid pH,
2. Formulation and concentration, and
3. Stress tests.

Stability at Acid pH

Figure 26A:
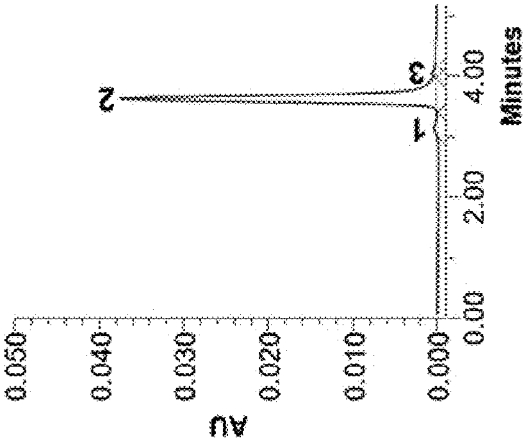
FIGS. 26A-26D show that UDIZ-007 and UDIZ-008 maintained a monomeric content of greater than 99.0% after 75 min at pH 2.8 without mannitol (FIG. 26A) and with 10% mannitol (FIG. 26B). UDIZ-008 had the same stable behavior without mannitol (FIG. 26C) and with 10% mannitol (FIG. 26D) at pH 2.8 for 75 min.
Figure 26B:
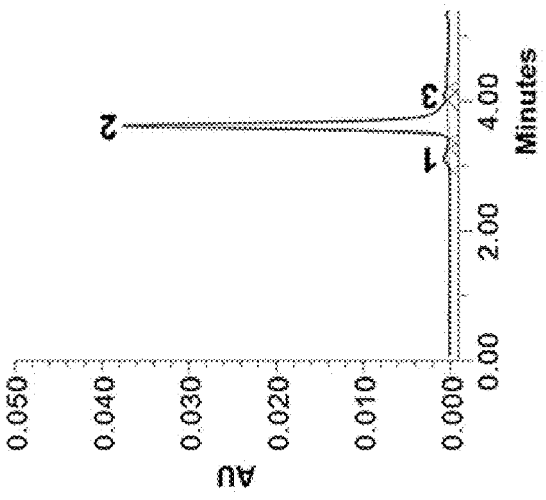
Figure 26C:
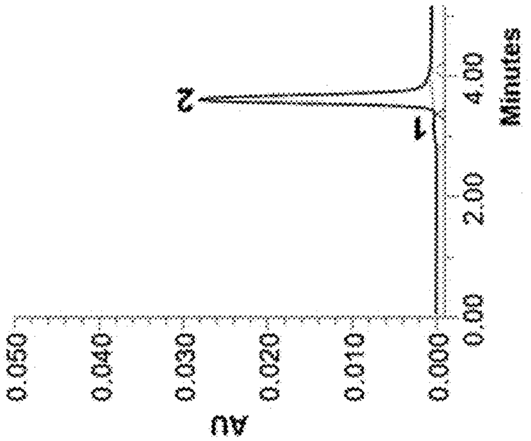
Figure 26D:
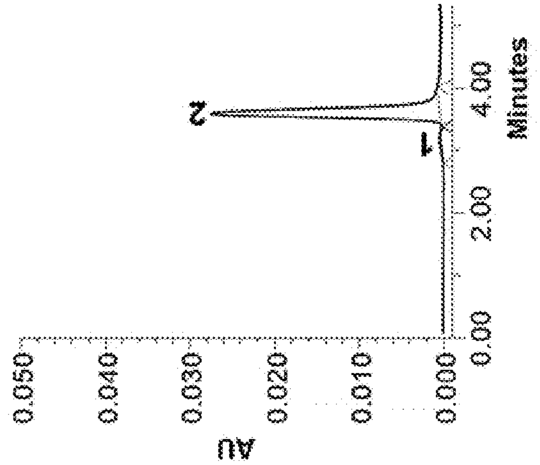

UDIZ-007 and UDIZ-008 were captured on a column with protein A and eluted using 0.1 M acetic acid solution pH 2.8. This process was repeated by adding 10% mannitol to the elution phase to determine if the inclusion of an osmolar agent improved the stability conditions of the candidates. The antibodies were analyzed by molecular exclusion chromatography and, for 75 min, maintained their monomeric percentage purity with and without the addition of mannitol, as shown in Table 13 and FIGS. 26A-26D. These results suggest that UDIZ-007 (FIGS. 26A-26B) and UDIZ-008 (FIGS. 26C-26D) would remain stable during the viral inactivation step of commercial-scale production.

TABLE 13

Purity of UDIZ-007 and UDIZ-008 antibodies in 0.1M acetic acid solution pH 2.8

| | Purity (% monomer) | | | |
|---|---|---|---|---|
| | UDIZ-007 | | UDIZ-008 | |
| Time (min) | pH 2.8 | pH 2.8 + Mannitol | pH 2.8 | pH 2.8 + Mannitol |
| 0 | 97.60 | 96.56 | 98.76 | 98.05 |
| 15 | 97.58 | 97.82 | 98.85 | 98.02 |
| 30 | 97.65 | 97.82 | 98.80 | 97.93 |
| 45 | 97.57 | 98.03 | 98.73 | 98.00 |
| 60 | 97.68 | 97.93 | 98.77 | 97.95 |
| 75 | 97.63 | 97.87 | 98.84 | 97.96 |
| Average | 97.62 | 97.67 | 98.79 | 97.99 |
| Coefficient of variation | 0.04 | 0.55 | 0.05 | 0.05 |

Formulation Buffer and Concentration

The composition of the formulation buffer is described in Table 14 and the physicochemical properties shown in Table 15.

TABLE 14

Buffer formulation for UDIZ-007 and UDIZ-008 as a concentrated solution (30 g/ml) for intravenous infusion. The table shows the quantities for 1 mL of pH 6.0 ± 0.1 solution.

| Component | Concentration | Function |
|---|---|---|
| L-histidine | 0.76 mg | pH buffering system |
| L-histidine monohydrate (monohydrochloride) | 1.08 mg | |
| Mannitol | 32 mg | Osmolar agent |
| Polysorbate 80 | 1.0 mg | Surfactant |
| Injectable water | c.b.p. | Diluent |

TABLE 15

The physicochemical characteristics of the excipient mixture are that it is a clear, colorless solution free of visible particles. (This mixture does not yet contain Polysorbate 80.)

| Analysis | Result | Specification |
|---|---|---|
| pH | 5.94 | 6.0 ± 0.1 |
| Osmolarity (mOsm/kg) | 190 | NA |
| Endotoxin (EU/mL) | 8.0 | <20.0 |
| Sterility/Excipients | Sterile | Sterile |

Figure 27:
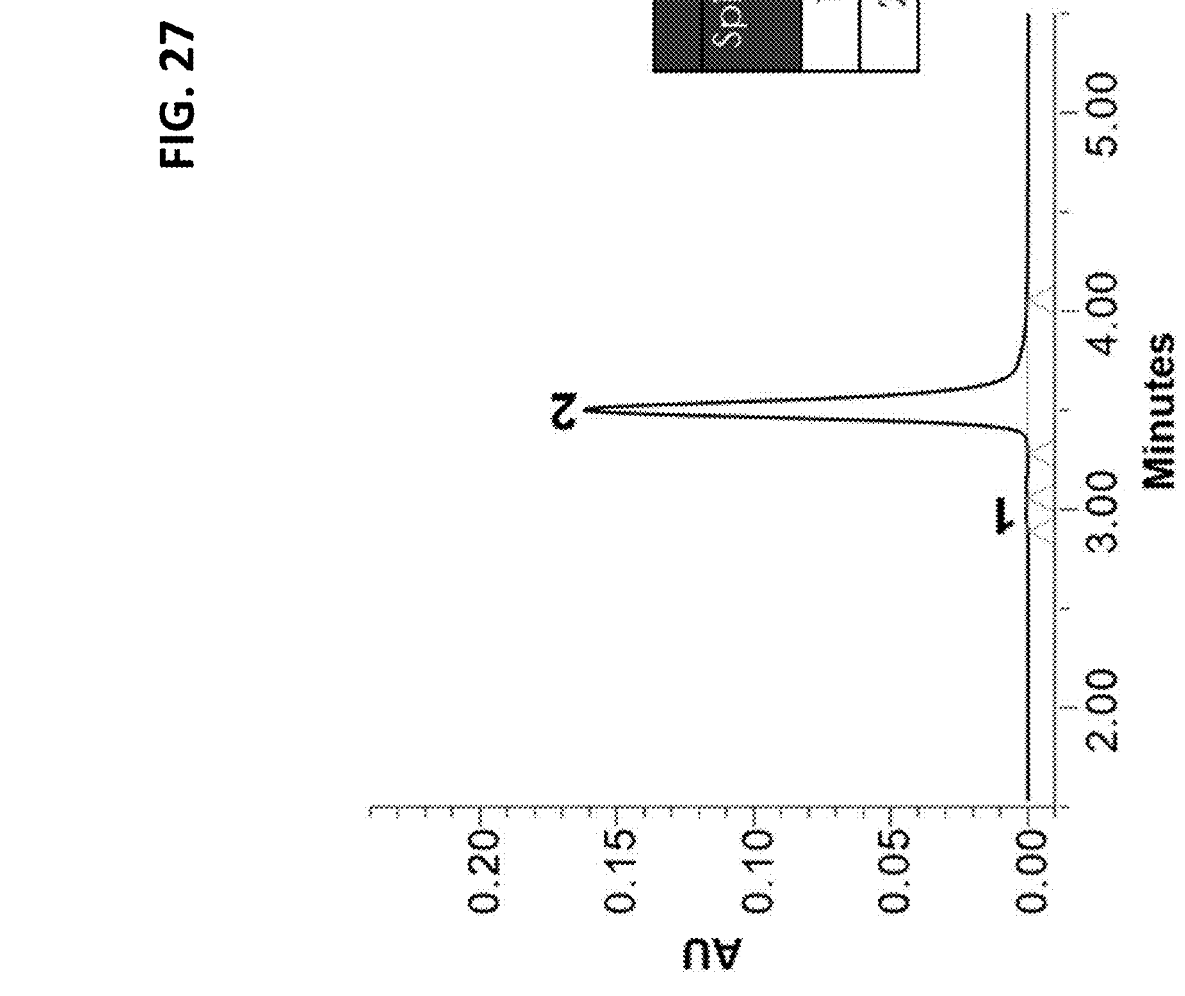
FIG. 27 shows the monomeric content (greater than 99.0%) of UDIZ-007 at 31.6 mg/mL in formulation buffer.
Figure 28:
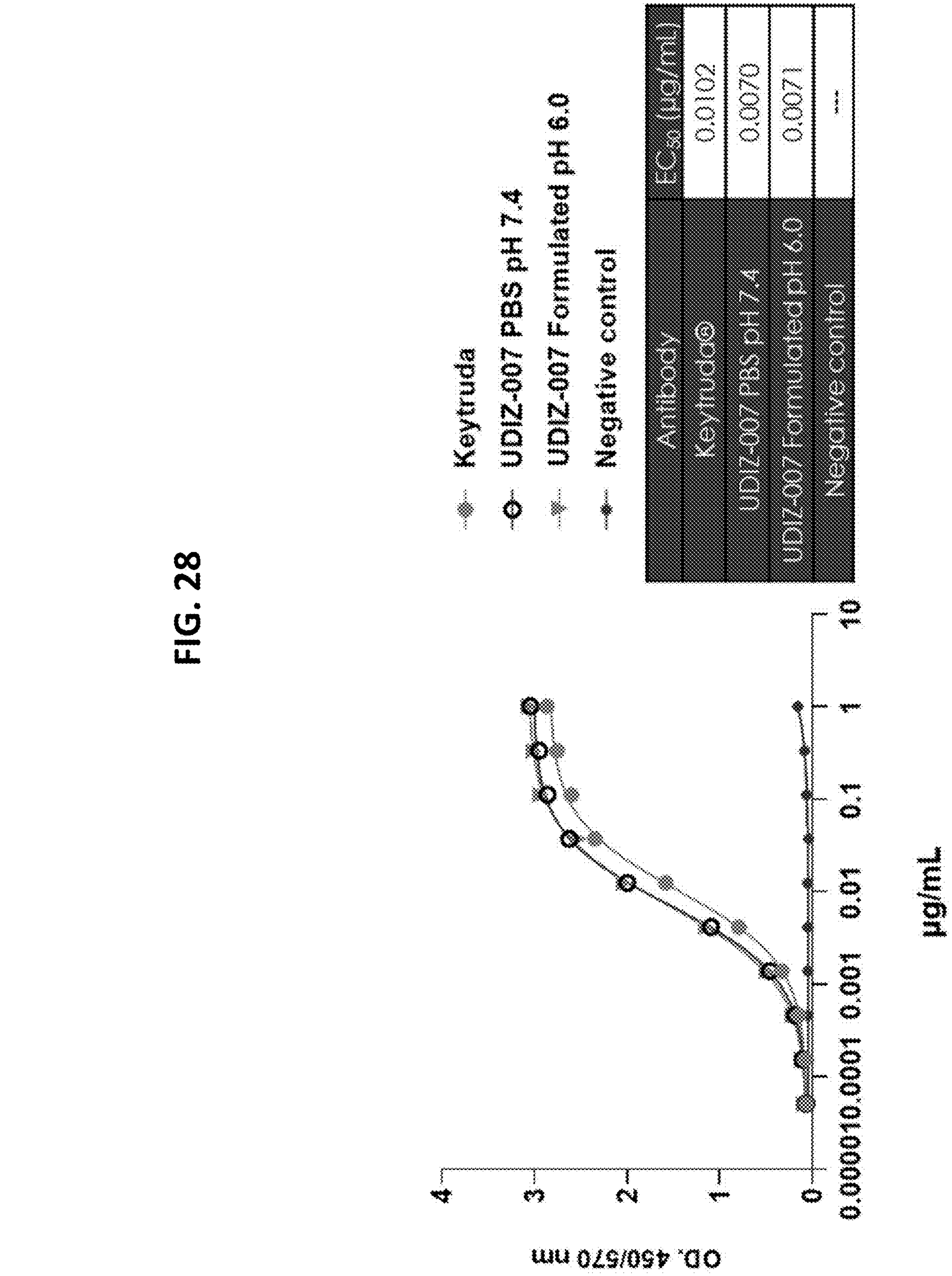
FIG. 28 shows an ELISA of UDIZ-007 at 31.6 mg/mL in formulation buffer. The dose-response curves overlap with an $EC_{50}$ of 0.0070 μg/mL before the formulation and 0.0071 μg/mL after the formulation and concentration.

UDIZ-007, originally in PBS pH 7.4 at 3 mg/mL, was concentrated to 31.6 mg/mL in the formulation buffer as follows. UDIZ-007 was diluted 1:1 with the excipient mix, and 50% of the volume was reduced using 50 kDa centrifugal filters. This process was repeated six times. In the last replacement cycle, the volume was reduced by approximately 10× the initial volume to achieve a >30 mg/mL. As a last step, the required amount of polysorbate 80 was added to reach the 1.0 mg/mL concentration. Table 16 shows the results of the physicochemical characterization of the formulated antibody. FIGS. 27 and 28 show that the monomer content and binding to hPD-1, respectively, was maintained after the formulation at a concentration of 31.6 mg/mL.

TABLE 16

Characterization of formulated UDIZ-007.

| Analysis | UDIZ-007 |
|---|---|
| Maximum concentration (mg/mL) | 31.59 |
| Purity (%) | 99.84 |
| Identity [before formulation] ($EC_{50}$ μg/mL) | 0.0070 |
| Identity [after formulation] ($EC_{50}$ μg/mL) | 0.0071 |
| Acid/basic isoform profile (%) | Acidic 1: 4.9% Acidic 2: 12.3% Main: 53.4% Basic 1: 23.1% Basic 2: 6.3% |
| Endotoxin content (EU/mL) | 1.0 |

Figure 29A:
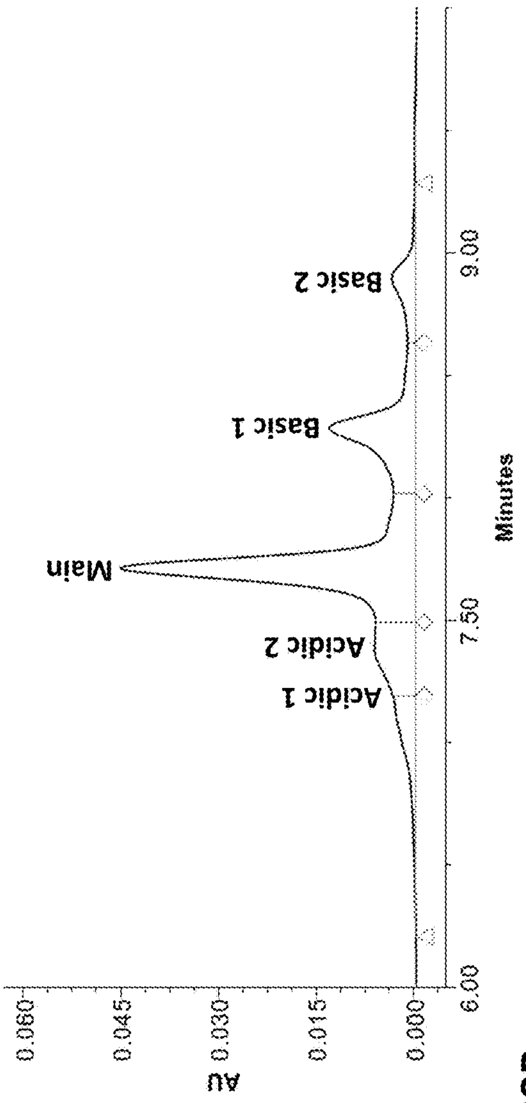
FIGS. 29A and 29B show cation exchange chromatography (CEX) profiles of UDIZ-007 before and after the formulation and concentration at 31.6 mg/mL.
Figure 29B:
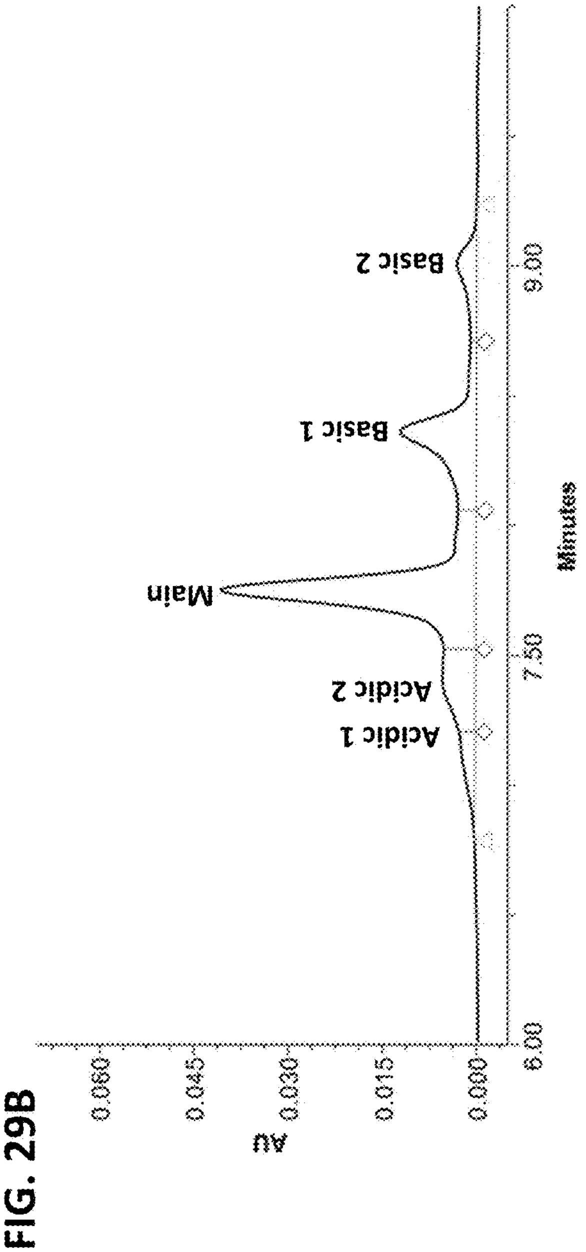

The results in Table 16 indicate that the UDIZ-007 can be concentrated to at least 31.6 mg/mL in the formulation buffer described in Table 15. After the concentration process, UDIZ-007 had a monomeric content >98.5% and maintained its binding to hPD-1. In addition, UDIZ-007 showed a cation exchange chromatography (CEX) profile in the original sample of PBS at 3 mg/mL (FIG. 29A) with two acidic isoforms, two basic isoforms, and a main isoform of 53.4%, which did not change after the formulation at 31.6 mg/mL (FIG. 29B).

Stress Tests

Figure 30A:
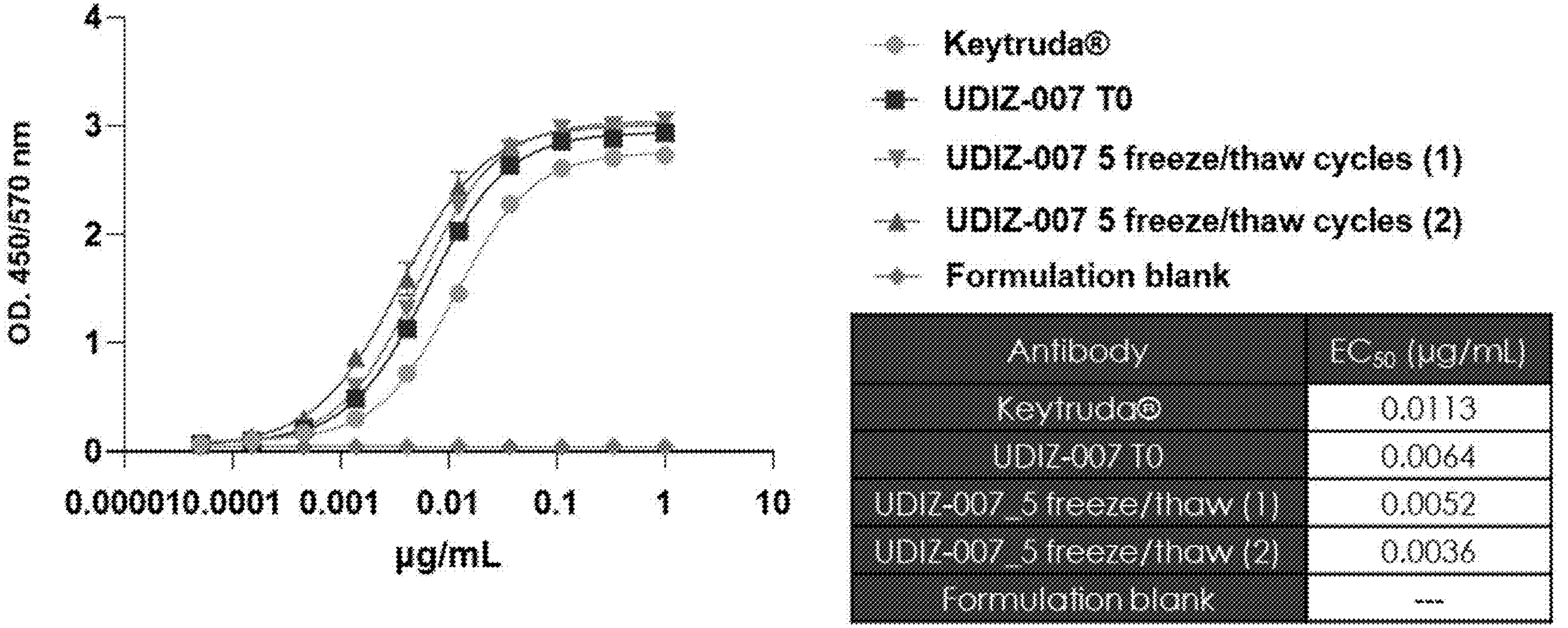
FIGS. 30A-30B show the stability of UDIZ-007 formulated at 31.6 mg/mL after stress tests. UDIZ-007 had an initial $EC_{50}$ of 0.0071 μg/mL. After undergoing five freeze/thaw cycles, it showed an average $EC_{50}$ of 0.0044 μg/mL (FIG. 30A). After 16 hours exposed to 400 Lux/s/16 hours, it presented an average $EC_{50}$ of 0.0053 μg/mL (FIG. 30B).
Figure 30B:
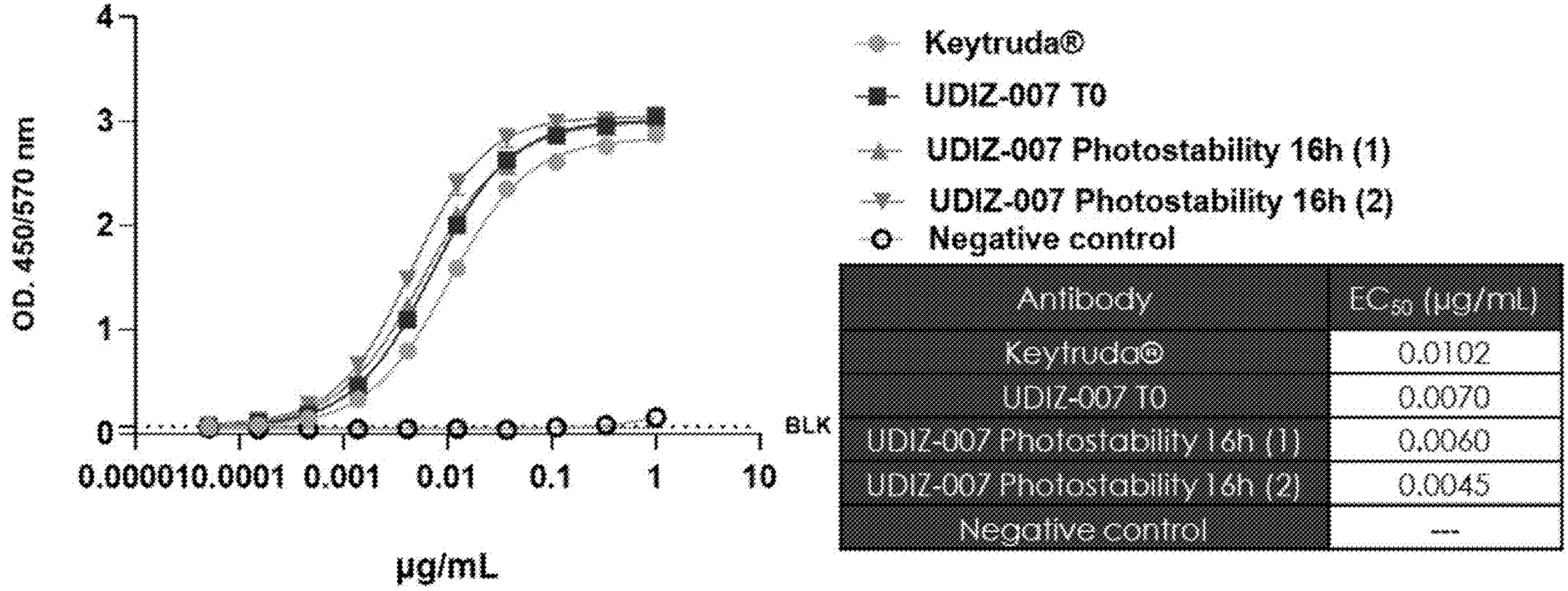

The quality attributes of the UDIZ-007 were evaluated under two stress conditions: (1) freeze-thaw cycles and (2)

exposure to white light. For this purpose, aliquots of UDIZ-007 in the formulation buffer described in Table 15 were submitted to five freeze-thaw cycles [70° C., 15 h/2-8° C., 9 h; per each cycle] and white light (400 Lux/s/16 h). Concentration, purity, identity, and acidic isoform profile (relative percentage of the main isoform) were evaluated. As shown in Table 17, UDIZ-007 kept all the quality attributes assessed after free/thaw cycles. Additionally, Table 18 indicated that UDIZ-007 was also stable for 16 h after exposure to white light. FIGS. 30A and 30B showed that the UDIZ-007 antibody maintained its functional properties as measured by ELISA after both stress conditions.

TABLE 17

Evaluation of the stability of formulated UDIZ-007 subjected to freeze/thaw cycles.

| Test | Initial | Final | Percentage of change | Specification | Result |
|---|---|---|---|---|---|
| Concentration (mg/mL) | 31.59 | 29.80 | −5.7% | ±10% | Complies |
| Purity (%) | 99.84 | 100.00 | 0.2% | ≥98% | Complies |
| Identity ($EC_{50}$ µg/mL) | 0.0071 | 0.0044 | NA | 0.0020-0.0099 | Complies |
| Acid/base isoform profile (% main isoform) | 53.4 | 54.3 | 1.7% | ±10% | Complies |

TABLE 18

Evaluation of the stability of formulated UDIZ-007 exposed to white light.

| Test | Initial | Final | Percentage of change | Specification | Result |
|---|---|---|---|---|---|
| Concentration (mg/mL) | 31.59 | 33.21 | 5.1% | ±10% | Complies |
| Purity (%) | 99.84 | 99.56 | −0.3% | ≥98% | Complies |
| Identity (µg/mL) | 0.0071 | 0.0053 | NA | 0.0020-0.0099 | Complies |
| Acid/base isoform profile (% main isoform) | 53.4 | 52.9 | −0.9 | ±10% | Complies |

In sum, UDIZ-007 was successfully formulated at a concentration of at least 31.6 mg/mL and is stable under various stress conditions.

* * *

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

The invention claimed is:

1. A binding molecule that binds to programmed cell death protein 1 PD-1), wherein the binding molecule comprises:

a) a variable heavy chain CDR1 (HCDR1) comprising an amino acid sequence of SEQ ID NO: 1;

b) a variable heavy chain CDR2 (HCDR2) comprising an amino acid sequence of SEQ ID NO: 2;

c) a variable heavy chain CDR3 (HCDR3) comprising an amino acid sequence of SEQ ID NO: 3;

d) a variable light chain CDR1 (LCDR1) comprising an amino acid sequence of SEQ ID NO: 4;

e) a variable light chain CDR2 (LCDR2) comprising an amino acid sequence of SEQ ID NO: 5; and f) a variable light chain CDR3 (LCDR3) comprising an amino acid sequence of SEQ ID NO: 6, wherein the binding molecule is numbered with reference to Kabat numbering system.

2. The binding molecule of claim 1, wherein the binding molecule binds amino acid residues of 80-115 (SEQ ID NO: 29) of human PD-1 when numbered in accordance with SEQ ID NO: 25.

3. The binding molecule of claim 1, wherein the HCDR1, HCDR2, and HCDR3 of the binding molecule binds residues 80-104 (SEQ ID NO: 26).

4. The binding molecule of claim 1, wherein the HCDR2, LCDR1, and LCDR2, of the binding molecule binds residues 105-115 (SEQ ID NO: 27).

5. The binding molecule of claim 1, wherein the amino acid residues of 105-115 (SEQ ID NO: 27) of human PD-1 do not overlap with the residues involved in hPD-1: hPD-L1 interaction.

6. The binding molecule of claim 1, wherein the binding molecule sterically blocks interaction between hPD-1 and hPD-L1.

7. The binding molecule of claim 1, wherein the binding molecule comprises a heavy chain variable domain (VH) comprising an amino acid sequence that is at least 85% identical to SEQ ID NO: 19, and a light chain variable domain (VL) comprising an amino acid sequence that is at least 85% identical to SEQ ID NO: 20.

8. The binding molecule of claim 1, wherein the binding molecule is a monoclonal antibody or antigen-binding fragment thereof and wherein the monoclonal antibody or antigen-binding fragment thereof comprises an IgG isotype selected from the group consisting of IgG1, IgG2, IgG3, IgG4, and a variant thereof.

9. The binding molecule of claim 8, wherein the binding molecule is a fully human monoclonal antibody comprising an IgG4-PE.

10. The binding molecule of claim 9, wherein the binding molecule comprises a heavy chain comprising an amino acid sequence that is at least about 85% identical to SEQ ID NO: 21, and a light chain comprising an amino acid sequence that is at least about 85% identical to SEQ ID NO: 22.

11. The binding molecule of claim 8, wherein the binding molecule is a fully human monoclonal antibody comprising an IgG1-LALA.

12. The binding molecule of claim 11, wherein the binding molecule comprises a heavy chain comprising an amino acid sequence that is at least about 85% identical to SEQ ID N NO: 23, and a light chain comprising an amino acid sequence that is at least about 85% identical to SEQ ID NO: 24.

13. A polynucleotide encoding the binding molecule of claim 1.

14. A vector, comprising the polynucleotide of claim 13.

15. A pharmaceutical composition comprising the binding molecule of claim 1, wherein the pharmaceutical composition further comprises a pharmaceutically acceptable carrier.

16. A method of treating a cancer in a subject in need thereof, comprising administering to the subject a therapeutically effective amount of the pharmaceutical composition of claim 15.

17. The method of claim 16, comprising administering the therapeutically effective amount of the pharmaceutical composition with a therapeutically effective amount of one or more additional therapeutic agent, wherein the one or more therapeutic additional agent comprises an anti-PD1 antibody.

18. The method of claim 16, wherein the cancer is a solid tumor, or a blood cancer.

19. The method of claim 16, wherein the cancer is resistant, refractory, and/or insensitive to at least one prior therapeutic agent to treat the cancer, wherein the at least one prior therapeutic agent comprises an anti-PD1 antibody.

* * * * *